United States Patent
Takami et al.

[11] Patent Number: 6,084,418
[45] Date of Patent: Jul. 4, 2000

[54] METHOD FOR ACCURATELY DETECTING SENSOR ELEMENT RESISTANCE

[75] Inventors: Masayuki Takami, Kariya; Tomomichi Mizoguchi, Nagoya; Satoshi Haseda, Okazaki; Kazuhiro Okazaki, Anjo; Koji Jono, Obu, all of Japan

[73] Assignee: Denso Corporation, Kariya, Japan

[21] Appl. No.: 09/038,005

[22] Filed: Mar. 11, 1998

Related U.S. Application Data

[63] Continuation-in-part of application No. 08/807,367, Feb. 27, 1997, abandoned.

[30] Foreign Application Priority Data

Feb. 28, 1996 [JP] Japan .................................. 8-041774
Aug. 6, 1996 [JP] Japan .................................. 8-207410
Aug. 27, 1997 [JP] Japan .................................. 9-231014

[51] Int. Cl.$^7$ .............. G01N 27/04; G01N 27/419; G01R 27/08; G01R 27/22
[52] U.S. Cl. .............. 324/717; 324/713; 324/71.1; 204/424; 205/783.5; 205/784.5
[58] Field of Search ..................... 324/710, 711, 324/713, 717, 71.1; 204/421, 424; 205/782, 783.5, 784, 784.5, 785.5

[56] References Cited

U.S. PATENT DOCUMENTS

| | | | |
|---|---|---|---|
| 4,272,330 | 6/1981 | Hetrick | 205/784 |
| 4,419,190 | 12/1983 | Dietz et al. | 204/1 T |
| 4,505,802 | 3/1985 | Mase et al. | 204/425 |
| 4,543,176 | 9/1985 | Harada et al. | 204/406 |
| 4,576,705 | 3/1986 | Kondo et al. | 204/406 |
| 4,626,338 | 12/1986 | Kondo et al. | 204/406 |
| 4,721,084 | 1/1988 | Kawanabe et al. | 123/440 |
| 5,405,521 | 4/1995 | Nakamori et al. | 204/425 |
| 5,562,815 | 10/1996 | Preidel | 205/782 |
| 5,833,836 | 11/1998 | Takami et al. | 205/785 |
| 5,935,400 | 8/1999 | Takami et al. | 204/425 |

FOREIGN PATENT DOCUMENTS

| | | |
|---|---|---|
| 62-249046 | 10/1987 | Japan . |
| 63-182560 | 7/1988 | Japan . |
| 2 285 314 | 7/1995 | United Kingdom . |

Primary Examiner—Glenn W. Brown
Attorney, Agent, or Firm—Pillsbury Madison & Sutro LLP

[57] ABSTRACT

An air-fuel ratio sensor generates linear air-fuel ratio detection signals proportional to concentration of oxygen in exhaust gas from an engine in response to a command voltage from a microprocessor. A bias command signal generated by the microprocessor is provided to a D/A converter which converts it to an analog signal. Thereafter, the signal is provided to an LPF for removing the high frequency components of the analog signal. Output voltage of the LPF is provided to a bias control circuit. A single AC signal which has a predetermined frequency and which is provided with a predetermined time constant (about 159 $\mu$s) by the LPF is applied to the air-fuel ratio sensor. Element resistance of the air-fuel ratio sensor is detected based on the voltage of the AC signal and the change in the current level of the air-fuel ratio sensor caused by the application of the AC signal.

26 Claims, 37 Drawing Sheets

OUTPUT VOLTAGE Vb
OF D/A CONV. 21

OUTPUT VOLTAGE
OF LPF 22

FIG. IIA
APPLIED VOLTAGE (V)
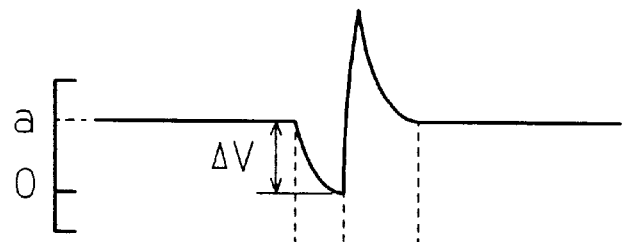
FIG. IIB
SENSOR CURRENT (A)
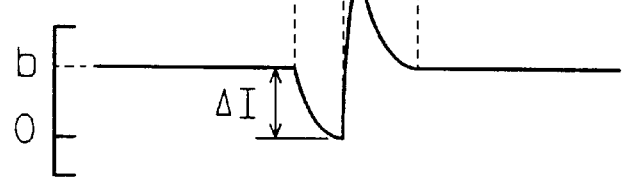
FIG. IIC
APPLIED VOLTAGE (V)
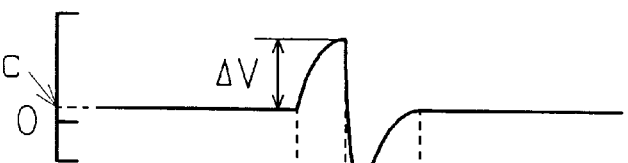
FIG. IID
SENSOR CURRENT (A)
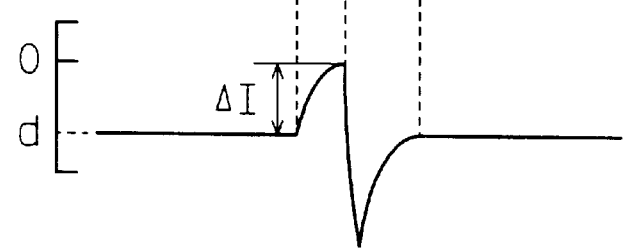

APPLIED VOLTAGE (V)

SENSOR CURRENT (A)

APPLIED VOLTAGE (V)

SENSOR CURRENT (A)

OUTPUT VOLTAGE Vb
OF D/A 21

OUTPUT VOLTAGE Vc
OF LPF 22

SENSOR
CURRENT Ip

6,084,418

METHOD FOR ACCURATELY DETECTING SENSOR ELEMENT RESISTANCE

CROSS-REFERENCE TO RELATED APPLICATIONS

This application is a continuation-in-part of a U.S. patent application Ser. No. 08/807,367 filed on Feb. 27, 1997, now abandoned and incorporates herein by reference Japanese Patent Applications No. Hei-8-41774, Hei-8-207410 and Hei-9-231014, filed on Feb. 28, 1996, Aug. 6, 1996 and Aug. 27, 1997, respectively.

BACKGROUND OF THE INVENTION

1. Field of the Invention

The present invention relates to an oxygen concentration sensor for detecting oxygen concentration, for example, in exhaust gas from a vehicle engine. More specifically, the present invention relates to a method for detecting element resistance based on voltage and current frequency characteristics of the oxygen concentration sensor.

2. Description of Related Art

In recent years, with regards to the control of air-fuel ratio of a vehicle engine, there have been demands for improving control precision, for promoting lean burning and the like. To meet such demands, a linear type air-fuel ratio sensor (oxygen concentration sensor) for linearly detecting the air-fuel ratio (that is, oxygen content of exhaust gas) of an air mixture drawn into the engine has been proposed and implemented. In order to maintain its precise level of detection, the air-fuel ratio sensor of the above-mentioned type must be kept in an active state. In general, this active state is maintained by heating a sensor element of the sensor by controlling the actuation of a heater attached to the sensor.

According to such actuation control of the heater, the temperature of the sensor element (hereinafter simply referred to as "element temperature") is detected, and feedback control is subsequently performed so that the element temperature ultimately reaches a desired activation temperature (e.g., about 700° C.). In this case, although the element temperature may be detected on a real-time basis based on a result detected by a temperature sensor attached to the sensor element, the attachment of the temperature sensor is likely to raise the overall cost of the sensor device. Because of this, there have been proposals to detect the resistance of the sensor element (hereinafter simply referred to as "element resistance") based on a predetermined relationship between element resistance and the element temperature, and thus, derive the element temperature from the detected element resistance. It is to be noted that the detected element resistance can also be used for determining, for example, the level of deterioration in the characteristics of the sensor.

FIGS. 53A and 53B are graphs that show a conventional procedure for detecting the element resistance as, for example, disclosed in U.S. Pat. No. 4,543,176. These figures illustrate a case in which a limit current type oxygen concentration sensor is used as an air-fuel ratio sensor for performing engine control. As shown in FIG. 53A, before a time instant t11, a predetermined voltage (positive voltage Vpos) for detecting the air-fuel ratio is applied to the sensor element. The air-fuel ratio is obtained based on a sensor current Ipos generated in accordance with the applied voltage Vpos as shown in FIG. 53B. Between time t11 and t12, a negative voltage Vneg for detecting element resistance is applied and the corresponding sensor current Ineg is detected. Then, the negative voltage Vneg is divided by the sensor current Ineg to obtain element resistance ZDC (ZDC=Vneg/Ineg). This method is generally known as a method for detecting element resistance based on DC characteristics of the air-fuel ratio sensor.

Although the above conventional method is used for detecting element resistance (the direct current component of impedance) by applying DC voltage to the sensor element, U.S. Pat. No. 4,419,190 discloses a method for detecting element resistance through the application of an alternating current (AC) voltage to the sensor element. In this method, alternating current is continuously applied to the air-fuel ratio sensor and the sensor output from the air-fuel ratio sensor is passed through a low-pass filter (hereinafter referred to as LPF) to detect the air-fuel ratio. The same sensor output is passed through a high-pass filter (hereinafter referred to as HPF) and averaged to detect alternating current impedance. This method is generally known as a method for detecting element resistance using AC characteristics of the air-fuel ratio sensor.

However, all the conventional methods described above have the following problems. Namely, according to the DC impedance method, when a negative voltage Vneg having a rectangular waveform is applied, the sensor current Ineg changes rapidly and thus, the peak current of the sensor cannot be detected accurately. For this reason, the detection of the peak current has to be discontinued until the sensor current stabilizes. Accordingly, there will be a period of time during which the air-fuel ratio cannot be detected. Furthermore, this problem of being unable to detect the peak current during the application of the voltage having a rectangular waveform will likely occur also in the method of detecting element resistance based on AC characteristics.

With the AC impedance method (disclosed in U.S. Pat. No. 4,419,190), because the sensor output is passed through the LPF to detect the air-fuel ratio, problems in the air-fuel ratio output such as phase shift and AC noise may occur. These problems are particularly evident when the operating condition of the engine is in a transition.

SUMMARY OF THE INVENTION

In view of the foregoing problems in the prior art, an object of the present invention is to provide a novel method for detecting element resistance of an oxygen sensor. This method aims to accurately detect element resistance and reduce detection time of the element resistance.

To achieve these aims, a first aspect of the present invention provides a method for detecting element resistance of the oxygen sensor which includes the steps of setting a time constant corresponding to a frequency at which impedance characteristics of an oxygen sensor are stable, applying a changing voltage having the time constant to the oxygen sensor, determining a current change in electric current flowing in the oxygen sensor due to the changing voltage, and determining element resistance of the oxygen sensor based on the changing voltage and the current change.

In this way, because a changing voltage that has a predetermined time constant is applied to the oxygen sensor, sudden changes in the electric current level of the oxygen sensor can be prevented and thus, the level of current change can be accurately detected. Accordingly, the element resistance of the oxygen sensor can be detected accurately.

Preferably, the step of applying the changing voltage applies a changing voltage that has a single voltage waveform having the time constant. In this way, compared with conventional methods which detect the element resistance based on a set of continuous voltage signals, detection of the element resistance of the oxygen sensor can be performed in a short period of time.

Preferably, in setting the time constant, the above method determines a frequency range at which the impedance characteristics of the oxygen sensor are stable and sets the time constant to correspond to a predetermined frequency within such frequency range. The impedance characteristics of the sensor element of the limit current type oxygen sensor stabilize at voltage change frequencies of no less than 1 kHz. In this way, the time constant should be set to 159 $\mu$s which corresponds to a cutoff frequency of no less than 1 kHz.

Preferably, the step of applying the changing voltage applies a changing voltage that has a negative slope portion and a positive slope portion, where the step of determining the current change determines the current change due to one of the negative slope portion and the positive slope portion, and the step of determining the element resistance is for determining the element resistance based on the negative slope portion of the changing voltage and the current change when the step of determining the current change determines the current change based on the negative slope portion and for determining the element resistance based on the positive slope portion of the changing voltage and the current change when the step of determining the current change determines the current change based on the positive slope portion.

Preferably, the step of applying the changing voltage applies a changing voltage having a positive slope portion when the oxygen sensor detects a lean air-fuel ratio applies a changing voltage having a negative slope portion when the oxygen sensor detects a rich air-fuel ratio; and the step of determining the current change determines the current change due to the negative slope portion when the oxygen sensor detects the lean air-fuel ratio determines the current change due to the positive slope portion when the oxygen sensor detects the rich air-fuel ratio. In this way, the current of the oxygen sensor can be detected accurately without exceeding the dynamic range of a sensor current detector.

Another aspect of the present invention provides a method for detecting element resistance of the oxygen sensor which includes the step of selectively executing at least one of a first detection method and a second detection method. The first detection method involves the steps of setting a time constant corresponding to a frequency at which impedance characteristics of an oxygen sensor are stable, applying a changing voltage having the time constant to the oxygen sensor, determining a current change in electric current flowing in the oxygen sensor due to the changing voltage and determining element resistance of the oxygen sensor based on the changing voltage and the current change. The second detection method involves the steps of deactuating the oxygen sensor, detecting a voltage change in voltage of the oxygen sensor after deactuating the oxygen sensor, detecting a current change in the electric current of the oxygen sensor due to the voltage change and determining the element resistance based on the voltage change and the current change.

In this way, when the output current of the oxygen sensor is proximate to the center of the detectable current range, the first detection method can be used to detect the element resistance of the oxygen sensor. On the other hand, if the output current is proximate to the maximum or minimum value of the current range, the second detection method can be used to accurately detect the element resistance of the oxygen sensor. Thus, the appropriate detection method can be selected for detecting the current of the oxygen sensor in accordance with the level of its current.

BRIEF DESCRIPTION OF THE DRAWINGS

Additional objects and advantages of the present invention will be more readily apparent from the following detailed description of preferred embodiments thereof when taken together with the accompanying drawings in which:

FIGS. 11A–11D are graphs showing examples of changes in voltage applied to the air-fuel ratio sensor and respective current changes due to such voltage changes;

DETAILED DESCRIPTION OF PREFERRED EMBODIMENTS

Preferred embodiments of the present invention are described hereinafter with reference to the accompanying drawings.

Hereinafter, a first embodiment in which the present invention is applied to an air-fuel ratio detection device will be described. The air-fuel ratio detection device according to the present embodiment is applied to an electronic injection control gasoline engine that is installed in a vehicle. An air-fuel ratio control system of the engine controls the amount of fuel to be injected to the engine based on the air-fuel ratio detected by the air-fuel ratio detection device to obtain a desired air-fuel ratio. The procedures for detecting air-fuel ratio (A/F) using an air-fuel ratio sensor and for detecting element resistance using AC characteristics of the air-fuel ratio sensor are explained in detail hereinafter.

Figure 1:
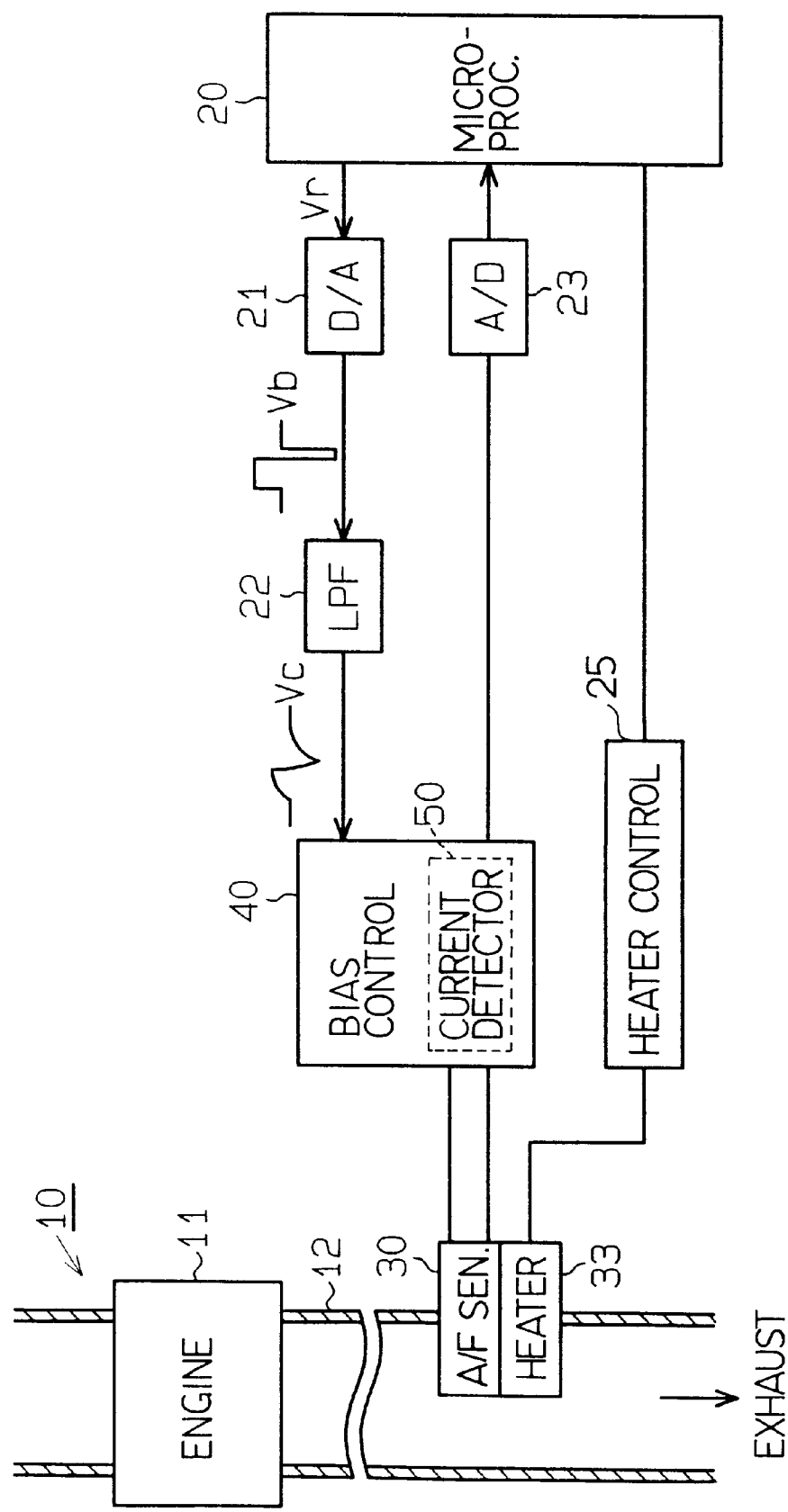
FIG. 1 is a schematic diagram showing the construction of an air-fuel ratio detection device according to a first embodiment of the present invention.

FIG. 1 is a schematic diagram showing a construction of an air-fuel ratio detection device according to the present embodiment. As shown in FIG. 1, the air-fuel ratio detection device includes a limit current type air-fuel ratio sensor (hereinafter referred to as A/F ratio sensor) 30 which serves as an oxygen concentration sensor. The A/F ratio sensor 30 is installed in an exhaust pipe 12 that extends from a main body of an engine 11. The A/F ratio sensor 30 generates a linear air-fuel ratio detection signal which has a value proportional to oxygen concentration in the exhaust gas in response to the application of voltage as commanded by a microprocessor 20. The microprocessor 20 includes a CPU, ROM, RAM and the like. The microprocessor 20 controls a bias control circuit 40 and a heater control circuit 25, which will be described later, in accordance with predetermined control programs.

Figure 2:
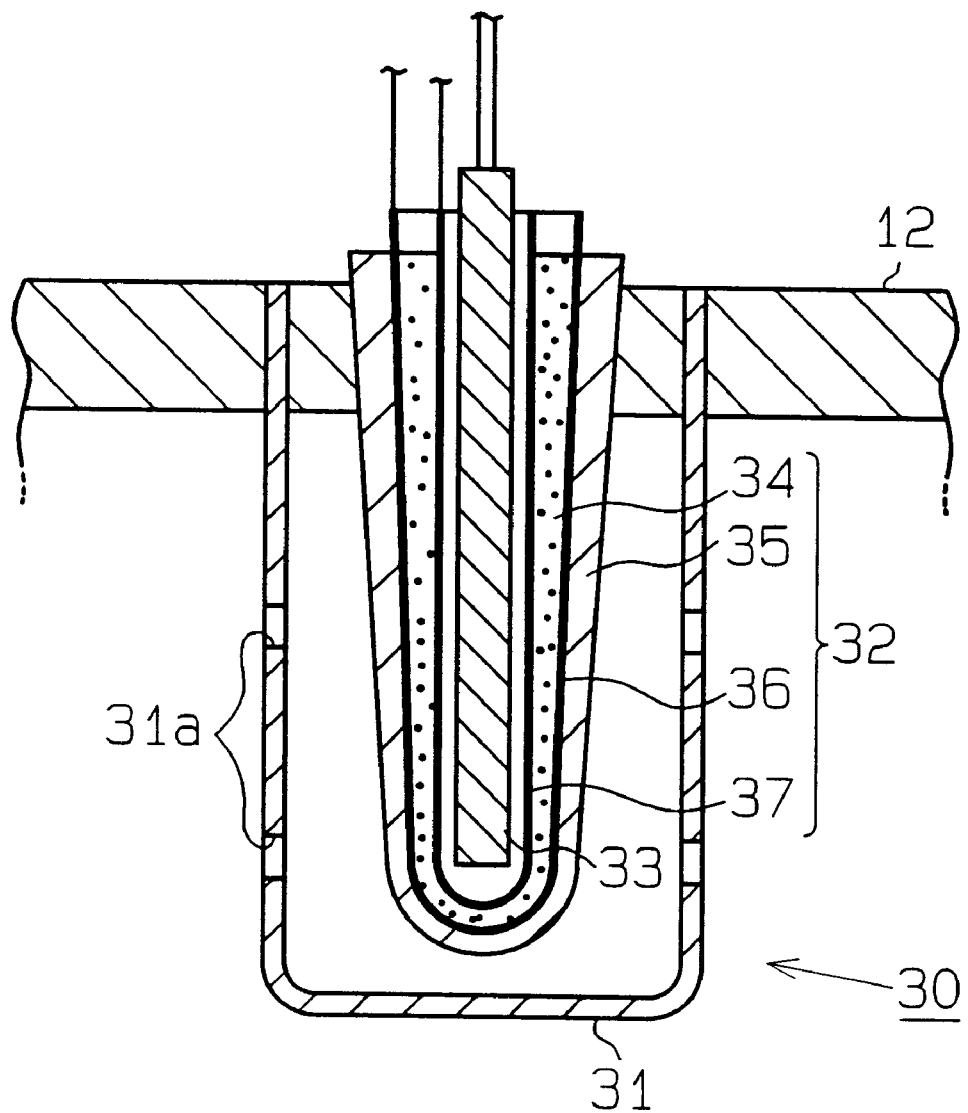
FIG. 2 is a cross-sectional view showing a detailed construction of an air-fuel ratio sensor of the air-fuel ratio detection device.

FIG. 2 is a schematic cross-sectional view of the A/F ratio sensor 30. As shown in FIG. 2, the A/F ratio sensor 30 protrudes towards the interior of the exhaust pipe 12. The A/F ratio sensor 30 mainly includes a cover 31, a sensor main body 32 (otherwise known as the sensor element) and a heater 33. The cover 31 has a U-shaped cross section. A great number of small holes 31a are formed on the periphery of the cover 31 for facilitating communication between the interior and exterior of the cover 31. The sensor main body 32 generates a limit current corresponding to the oxygen concentration in a region where the air-fuel ratio is lean or concentration of unburnt gases (CO, HC, $H_2$ and the like) in a region where the air-fuel ratio is rich.

A construction of the sensor main body 32 will be described in detail below. In the sensor main body 32, an exhaust gas side electrode layer 36 is attached to the outer surface of a solid electrolytic layer 34 that has a U-shaped cross section and an atmosphere side electrode layer 37 is attached to the inner surface of the same electrolytic layer 34. Furthermore, a diffusion resistor layer 35 is formed on the outer surface of the exhaust gas side electrode layer 36 via plasma spraying or the like. The solid electrolytic layer 34 has an oxygen ion conductive oxide sintered body obtained by dissolving $ZrO_2$, $HfO_2$, $ThO_2$, $Bi_2O_3$ or the like with CaO, MgO, $Y_2O_3$, $Yb_2O_3$ or the like serving as stabilizers. The diffusion resistor layer 35 is composed of a heat resistant inorganic material such as alumina, magnesia, silicate substance, spinel, mullite or the like. Both the exhaust gas side electrode layer 36 and the atmosphere side electrode layer 37 are formed of a precious metal that has high catalytic properties such as platinum or the like and the surface thereof is coated with porous chemical materials. The area and thickness of the exhaust gas side electrode 36 are about 10–100 $mm^2$ and about 0.5–2.0 mm, respectively, whereas the atmosphere side electrode layer 37 has a surface area of less than 10 $mm^2$ and a thickness of about 0.5–2.0 mm, respectively.

The heater 33 is disposed inside the atmosphere side electrode layer 37 and generates heat energy to heat the sensor main body 32 (which includes the atmosphere side electrode layer 37, the solid electrode layer 34, the exhaust gas side electrode layer 36 and the diffusion resistor layer 35). The heater 33 has a heat generation capacity sufficient for activating the sensor main body 32.

According to the A/F ratio sensor 30 constructed as described above, the sensor main body 32 generates a limit current corresponding to oxygen concentration in the region where the air-fuel ratio is on the lean side with respect to a stoichiometric air-fuel ratio value. In this case, the limit current corresponding to oxygen concentration is determined by the area of the exhaust gas side electrode layer 36 and the thickness, porosity and average hole diameter of the diffusion resistor layer 35. While the sensor main body 32 is capable of linearly detecting oxygen concentration, because the temperatures required for activating the sensor main body 32 will be high temperatures above 600° C. and the temperature range for keeping the sensor body 32 active is relatively narrow, it is impossible to control the activation range solely by using the heat of the exhaust gas from the engine 10. Thus, according to the present embodiment, the sensor main body 32 is heated up to an activation temperature range through heat control using the heater 33. Meanwhile, on the other hand, the concentration of unburnt gas such as carbon monoxide (CO) and the like changes substantially linearly relative to changes in air-fuel ratio in the region where the air-fuel ratio is on the rich side with respect to the stoichiometric air-fuel ratio. In this case, the sensor body 32 generates a limit current corresponding to the concentration of CO and the like.

Figure 3:
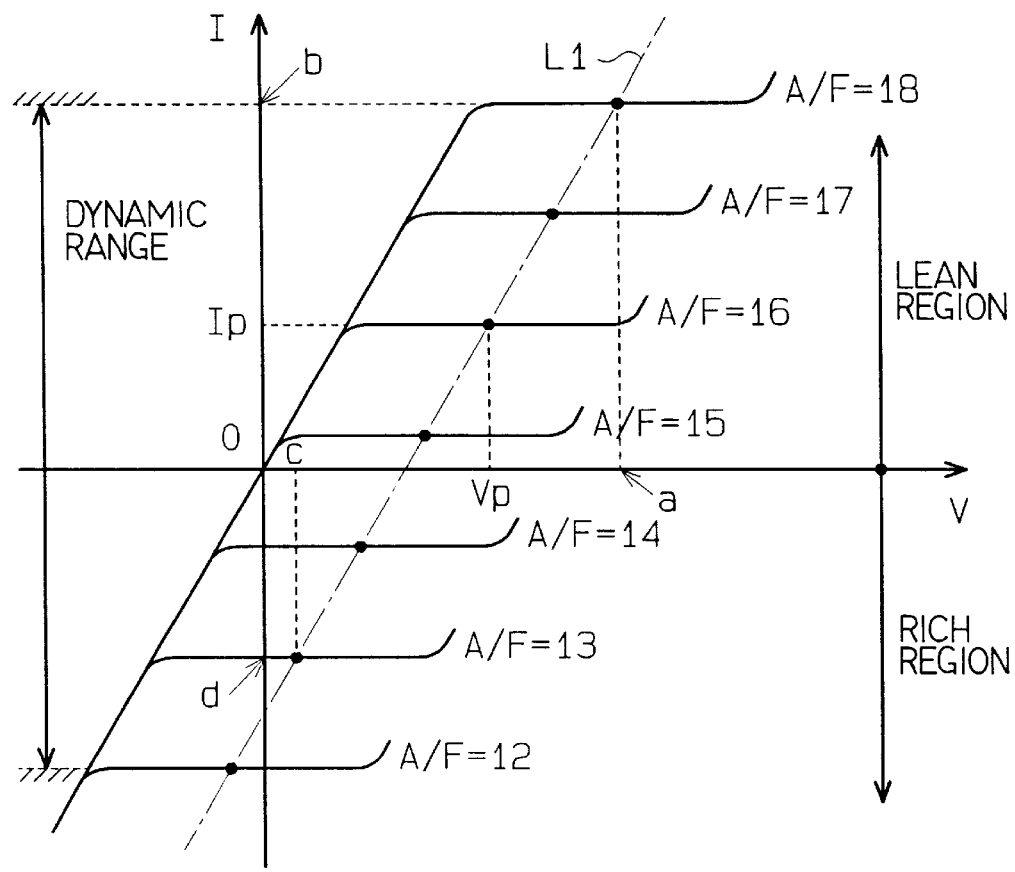
FIG. 3 is a graph showing voltage-current characteristics of the air-fuel ratio sensor.

A voltage-current characteristic of the sensor main body 32 will be described with reference to FIG. 3. As shown in FIG. 3, there is a linear relationship observed between current flowing into the solid electrolytic layer 34 of the sensor main body 32, which is proportional to the air-fuel ratio detected by the A/F ratio sensor 30, and the voltage applied to the solid electrolytic layer 34. In this case, the limit current of the sensor main body 32 is represented by the straight line portions parallel to the voltage axis V. Limit current (sensor current) increases or decreases in proportion to A/F ratio, that is, depending on whether the air-fuel ratio is lean or rich. In other words, the richer the A/F ratio is, the smaller the limit current becomes. Conversely, the leaner the A/F ratio is, the greater the limit current becomes.

Voltage regions below the straight line portion parallel to the voltage axis V in the figure showing the voltage-current characteristics are resistor-dependent regions, in which the gradient of a straight line, e.g. line L1, is determined by the internal resistance of the solid electrolytic layer 34 of the sensor main body 32 (which corresponds to the element resistance). This element resistance changes in proportion to the sensor temperature and thus, the aforementioned gradient decreases due to an increase in element resistance when the temperature of the sensor main body 32 decreases.

On the other hand, as shown in FIG. 1, a bias command signal (digital signal) Vr for applying voltage to the A/F ratio sensor 30 is provided by the microprocessor 20 to a D/A converter 21, converted to an analog signal Vb by the D/A converter 21 and subsequently provided to an LPF (low pass filter) 22. Then, output voltage Vc generated by the LPF 22 by removing high frequency components from the analog signal Vb is provided to the bias control circuit 40. This bias control circuit 40 is designed to apply either a voltage for detecting the A/F ratio or a voltage for detecting the element resistance to the A/F ratio sensor 30. When detecting the A/F ratio, a characteristic line L1 as shown in FIG. 3 is used to set applied voltage Vp in accordance with the corresponding A/F ratio. On the other hand, when detecting the element resistance, a single voltage signal having a predetermined time constant (which represents a predetermined frequency for changing the applied voltage) is applied to the A/F ratio sensor 30.

The bias control circuit 40 has a current detection circuit 50 which detects current that is generated after voltage is applied to the A/F ratio sensor 30. An analog signal indicative of the current value detected by the current detection circuit 50 is provided to the microprocessor 20 via an A/D converter 23. A detailed construction of the bias control circuit 40 will be described later.

A heater control circuit 25 controls operation of the heater 33 that is attached to the A/F ratio sensor 30. Namely, the heater control circuit 25 controls the duty factor of electric power supply to the heater 33 from a battery power source (not shown) in accordance with element temperature of the A/F ratio sensor 30 or heater temperature to control the heating operation of the heater 33.

Figure 4A:
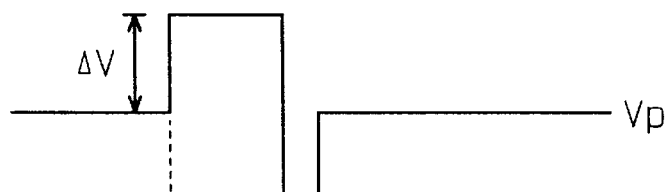
FIGS. 4A and 4B show waveforms of an output voltage of a D/A converter and an output voltage of a low pass filter of the air-fuel ratio detection device.
Figure 4B:
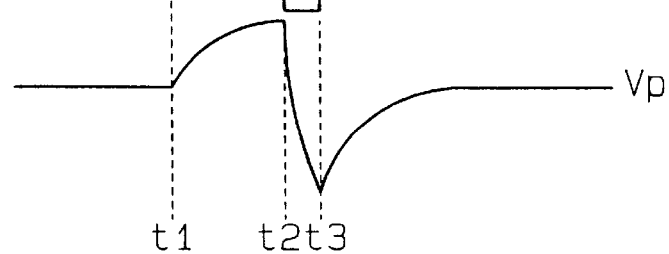

Details of the command voltage applied to the A/F ratio sensor 30 for detecting element resistance will be described hereinafter. The microprocessor 20 generates a digital bias command signal Vr. This bias command signal Vr is converted to a single voltage signal (analog signal) having a predetermined time constant after it passes through the D/A converter 21 and the LPF 22. FIGS. 4A and 4B show examples of signal waveforms of the output voltage Vb from the D/A converter 21 and the output voltage Vc from the LPF 22 when detecting the element resistance. In this case, as shown in FIGS. 4A and 4B, at time t1, output voltage Vb from the D/A converter 21 is switched to a value larger by ΔV than the applied voltage Vp (that is, voltage for detecting the A/F ratio) at time t1. At time t2, the output voltage is switched to a value smaller than the aforementioned applied voltage Vp only for a short period of time that is shorter than the period between t1 and t2. Then, the output voltage vb is returned to its original voltage level Vp at time t3. On the other hand, output signal Vc from the LPF 22 is a signal whose high frequency components are removed by providing a predetermined time constant.

In the present embodiment, a voltage having a predetermined time constant refers to a signal that includes a single frequency component. The determination of such frequency component is described hereinafter.

Figure 5:
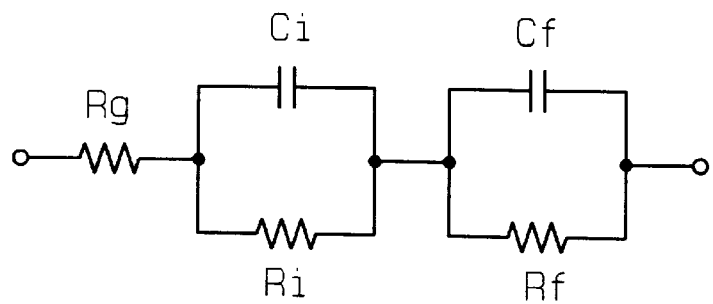
FIG. 5 is a diagram showing an equivalent electrical circuit of the air-fuel ratio sensor.

FIG. 5 shows an equivalent electrical circuit of the A/F ratio sensor 30. In particular, FIG. 5 shows the equivalent electrical circuit of the sensor main body 32. In this circuit, particle resistance of the solid electrolytic layer 34 against oxygen ion is indicated by Rg, particle resistance and intergranular capacitance of the solid electrolytic layer 34 in its granular interface are indicated by Ri and Ci, respectively, and electrode interface resistance and electrode interface capacitance of the platinum electrodes 36 and 37 are indicated by Rf and Cf, respectively.

Figure 6:
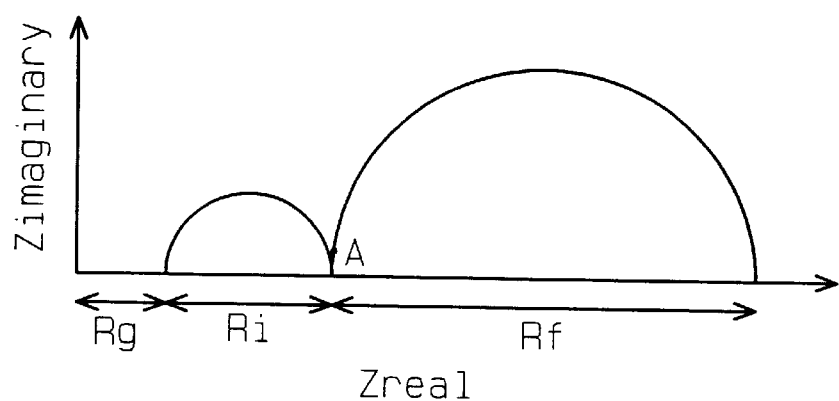
FIG. 6 is a graph showing impedance characteristics of the electric circuit of FIG. 5 with respect to a frequency of AC input voltage.

FIG. 6 shows complex impedance characteristics of the A/F ratio sensor 30 shown in FIG. 5. In this figure, the X axis "Zreal" indicates a real number part of the complex impedance, whereas the Y-axis "Zimaginary" indicates an imaginary number part of the complex impedance. Impedance ZAC is expressed by the following Equation (1).

$$ZAC = Zreal + j \cdot Zimaginary \quad (1)$$

Point A in FIG. 6 indicates impedance characteristics when the applied voltage is changed at a frequency of 1 kHz. When the frequency is lower than 1 KHz, the impedance characteristics are those to the right of point A while a frequency of higher than 1 KHz will have impedance characteristics that are to the left of point A. Namely, when the frequency is close to 1 kHz, the sum of Rg and Ri is detected as the impedance.

Figure 7:
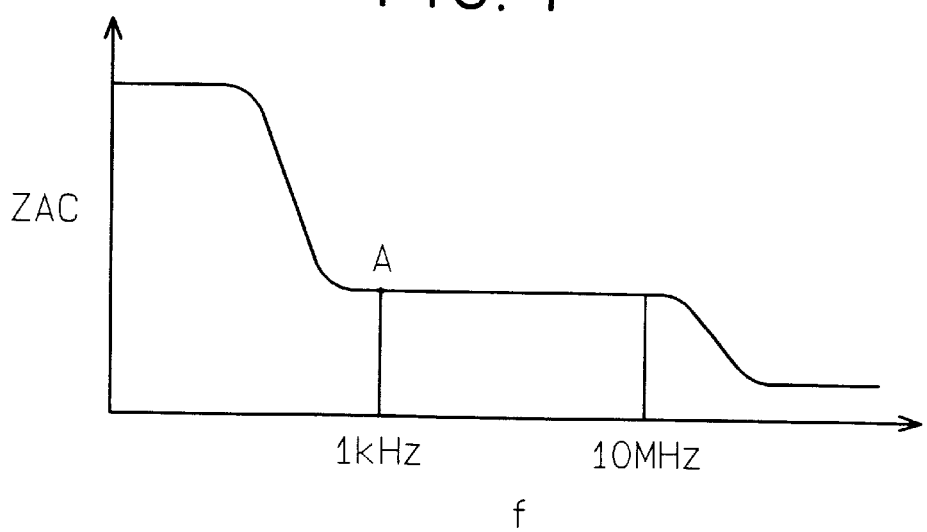
FIG. 7 is a graph showing a relation between the frequency of AC input voltage to the air-fuel ratio sensor and total impedance characteristics of the air-fuel ratio sensor.

FIG. 7 is a modification of FIG. 6, wherein the X axis indicates the frequency and while the Y axis indicates the impedance ZAC. As shown in FIG. 7, the impedance ZAC of the A/F ratio sensor converges to a predetermined value (Rg+Ri) in the frequency range from 1 kHz to 10 MHz. In the range where frequency is higher than 10 MHz, the impedance ZAC furthermore decreases to converge to a predetermined value Rg, which is smaller than (Rg+Ri). Thus, the frequency range of 1 kHz to 10 MHz is most suitable because the impedance ZAC is constant in this range regardless of the frequency f for changing/switching the applied voltage. In the present embodiment, with the frequency set to 1 kHz, the time constant is set to about 159 ms by the LPF 22 to derive the corresponding rising waveform (see time t1–t2 in FIG. 4B). The lower limit of the time constant (that is, the upper limit of frequency) is depends on the processing capacity of the D/A converter 21 or the A/D converter 23. The lower limit of the time constant can be further lowered using circuits of higher speeds.

For such reasons, when changing the voltage to be applied to the A/F ratio sensor 30, the microprocessor 20 generates a digital signal that has frequency components of about 1 kHz. This digital signal is converted to a signal having a predetermined time constant (about 159 ms) after it passes through the D/A converter 21 and the LPF 22. The command signal output from the microprocessor 20 can be generated relatively easily because it has a rectangular shape.

On the other hand, when switching back from voltage for detecting element resistance to the voltage for detecting the A/F ratio, if such switching to the voltage for detecting the A/F ratio is done directly, the sensor current reaches its peak value immediately after such switching due to the influences of electric charges stored in Ci and Cf as described above, thus prolonging the time required for the current to converge to its original value. Accordingly, in the present embodiment, when switching from the voltage for detecting element resistance to the original voltage, which is the voltage for detecting the A/F ratio, voltage that has a polarity opposite that of the previously applied voltage (see t1–t2 in FIG. 4A) is applied for a short period of time (see time t2–t3 in FIG. 4A) in order to completely discharge electric charges in Ci and Cf in a short period of time and further reduce the time for stabilizing the sensor current. In this case, it is desirable to control the voltage so that substantially the same amount of electric charges move within the sensor element when the applied voltage is switched to one side (which may be towards the positive side or the negative side) and when such applied voltage is subsequently switched to the other side. For this purpose, when switching the applied voltage, the applied voltage may have positive side and negative side waveforms that are symmetrical with each other.

Figure 8:
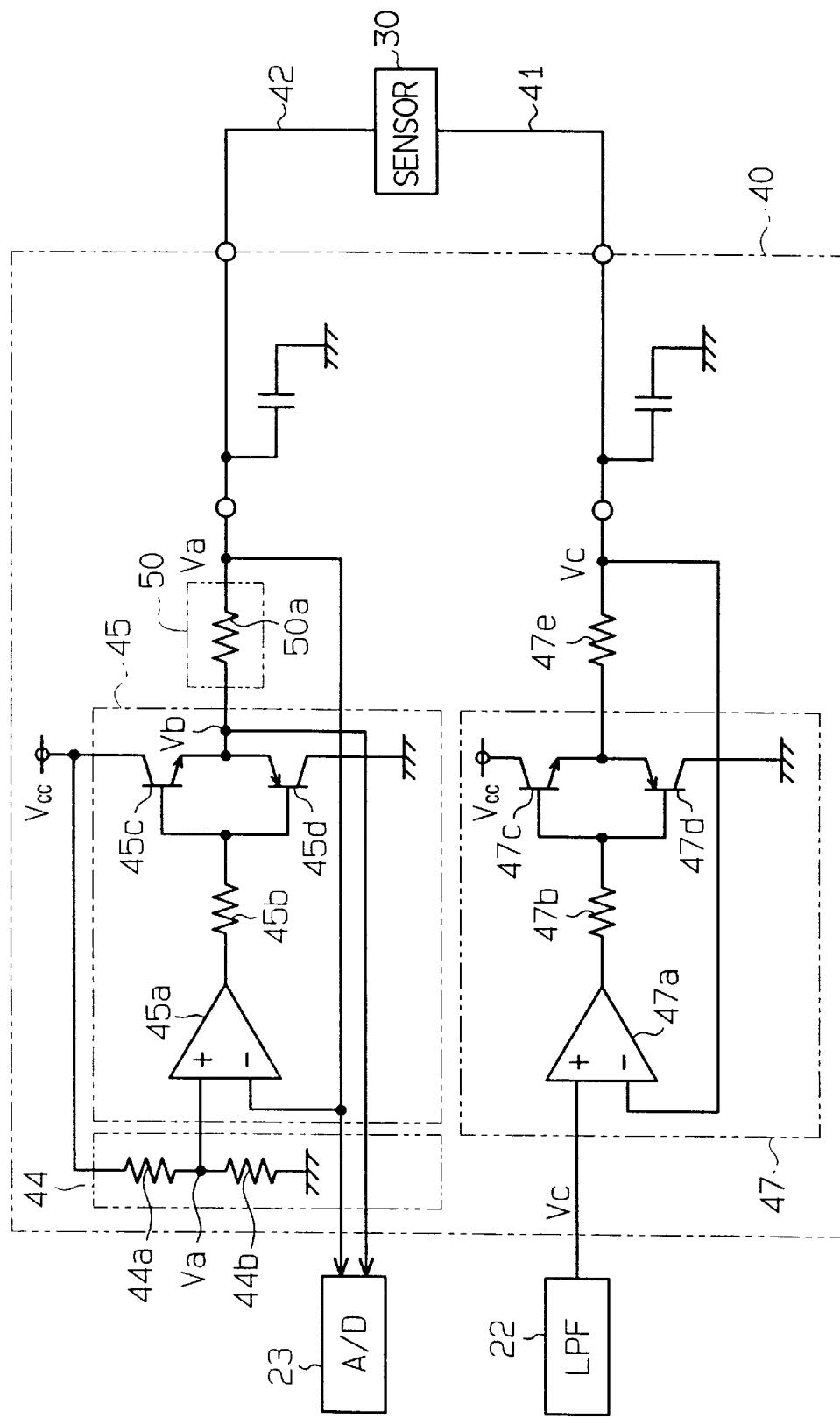
FIG. 8 is a circuit diagram showing a construction of a bias control circuit according to the first embodiment.

The construction of the bias control circuit 40 will be described next with reference to an electric circuit diagram shown in FIG. 8. As shown in FIG. 8, the bias control circuit 40 mainly includes a reference voltage circuit 44, a first voltage supply circuit 45, a second voltage supply circuit 47 and a current detection circuit 50. The reference voltage circuit 44 divides constant voltage Vcc by means of voltage dividing resistors 44*a*, 44*b* to generate a constant reference voltage Va.

The first voltage supply circuit 45 is made up of a voltage follower circuit. This first voltage supply circuit 45 supplies a voltage equal to the reference voltage Va of the reference voltage circuit 44 to a terminal 42 of the A/F ratio sensor 30 (this terminal 42 is connected to the atmosphere side electrode layer 37 shown in FIG. 2). More concretely, the first voltage supply circuit 45 includes an operational amplifier 45*a* whose non-inverting input terminal is connected to a voltage division point between the voltage dividing resistors 44*a* and 44*b* and whose inverting input terminal is connected to one terminal 42 of the A/F ratio sensor 30, a resistor 45*b* which has one end connected to an output terminal of the operational amplifier 45*a*, NPN transistor 45*c* and PNP transistors 45*d*. The bases of the NPN transistor 45*c* and the PNP transistor 45*d* are connected to the other end of the resistor 45*b*. A collector of the NPN transistor 45*c* is connected to the source of constant voltage Vcc and an emitter thereof is connected to one terminal of the A/F ratio sensor 30 via a current detection resistor 50*a*. This current detection resistor 50*a* forms the current detection circuit 50. An emitter of the PNP transistor 45*d* is connected to the emitter of the NPN transistor 45*c* while a collector of the same PNP transistor 45*d* is connected to ground.

The second voltage supply circuit 47 is also made up of a voltage follower circuit. This second voltage supply circuit 47 supplies a voltage equal to the output voltage Vc from the LPF 22 to the other terminal 41 of the A/F ratio sensor 30 (the terminal 41 is connected to the exhaust gas side electrode layer 36 shown in FIG. 2). More concretely, the second voltage supply circuit 47 includes an operational amplifier 47*a* whose non-inverting input terminal is connected to the output terminal of the LPF 22 and whose inverting input terminal is connected to the other terminal 41 of the A/F ratio sensor 30, a resistor 47*b* which has one end connected to an output terminal of the operational amplifier 47a, an NPN transistor 47c and a PNP transistors 47d. The bases of the NPN transistor 47c and the PNP transistor 47d are both connected to the other end of the resistor 47b. A collector of the NPN transistor 47c is connected to receive constant voltage Vcc and an emitter of the same transistor 47c is connected to the other terminal of the A/F ratio sensor 30. An emitter of the PNP transistor 47d is connected to the emitter of the NPN transistor 47c while a collector of the same transistor 47c is connected to ground.

With the above-described construction, one terminal 42 of the A/F ratio sensor 30 is always supplied with the constant voltage Va. If the voltage Vc, which is lower than the constant voltage Va, is supplied to the other terminal 41 of the A/F ratio sensor 30 via the LPF 22, the A/F ratio sensor 30 is positively biased. If a voltage Vc higher than the constant voltage Va is supplied to the other terminal of the A/F ratio sensor 30 via the LPF 22, the A/F ratio sensor 30 is negatively biased.

Figure 9:
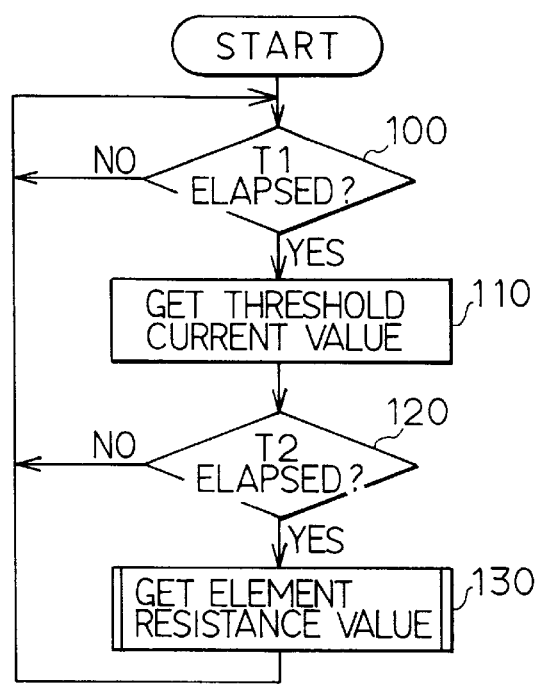
FIG. 9 is a flow chart showing a main routine executed by a microprocessor of the air-fuel ratio detection device of the first embodiment.

Hereinafter, the operation of the air-fuel ratio detection device, which has the construction described above, will be explained. FIG. 9 is a flow chart showing a control procedure according to the present embodiment. This control procedure is performed upon start of power supply to the microprocessor 20. As shown in FIG. 9, in step 100, the microprocessor 20 determines whether a predetermined time T1 has elapsed after the last detection operation of the A/F ratio. The predetermined time T1 corresponds to the frequency for detecting the A/F ratio. T1 is preferably set to, for example, 2–4 ms. If the predetermined time T1 has elapsed after the last detection of the A/F ratio, the microprocessor 20 gives a positive output in step 100 and control goes to step 110. In step 110, the microprocessor 20 retrieves sensor current Ip (limit current value) detected by the current detection circuit 50 and determines a corresponding value of the A/F ratio of the engine 10 that corresponds to the sensor current Ip using a predefined characteristics map. Using the characteristic line L1 shown in FIG. 3, the microprocessor 20 applies a voltage Vp that corresponds to the detected A/F ratio to the A/F ratio sensor 30.

Furthermore, in step 120, the microprocessor 20 determines whether a predetermined time T2 has elapsed after the last detection of the element resistance. The predetermined time T2 corresponds to the frequency of detecting the element resistance. This predetermined time is selectively set in accordance with, for example, the operating condition of the engine 10. In this embodiment, normally, when there is a relatively small change in the A/F ratio (i.e., the engine operating condition is normal), the predetermined time T2 is set to 2 s. On the other hand, when there is an abrupt change in the A/F ratio (i.e., the engine operating condition is in a transitional state), the time T2 is set to 128 ms. If the microprocessor 20 gives a negative determination in step 120, the A/F ratio is detected every time the predetermined time T1 lapses as described above. If the microprocessor 20 gives a positive output in step 120, step 130 subsequently detects the element resistance.

Figure 10:
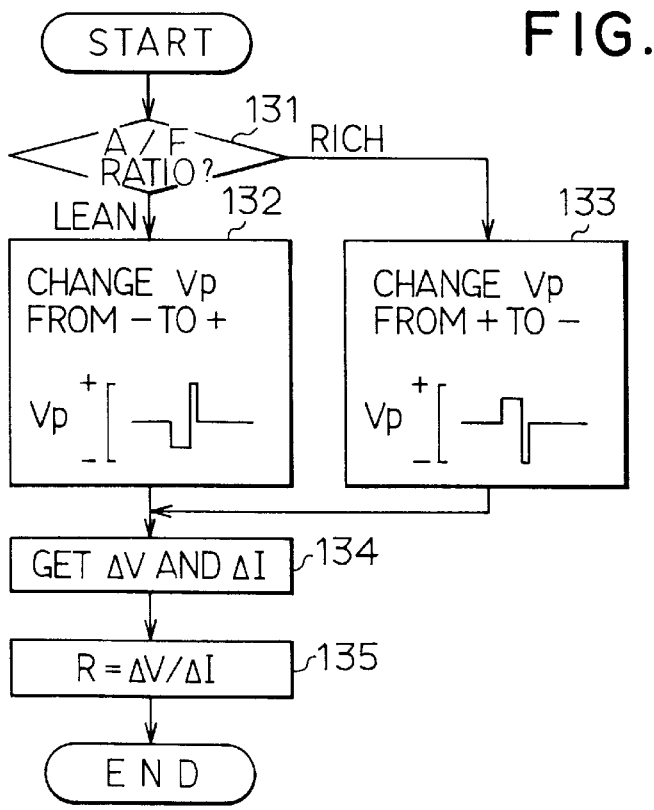
FIG. 10 is a flow chart showing an element resistance detection subroutine executed by the microprocessor according to the first embodiment.

A procedure for detecting element resistance will be described with reference to a subroutine shown in FIG. 10. As shown in FIG. 10, the microprocessor 20 determines in step 131 whether the current A/F ratio is rich or lean. If the A/F ratio is lean, the microprocessor 20 switches the applied voltage Vp (i.e., the A/F ratio detection voltage) from the negative to positive sides in step 132. If the A/F ratio is rich, the applied voltage Vp is changed from the positive to the negative side (bias command signal Vr is manipulated) in step 133.

Then, after switching the applied voltage, the microprocessor 20 retrieves the amount of voltage change ΔV and the amount of sensor current change ΔI detected by the current detection circuit 50 in step 134. In subsequent step 135, the microprocessor 20 calculates the element resistance R from ΔV and ΔI (R=ΔV/ΔI). After step 135, controls returns to the original main routine.

FIGS. 11A–11D show waveforms of voltages applied to the A/F ratio sensor 30 (output voltage Vc after passing through the LPF 22) and waveforms of the sensor current that flows with the application of such voltage. Namely, if the A/F ratio is lean (for example, if the A/F ratio is equal to 18), as shown in FIGS. 11A and 11B, voltage applied to the A/F ratio sensor 30 is switched to the negative side by a voltage amount ΔV, and a corresponding current change ΔI in the amount of current towards the negative side is detected. Applied voltage a[V] and sensor current b[A] as shown in FIGS. 11A and 11B correspond to points a, b, respectively, in FIG. 3. On the other hand, if the A/F ratio is rich (for example, the A/F ratio is equal to 13), as shown in FIGS. 11C and 11D, the voltage applied to the A/F ratio sensor 30 is switched to the positive side by the voltage amount ΔV and a corresponding current change ΔI in the amount of current towards the positive side is detected. Applied voltage c and sensor current d as shown in FIGS. 11C and 11D correspond to points c, d, respectively, of FIG. 3.

In this case, because sensor current is obtained based on a voltage change to the negative side when the A/F ratio is lean and based a voltage change to the positive side when the A/F ratio is rich, the sensor current never exceeds the dynamic range (see FIG. 3) of the current detection circuit 50.

Figure 12:
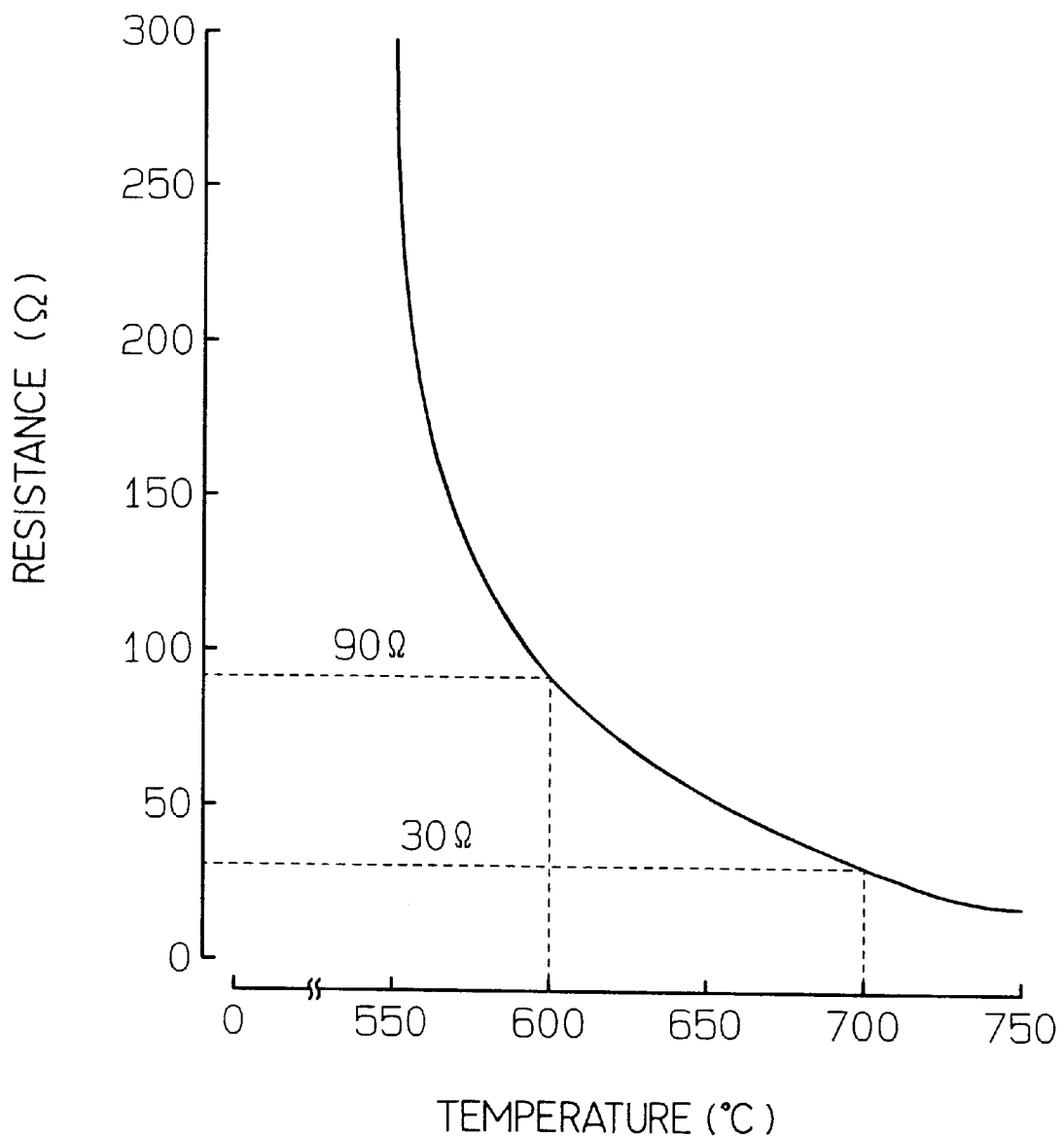
FIG. 12 is a graph showing a relation between an element temperature and an element resistance of the air-fuel ratio sensor.

On the other hand, as shown in FIG. 12, there is a predetermined relationship between the sensor element resistance R, which can be obtained as described above, and the sensor element temperature. That is, as the element temperature decreases, the element resistance R increases remarkably. As shown in the same figure, an element resistance R of 90 Ω corresponds to an element temperature of 600° C., which is a temperature at which the A/F ratio sensor 30 is activated to some extent, while an element resistance R of 30 Ω corresponds to an element temperature of 700° C., which is a temperature at which the A/F ratio sensor 30 is fully activated. When executing the heater control, the amount of power supply to the heater 33 for eliminating a difference between the calculated element resistance R and a target resistance value (e.g., 30 Ω) at which the A/F ratio sensor 30 is fully activated is calculated and used for controlling the duty factor of the power supply to the heater 33. In other words, feed back control based on the element temperature is performed.

The advantages offered by the foregoing embodiment are enumerated below.

(a) In the present embodiment, voltage applied to the A/F ratio sensor 30 for detecting the A/F ratio is changed to the voltage for detecting the sensor element resistance of the A/F ratio sensor 30 by setting a predetermined time constant for such voltage change, and the element resistance of the sensor element of the A/F ratio sensor 30 is determined from the voltage change and a current change due to the voltage change. Therefore, with the oxygen concentration sensor according to the present embodiment, steep rise in the current during the switching of the applied voltage to the voltage for detecting the element resistance, which is a problem observed in prior art, can be prevented. Consequently, sensor current values can be measured precisely which allows highly accurate detection of the element resistance of the A/F ratio sensor 30. In this case, because element resistance is detected by a single AC voltage wave which is applied during the process of detecting A/F ratio, the time required for detecting the element resistance is shortened. Furthermore, the A/F ratio detection accuracy is unaffected and remains at a considerably high level even when the engine is in its transitional operation.

(b) In the present embodiment, the time constant mentioned above is set to a value (less than 159 ms) that sets the cutoff frequency for switching the voltage for detecting element resistance to 1 kHz. Accordingly, frequency characteristics of the A/F ratio sensor 30 will be stable as shown in FIG. 7. To further stabilize the impedance characteristics, it is desirable to limit the time constant to be within a range of 32 to 53 ms (which corresponds to the frequency range from 3 kHz to 5 kHz).

(c) In the present embodiment, the LPF 22 is used to apply an AC signal having a predetermined time constant to the A/F ratio sensor 30. Consequently, it is possible to achieve the desired purpose with a much simpler construction. In this case, the microprocessor 20 only needs to produce digital signals and does not need to perform any high-level computational operations. Thus, it is possible to provide an air-fuel ratio detection device which can be readily implemented.

(d) Furthermore, according to the construction of the present embodiment, element resistance is detected from a current change induced by the application of voltage to the negative side when the A/F ratio is lean. On the other hand, element resistance is detected from a current change induced by the application of voltage to the positive side when the A/F ratio is rich. In this case, element resistance is detected by using a current change which is directed towards the inner side of the dynamic range set beforehand for the current detection circuit 50. Thus, deterioration in the detection precision due to current changes that are out of the dynamic range can be prevented. Furthermore, another advantageous effect will be the ability to keep the dynamic range at a minimum (the dynamic range can be set within a narrow range to ensure a high degree of detection accuracy of the current detection circuit 50).

(e) The voltage waveform is set so that substantially the same amount of electric charges move inside the sensor element when the voltage applied to the A/F ratio sensor 30 is a positive voltage and when the same amount of negative voltage is applied. Thus, the convergence of sensor current after finishing the detection of element resistance can be accelerated.

(f) If the element resistance can be detected very accurately as described above, it is also possible to enhance precision in controlling the actuation of the A/F ratio sensor 30 (control of power supply to the heater 33) using the detected element resistance. In addition, the detected element resistance may also be used effectively in evaluating the deterioration in the functions of the sensor.

Figure 13A:
FIGS. 13A–13D, 14A–14D and 15A–15D are graphs showing other variations of changes in voltage applied to the air-fuel ratio sensor and respective current changes due to such voltage changes.
Figure 13B:
Figure 13C:
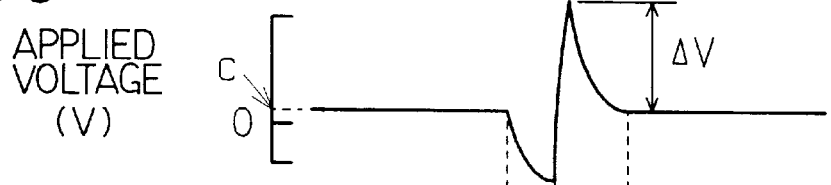
Figure 13D:
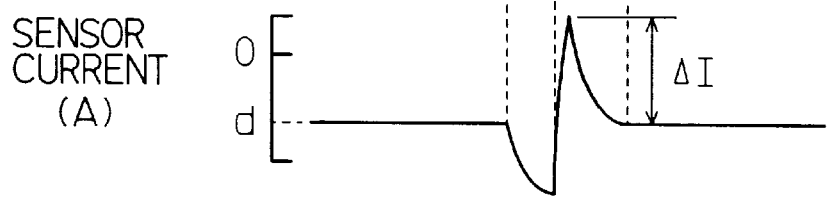

The switching of the applied voltage in detecting element resistance can be modified as shown in FIGS. 13A–15D. According to the variation shown in FIGS. 13A–13D, voltage applied for detecting the element resistance is switched to both positive and negative voltages as in the above-described embodiment. However, in this variation, the voltage change amount $\Delta V$ and the current change amount $\Delta I$ are measured based on the second waveform and not the first waveform as shown in FIGS. 11A–11D. As shown in FIGS. 13A and 13B, when the A/F ratio is lean (e.g., the A/F ratio is 18), the voltage is changed from positive to negative voltages with respect to the voltage applied immediately before (that is, the voltage for detecting the A/F ratio) and the element resistance is calculated from negative voltage change amount $\Delta V$ and the negative current change amount $\Delta I$. On the other hand, as shown in FIGS. 13C and 13D, when the A/F ratio is rich (e.g., the A/F ratio is 13), voltage is switched from the negative to positive voltages with respect to the voltage applied immediately before, and element resistance is calculated from the positive voltage change amount $\Delta V$ and the positive current change amount $\Delta I$.

Figure 14A:
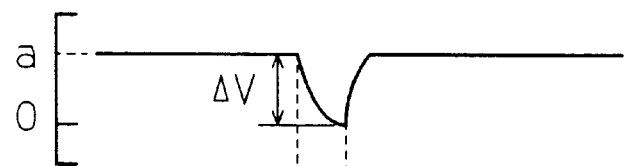
Figure 14B:
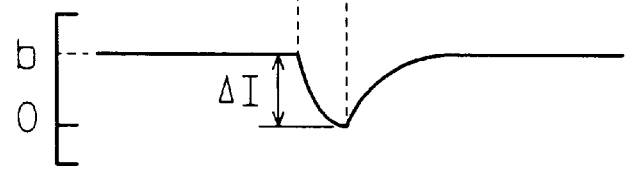
Figure 14C:
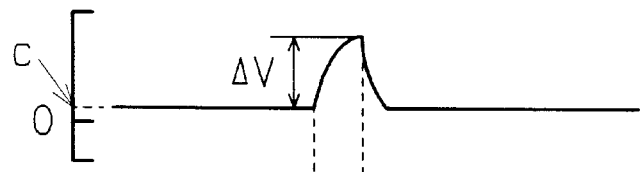
Figure 14D:
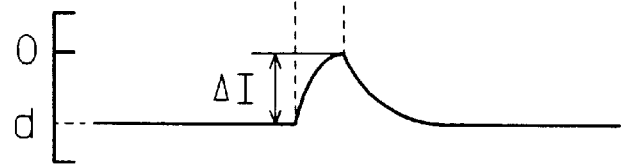
Figure 15A:
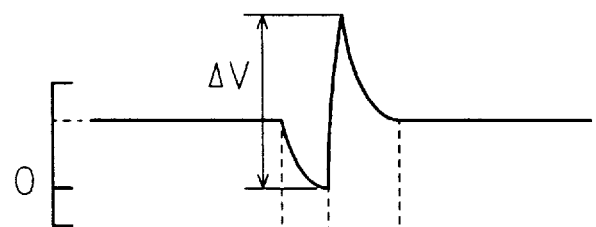
Figure 15B:
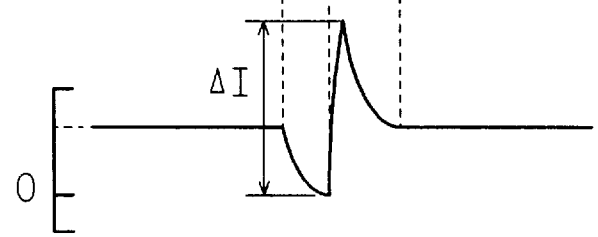
Figure 15C:
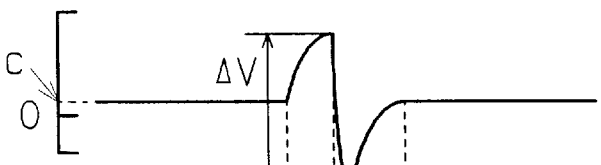
Figure 15D:
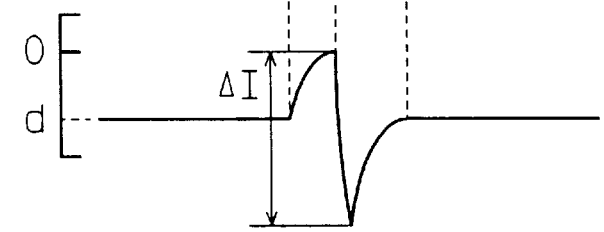

Furthermore, in the variation shown in FIGS. 14A–14D, the applied voltage is changed to only one side, namely, either to become a positive or a negative voltage. Then, voltage change amount $\Delta V$ and current change amount $\Delta I$ are measured. As shown in FIGS. 14A and 14B, as in the respective embodiments above, the applied voltage is set to a negative voltage and the element resistance is determined based on the amount of current change and the amount of voltage change amount when the A/F ratio is lean. On the other hand, as shown in FIGS. 14C and 14D, the applied voltage is set to a positive voltage and the element resistance is determined based on the amount of current change and the amount of voltage change when the A/F ratio is rich. Although the time required for sensor current to converge to its original limit current level is prolonged in this case, the precision for detecting the element resistance remains unaffected.

In the variations shown in FIGS. 13A–14D, as in the foregoing first embodiment, the negative sensor current change is measured when the A/F ratio is lean, whereas the positive sensor current change is measured when the A/F ratio is rich. Thus, the sensor current can be measured precisely within the dynamic range of the current detection circuit 50. Furthermore, the dynamic range of the current detection circuit 50 can be initially set to a minimum.

Furthermore, in another variation shown in FIGS. 15A–15D, the applied voltage is set to both the positive and negative voltages and the voltage change amount $\Delta V$ and the current change amount $\Delta I$ are measured in accordance with a difference between the maximum and minimum values obtained at the time of the voltage change. In this case, although element resistance can be detected most precisely compared to the other cases, a relatively large dynamic range has to be set for the current detection circuit 50. In this case, applied voltage may be changed first either to the positive or to the negative voltage regardless of the value of the A/F ratio, that is, either the embodiment shown in FIG. 15A or FIG. 15C may be adopted.

Hereinafter, the second to the sixth embodiments of the present invention will be described. Explanation of parts or the like that are identical to those of the first embodiment will be omitted here. Therefore, the following description will focus only on differences with the first embodiment.

Figure 17:
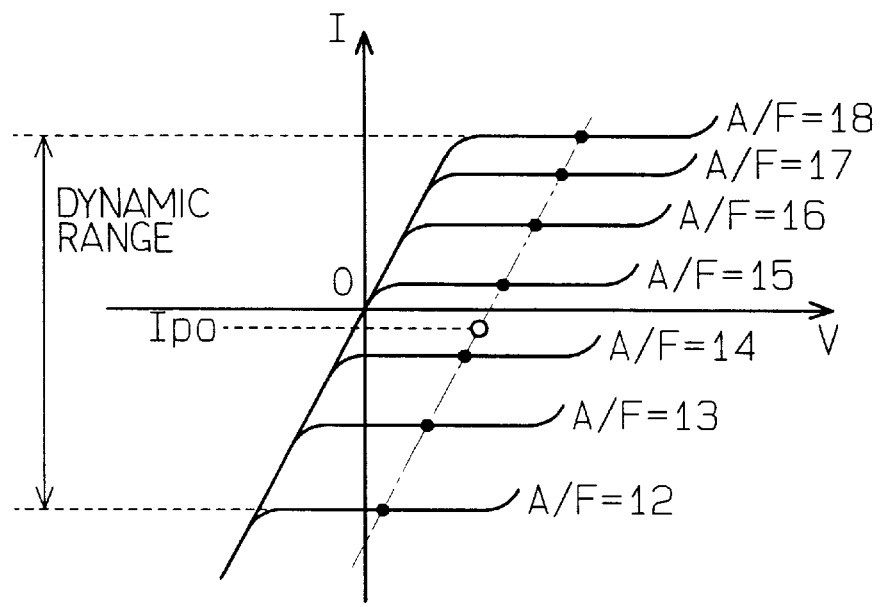
FIG. 17 is a graph showing a relation between voltage-current characteristics of the air-fuel ratio sensor and its dynamic range.
Figure 18:
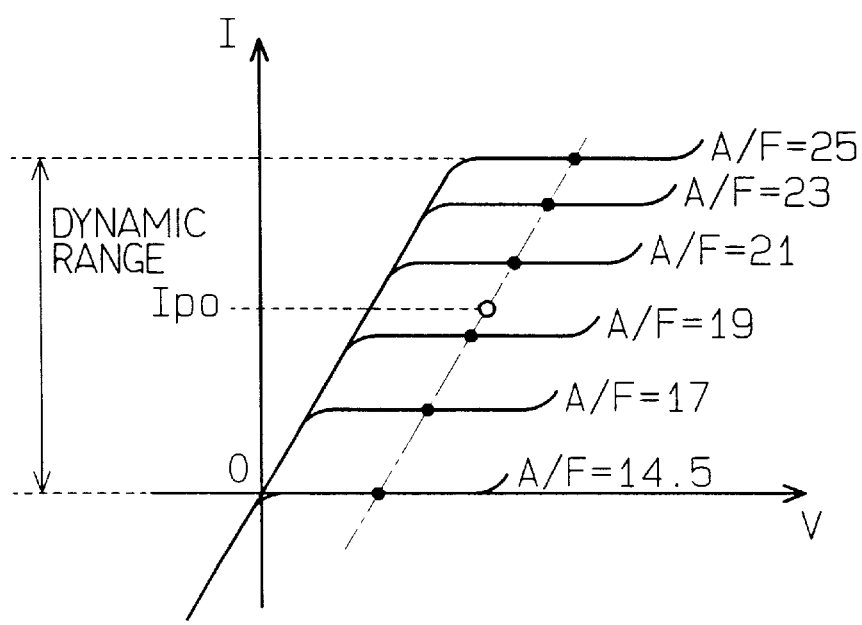
FIG. 18 is a graph showing a relation between voltage-current characteristics of the air-fuel ratio sensor and its dynamic range that is set only for the lean region.

Hereinafter, a second embodiment will be described with reference to FIGS. 16 through 18. As described in the first embodiment, the element resistance is detected unconditionally in accordance with a current change induced by the application of negative voltage when the A/F ratio is lean and current change induced by applying positive voltage when the A/F ratio is rich. However, the predefined dynamic range of the current detection circuit 50 is not always determined with respect to the stoichiometric A/F ratio (that is, the ideal A/F ratio). Accordingly, in the present embodiment, the order of switching the applied voltage to become positive and negative voltages is determined based on a predetermined current value within the dynamic range that is acting as the reference value.

Figure 16:
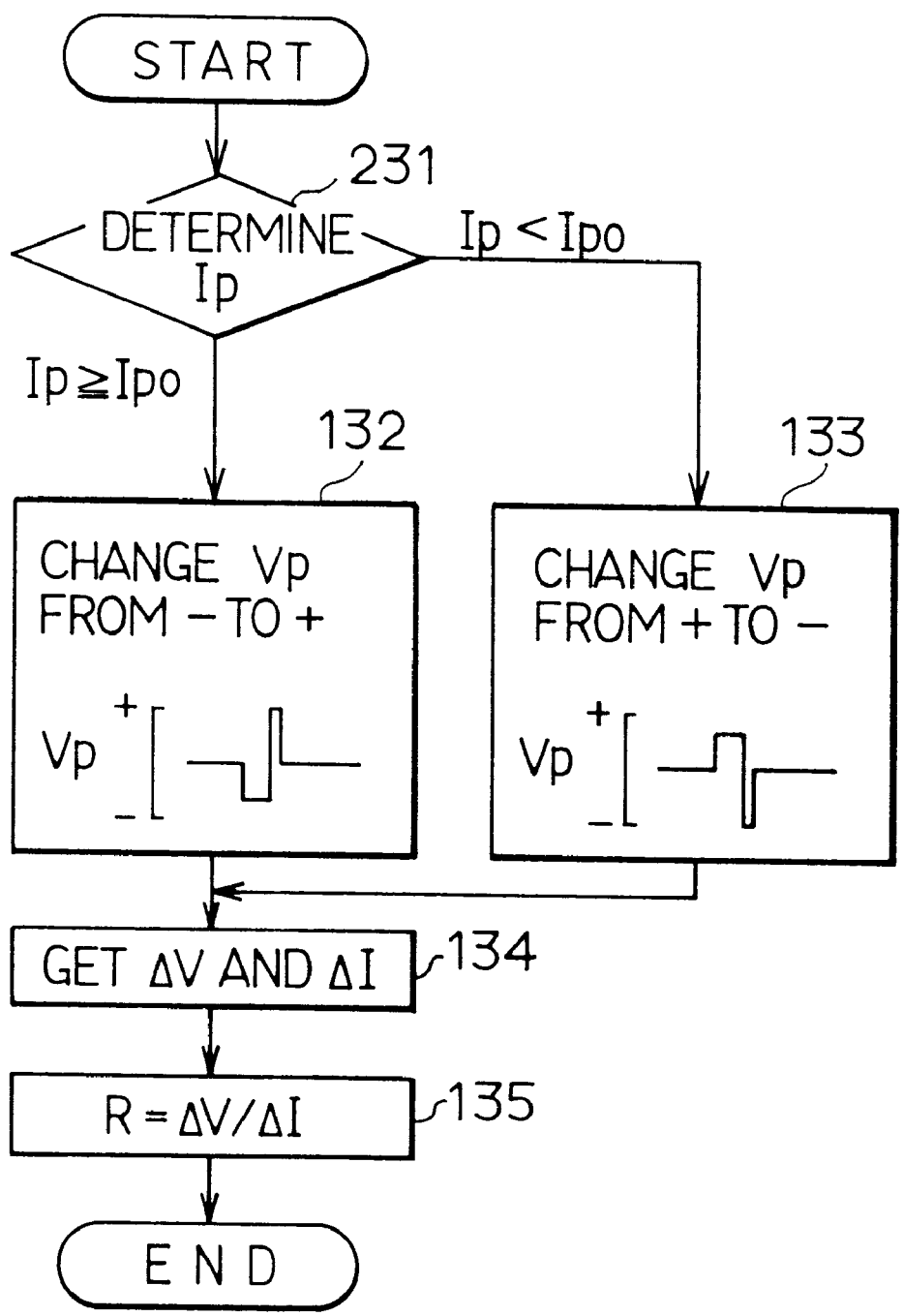
FIG. 16 is a flow chart showing the element resistance detection subroutine according to a second embodiment of the present invention.

FIG. 16 is a flow chart showing a subroutine for detecting element resistance according to the present embodiment. This flow chart is a modification of the flow chart shown in FIG. 10 of the first embodiment. Namely, in the flow chart of FIG. 16, step 131 of FIG. 10 is replaced by step 231. To put it more concretely, in step 231, the microprocessor 20 compares the sensor current (limit current) Ip detected in step 110 of FIG. 9 with a predetermined reference Ipo set within the dynamic range. In this process, if Ip≧Ipo, the microprocessor 20 proceeds to perform step 132 which switches the applied voltage Vp first to a negative voltage and then to a positive voltage. If Ip<Ipo, the microprocessor 20 proceeds to step 133 which changes the applied voltage first to a positive voltage and then to a negative voltage. The other steps are the same as those of the flow chart of FIG. 10 and thus, these steps will not be explained here.

Here, the reference Ipo may be set to be around the vicinity of a central value of the dynamic range. For example, the reference Ipo may be set as shown in FIGS. 17 and 18. If the dynamic range is set so that the A/F ratio can be detected over a range ranging from the rich to the lean region as shown in FIG. 17, the reference value Ipo becomes close to 0 (in the vicinity of the stoichiometric value). On the other hand, if the dynamic range is set so that the A/F ratio is detected only over the lean range as shown in FIG. 18, the reference value Ipo may be set to a few mA which corresponds to an A/F ratio of about 20.

According to the second embodiment, output current Ip of the A/F ratio sensor 30 can always be detected without deviating from the dynamic range and thus, the element resistance R can be detected precisely. In this case, even if the dynamic range is not set with respect to the stoichiometric point (as in the case of FIG. 18), there will be no decline in the accuracy of detecting the element resistance R.

A third embodiment of the present invention will be described with reference to FIGS. 19–20B.

In the foregoing embodiments, the applied voltage Vp for detecting element resistance is changed by attaching a predetermined time constant thereto. However, in the foregoing embodiments, the magnitude of the voltage change ΔV is fixed (U.S. Pat. No. 4,419,190 makes mention of only an upper limit value of the voltage change ΔV). Thus, when the element temperature of the A/F ratio sensor 30 drops or the like, if voltage change ΔV is maintained at a fixed value, the amount of current change ΔI becomes small. Accordingly, errors in detecting the element resistance R are likely to occur which can lead to deterioration in the element resistance detection precision.

Figure 20A:
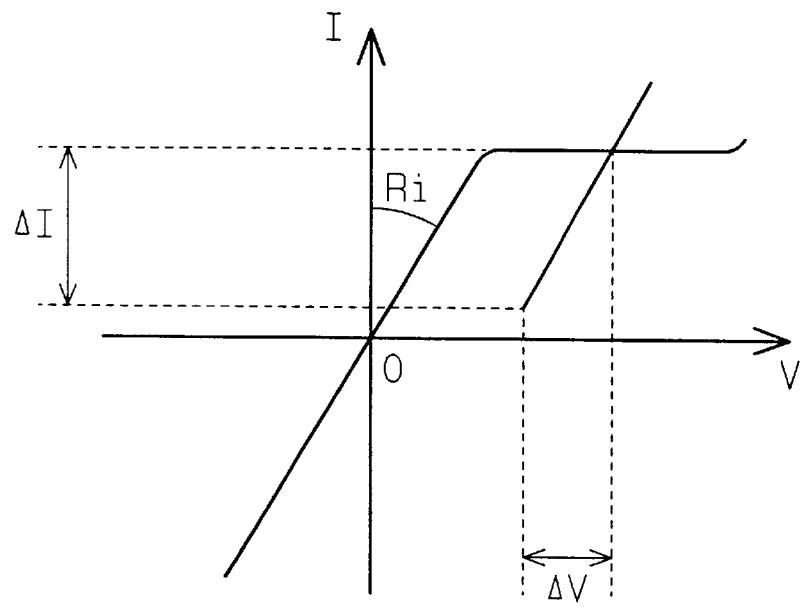
FIGS. 20A and 20B are graphs of voltage-current characteristics of air-fuel ratio sensors having different element temperatures.

The reason for this will be explained with reference to FIGS. 20A and 20B. FIG. 20A shows voltage-current characteristics when the element temperature of the A/F ratio sensor 30 is relatively high (i.e., the element temperature is about 700° C.). FIG. 20B shows voltage-current characteristics when the element temperature is relatively low (i.e., the element temperature is about 600° C.).

Comparing FIGS. 20A and 20B, the slope of a primary linear portion in a resistance-dependent region of FIG. 20B (a voltage region which is below the linear portion parallel to the voltage axis V) is smaller than the slope of the primary linear portion of the resistance-dependent region of FIG. 20A. This means that the internal element resistance (Ri as indicated in both FIGS. 20A and 20B) of the sensor element of FIG. 20B is bigger than the internal element resistance of the sensor element of FIG. 20A. Thus, if the applied voltage to both sensor elements of FIGS. 20A and 20B are subjected to the same amount of voltage change, a current change ΔI' for the sensor element of FIG. 20B will be only half of the current change ΔI of the sensor element of FIG. 20A. In this way, errors in detecting the output current are likely to occur which may lead to erroneous detection of the element resistance.

Accordingly, this embodiment varies the magnitude of the voltage change ΔV based on the element resistance R in order to ensure that the same level of current output obtained when element temperature is high can also be obtained even if the element temperature is low (that is, when the internal resistance Ri is large). In FIG. 20B, the current change ΔI can be obtained by setting the amount of voltage change to ΔV' (ΔV'>ΔV).

Figure 19:
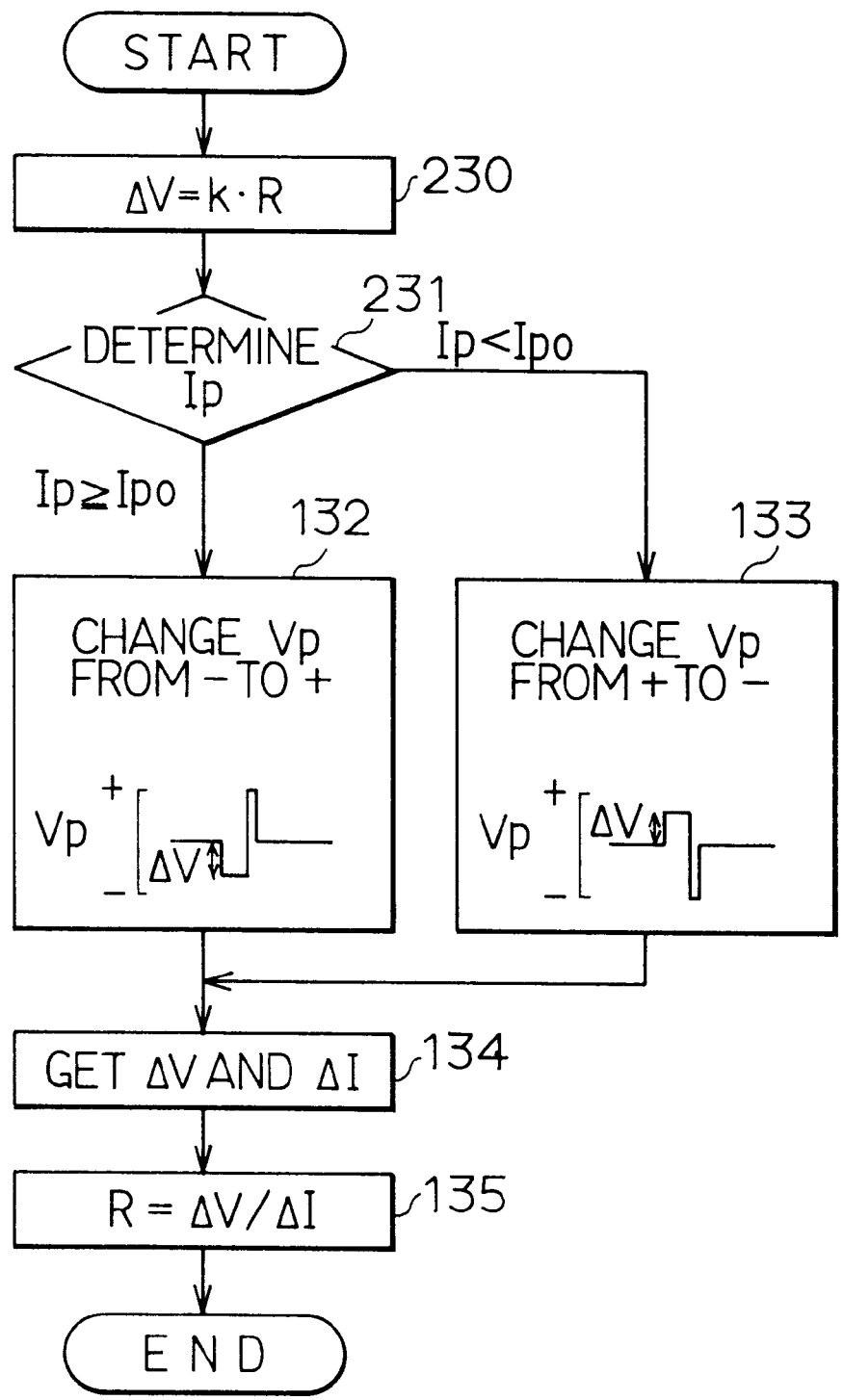
FIG. 19 is a flow chart of the element resistance detection subroutine according to a third embodiment of the present invention.
Figure 20B:
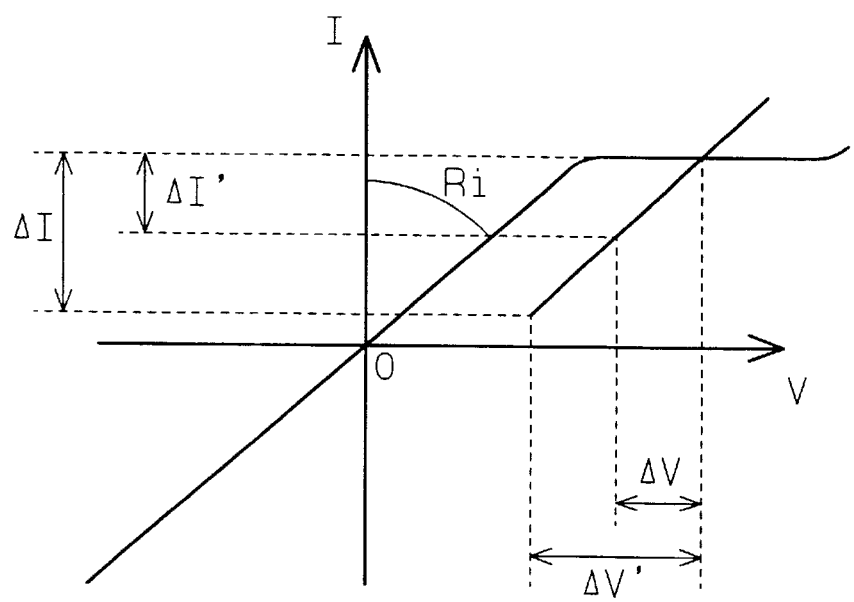

FIG. 19 is a flow chart showing an element resistance detection subroutine according to the present embodiment. This flow chart is a partial modification of the flow chart of the second embodiment shown in FIG. 16. That is, step 230 has been added here. Referring to the flow chart as shown in FIG. 19, in step 230, the microprocessor 20 first multiplies a predetermined proportional coefficient k by the element resistance R detected during the previous processing to obtain the voltage change ΔV (that is, ΔV=k·R). Then, steps 132 and 133 change the voltage Vp based on the voltage change ΔV calculated in step 230. The processes of steps 231 and 132 through 135 of FIG. 19 are the same as those already described before and thus, these steps will not be explained here.

Proportional coefficient k is a constant that is determined beforehand according to the following concept. It may be preferable to increase proportional coefficient k to improve the precision in detecting the element resistance R. However, ΔI cannot be detected precisely if it exceeds the dynamic range of the current detection circuit 50. That is, ΔI must not exceed half the width of the dynamic range. Preferably, ΔI is set to be about one-fourth of width of the dynamic range.

According to the third embodiment of the present invention, the voltage change ΔV for detecting element resistance is set so that it increases as the aforementioned element resistance R increases. Thus, even if the element temperature is low (i.e., the element internal resistance is large), for example, the amount of current change ΔI is not reduced drastically and thus, deterioration in the precision of detecting the element resistance R is prevented.

Hereinafter, a fourth embodiment will be described with reference to FIGS. 21A through 29. In the foregoing embodiments described above, the bias command signal Vr for applying voltage to the A/F ratio sensor 30 is always passed through the D/A converter 21 and the LPF 22. As explained above, the time constant of the LPF 22 is appropriately set for measuring the internal resistance of the sensor element. However, there might be considerable errors during the detection of the A/F ratio if the time constant of the LPF 22 is used as is for detecting the A/F ratio. The reason for this will be explained with reference to FIGS. 21A and 21B.

Figure 21A:
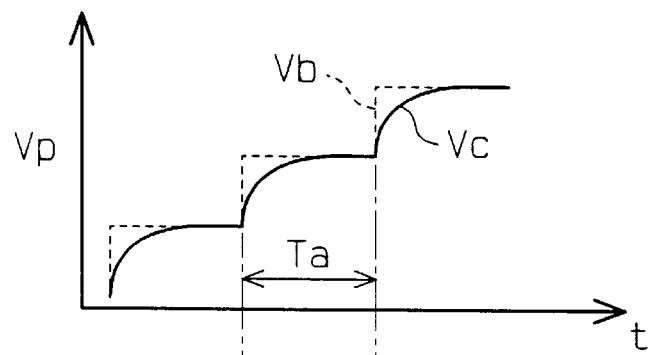
FIGS. 21A and 21B are graphs showing a relation between applied voltage to the air-fuel ratio sensor and sensor current of the air-fuel ratio sensor.
Figure 21B:
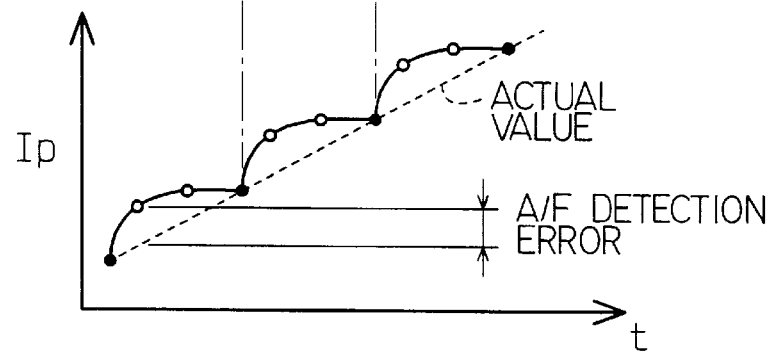

FIGS. 21A and 21B show changes in the applied voltage Vp and sensor current Ip during the detection of the A/F ratio. As shown in FIGS. 21A and 21B, the A/F ratio changes from the rich to the lean side. That is, the values of the Vp, Ip move along the straight line (characteristic line) L1 shown in FIG. 3 upward to the right following a limit current range. Applied voltage Vp gradually increases every time Ta as shown in FIG. 21A. In FIG. 21A, the output voltage Vb of the D/A converter 21 shown in FIG. 1 is denoted by broken lines, while the output voltage Vc of the LPF 22, that is, voltage directly applied to the A/F ratio sensor 30, is denoted by a solid line. In this case, in FIG. 21B, the sensor current Ip deviates from and becomes larger than the true value of the limit current indicated by the broken lines. This deviation is due to frequency characteristics of the A/F ratio sensor 30 explained with reference to FIGS. 5, 6 and 7. An amount of the deviation is determined based on the time constant of the LPF 22.

With the change in the A/F ratio, when detecting the sensor current Ip immediately after switching the applied voltage Vp, that is, at the points indicated by ● as shown in FIG. 21B, there will be no detection error because sensor current Ip is in the vicinity of the true value of the limit current. However, if the A/F ratio is detected at shorter intervals than the time Tain which applied voltage Vp is changed, the sensor current Ip will have values indicated by ○ in FIG. 21B which deviate from the true values. As a result, there will be errors in the detection of the A/F ratio.

According to the present embodiment which has been made in consideration of the above problem, when detecting the A/F ratio, the error produced in detecting the A/F ratio shown in FIG. 21B is minimized by switching to another LPF whose time constant is larger than the LPF used for detecting the element resistance.

Figure 22A:
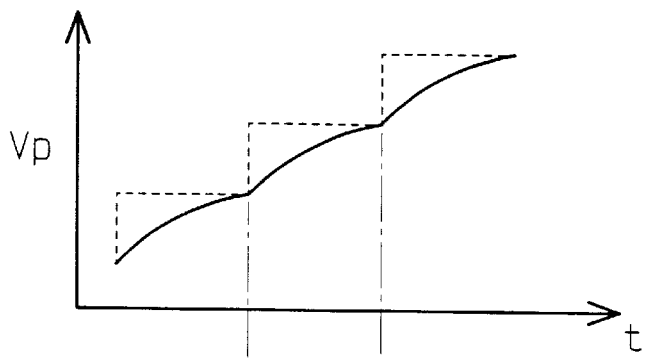
FIGS. 22A and 22B are graphs showing a relation between applied voltage to the air-fuel ratio sensor and sensor current of the air-fuel ratio sensor.
Figure 22B:
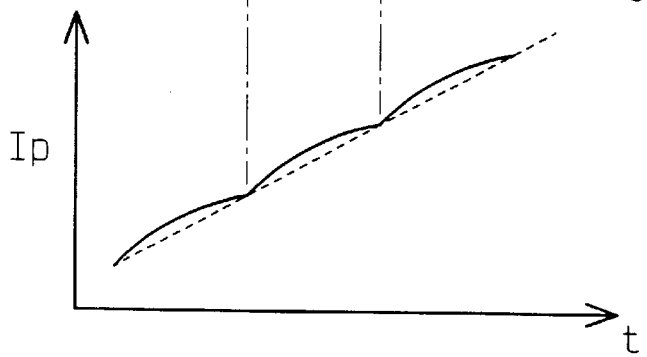
Figure 23:
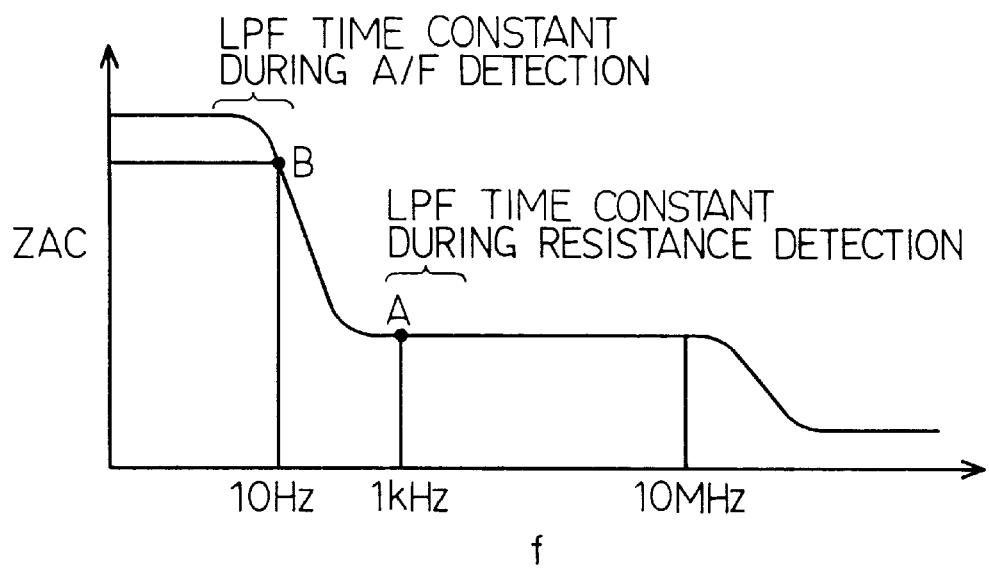
FIG. 23 is a graph showing a relation between the frequency of AC input voltage to the air-fuel ratio sensor and AC impedance characteristics of the air-fuel ratio sensor.

The reason for the decrease in the error produced in detecting the A/F ratio that results when the time constant of the LPF is increased is discussed below. An increase in the time constant of the LPF means a decrease in the frequency of a change in voltage applied to the A/F ratio sensor 30. Then, if the frequency of voltage application is decreased, impedance ZAC increases as shown in FIG. 23. If the impedance ZAC increases, the amount of current change when the applied voltage is changed decreases. Thus, the deviation of the limit current from its true value as shown in FIG. 21B decreases as shown in FIGS. 22A and 22B, thereby reducing the error in the detection of the A/F ratio. Point A (f=1 kHz) in FIG. 23 indicates a cutoff frequency that corresponds to a time constant of the LPF which is suitable for the detection of element resistance and point B (frequency f=10 Hz) indicates a cutoff frequency that corresponds to a time constant of the LPF which is suitable for the detection of the A/F ratio.

Figure 24:
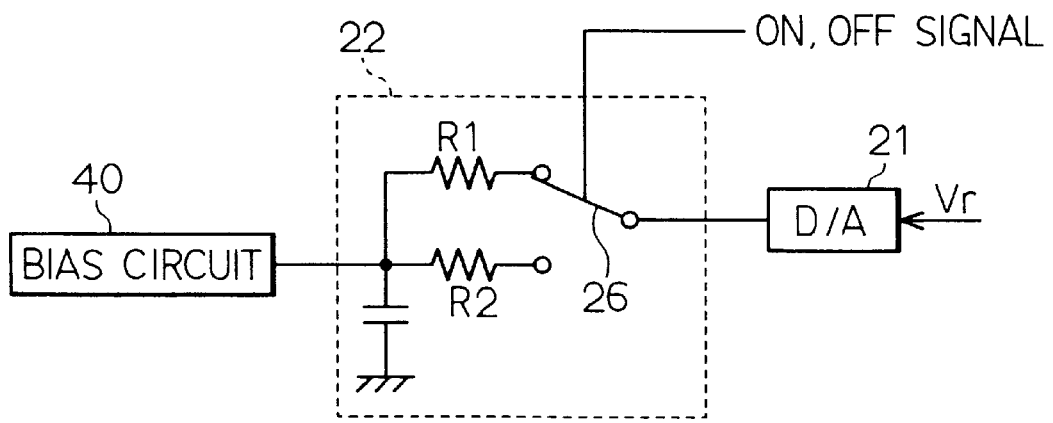
FIG. 24 is a schematic circuit diagram of a switching unit according to a fourth embodiment of the present invention.

From the above description, it is clear that the above problem can be solved by changing the time constant of the LPF 22 as mentioned in FIG. 1 depending on which of the element resistance and the A/F ratio is to be detected. One simplified construction of the LPF 22 is shown in FIG. 24. That is, the construction of FIG. 24 shows that the time constant is changed by switching a resistance of the LPF 22 to R1 or R2 (where R1 >R2) using a switch 26. Concretely, when detecting the A/F ratio, the state of the switch shown in the figure is maintained in order to increase the time constant. On the other hand, when detecting the element resistance, the switch 26 is switched to decrease the time constant. Alternatively, capacitance of a capacitor may be changed to adjust the time constant.

However, it may be difficult to detect the A/F ratio or element resistance precisely because of noise produced when turning the switch 26 on and off, time constant deviation resulting from the actuation resistance of the switch 26 and the like. Therefore, according to the present embodiment, a circuit having no switch as shown in FIG. 25 may be adopted.

Figure 25:
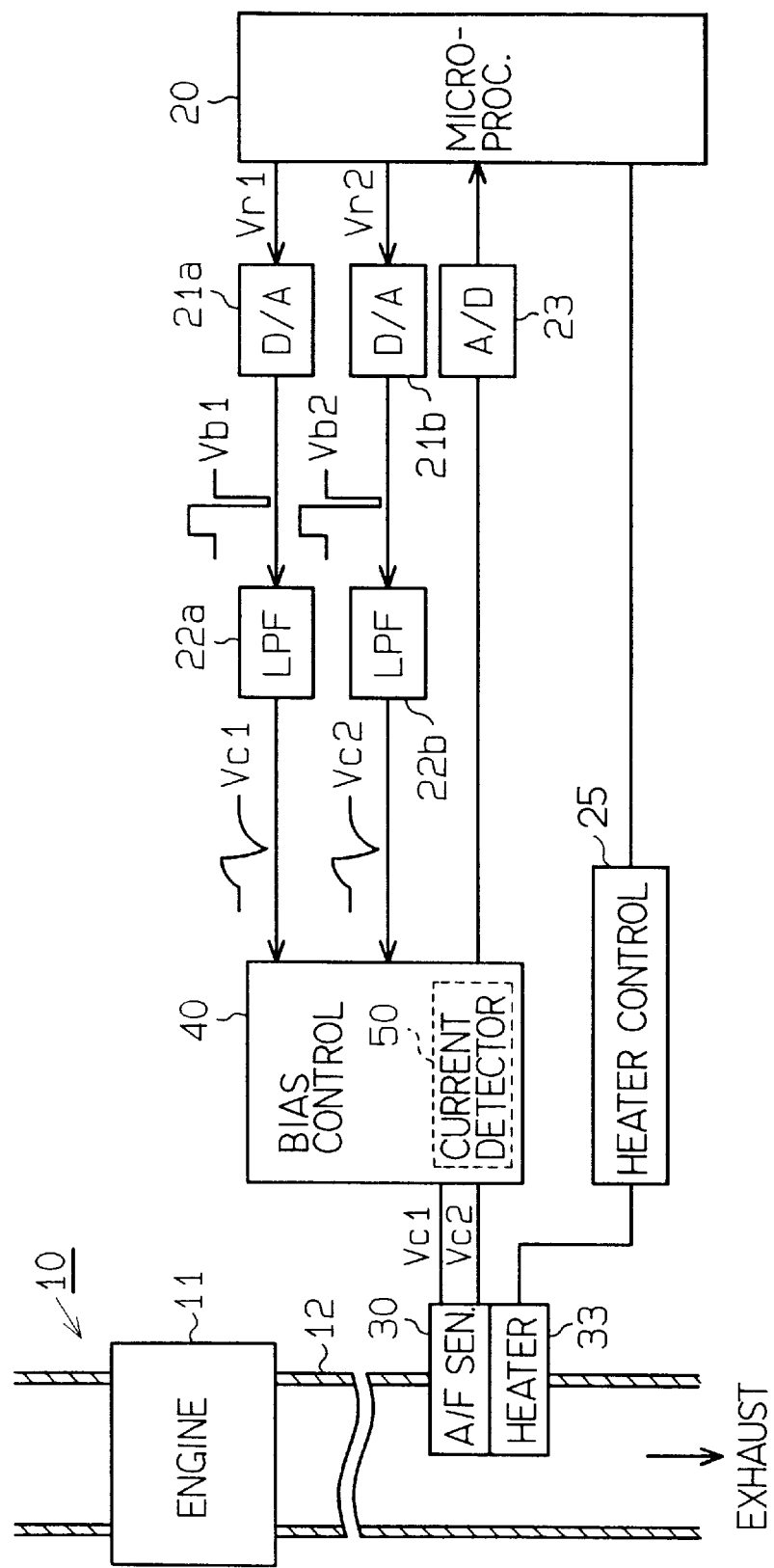
FIG. 25 is a schematic diagram showing the construction of the air-fuel ratio detection device according to the fourth embodiment.

FIG. 25 is a diagram similar to FIG. 1 of the first embodiment. One notable difference of the system shown in FIG. 25 from the system of FIG. 1 is that the system shown in FIG. 25 is provided with two LPFs 22a and 22b and two D/A converters 21a and 21b. It should be noted that the LPF 22a must have a time constant substantially equal to that of the LPF 22 of FIG. 1 and that the LPF 22b must have a time constant larger than that of the LPF 22a.

Here, the microprocessor 20 generates a first bias command signal Vr1 for detecting the element resistance R and a second bias command signal Vr2 for detecting the A/F ratio. Then, the bias command signals Vr1 and Vr2 are provided to the D/A converters 21a and 21b, respectively. The bias command signals Vr1 and Vr2 are then converted to respective analog signals Vb1 and Vb2 by the D/A converters 21a and 21b and then, high frequency components of these analog signals are extracted by the LPFs 22a and 22b. The resulting output voltages Vc1 and Vc2 are subsequently provided to the bias control circuit 40, respectively. Then, the output voltages Vc1 and Vc2 are amplified by the bias control circuit 40 and then applied to terminals that are connected to the atmospheric and exhaust gas side electrodes, respectively, of the A/F ratio sensor 30.

Figure 26:
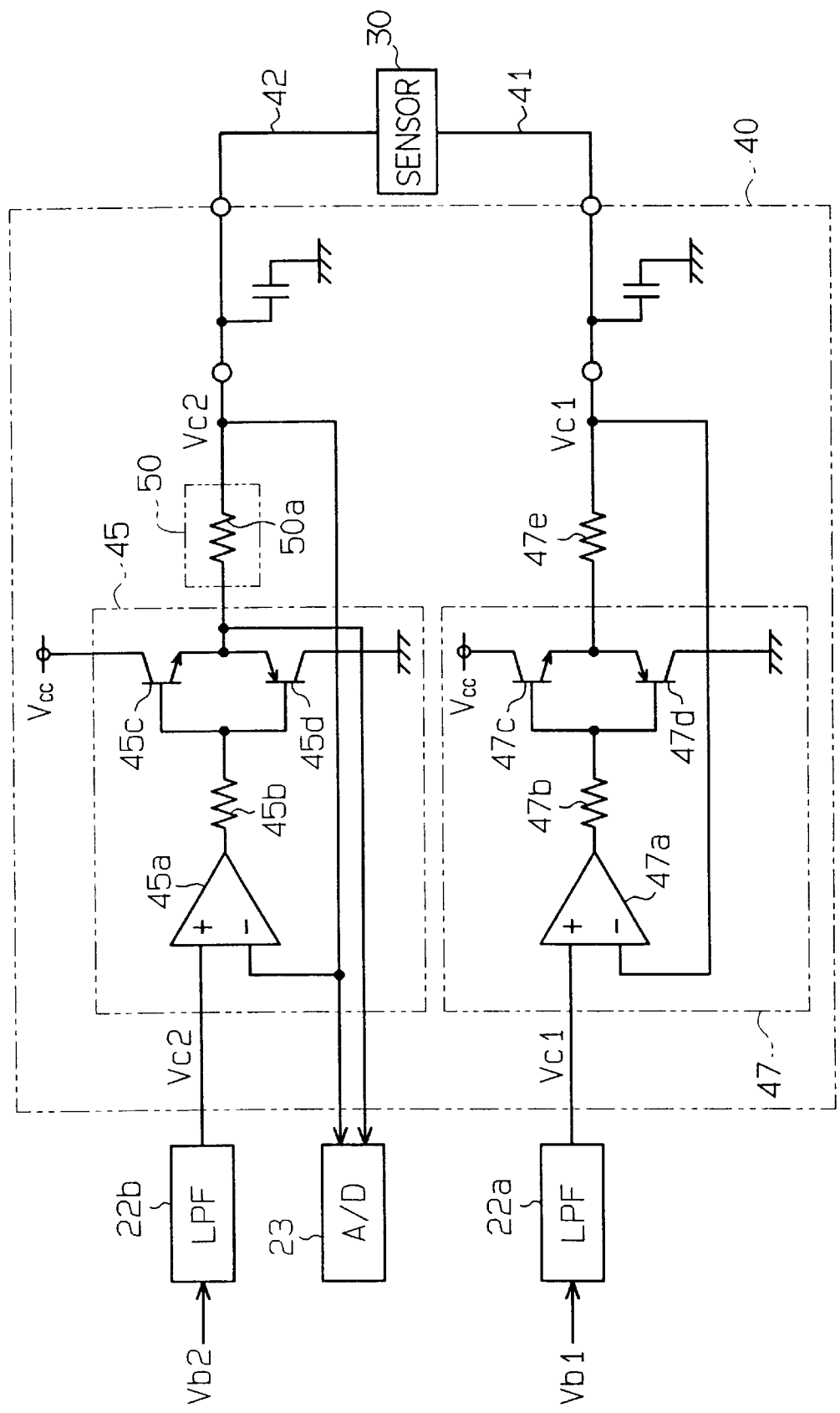
FIG. 26 is a circuit diagram showing the construction of the bias control circuit according to the fourth embodiment.

FIG. 26 is an electric circuit showing a construction of the bias control circuit 40 according to the present embodiment. One difference of the bias control circuit 40 of the present embodiment with the bias control circuit 40 of the first embodiment (which is shown in FIG. 8) is that the present circuit does not have the reference voltage circuit 44 for providing a fixed voltage to the operational amplifier 45a of the first voltage supply circuit 45 and the non-inverting input terminal of the same operational amplifier 45a is supplied with output voltage Vc2 from an additional LPF 22b. Then, the output voltage Vc2 from the LPF 22b is applied to the terminal 42 (i.e., the terminal connected to the atmosphere side electrode layer 37) of the A/F ratio sensor 30.

Hereinafter, the operation of the microprocessor 20 will be described with reference to the flow charts shown in FIGS. 27 and 28.

Figure 27:
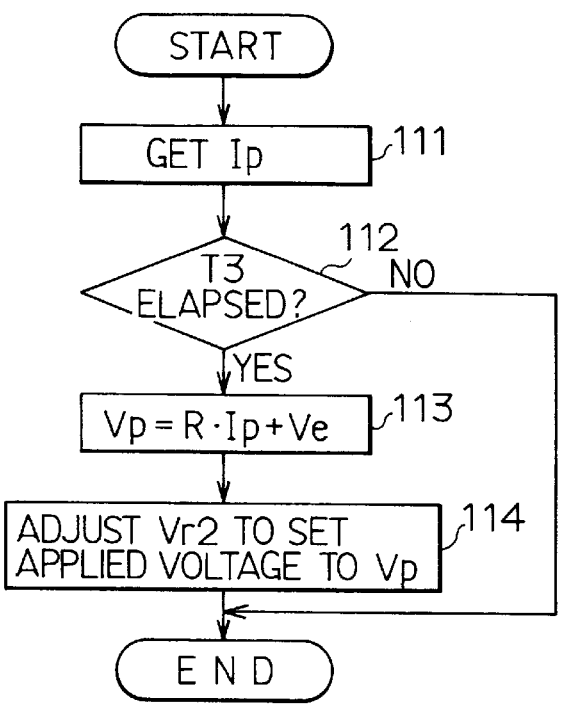
FIG. 27 is a flow chart of a limit current detection subroutine according to the fourth embodiment.

The flow chart of FIG. 27 is a subroutine for detecting a limit current (the A/F ratio). This flow chart shows in detail step 110 of FIG. 9. Referring to FIG. 27, in step 111, the microprocessor 20 first detects a limit current Ip flowing through the A/F ratio sensor 30 based on a detection result of the current detection circuit 50 shown in FIG. 26. Then, in step 112, the microprocessor 20 determines whether a predetermined time T3 has elapsed since the last change in applied voltage Vp. Namely, the predetermined time T3 is the time interval between the timing for changing the voltages for detecting the A/F ratio. This time period T3 must only be longer than the predetermined time T1 for detecting the A/F ratio (see FIG. 9). The predetermined time T3 is preferably set to 2–10 ms.

In this case, if step 112 gives a negative output because the predetermined time T3 has not yet elapsed, the CPU 31 terminates this routine. If step 112 gives a positive output because the predetermined time T3 has elapsed, control goes to step 113.

In step 113, the CPU 31 determines voltage Vp to be applied to the A/F ratio sensor 30 in accordance with the element resistance R as detected during the previous processing and the limit current Ip (Vp=R·Ip+Ve). The equation of step 113 indicates the straight line L1 in FIG. 3. Here, Ve is the intercept of the V axis with the straight line L1 and is initially set to a value of about 0.4 V in the vicinity of the center of the limit current region.

Then, the CPU 31 actually applies applied voltage Vp to the A/F ratio sensor 30 in step 114. At this time, the second bias command value Vr2 from the LPF 22b connected to the terminal 42 of the A/F ratio sensor 30 is supplied as the command voltage to the bias control circuit 40. Subsequently, the LPF 22b extracts high frequency components of the voltage to be actually applied to the A/F ratio sensor 30 based on its time constant. At this time, the first bias command voltage Vr1 of the LPF 22a only needs to be fixed to a predetermined voltage.

The determination of the time constant of the LPF 22b is described below. This time constant is preferably set to a large value as much as possible to improve the precision of detecting the A/F ratio. However, if the time constant is too large, another problem arises. That is, if the time constant of the LPF 22b is larger than a certain value, the voltage to be applied to the A/F ratio sensor 30 cannot respond to a sudden change in the limit current value Ip. Then, the voltage Vp to be applied to the A/F ratio sensor 30 deviates largely from the straight line L1 in FIG. 3. If this time constant is further increased, the applied voltage Vp deviates from its limit current range and thus, the limit current Ip or the A/F ratio cannot be detected precisely. Thus, taking the precision of detecting the A/F ratio and the responsiveness to changes in the limit current Ip into account, as shown in FIG. 23, the time constant of the LPF 22b is preferably set such that the cutoff frequency of the same LPF 22b is about 10 Hz.

Figure 28:
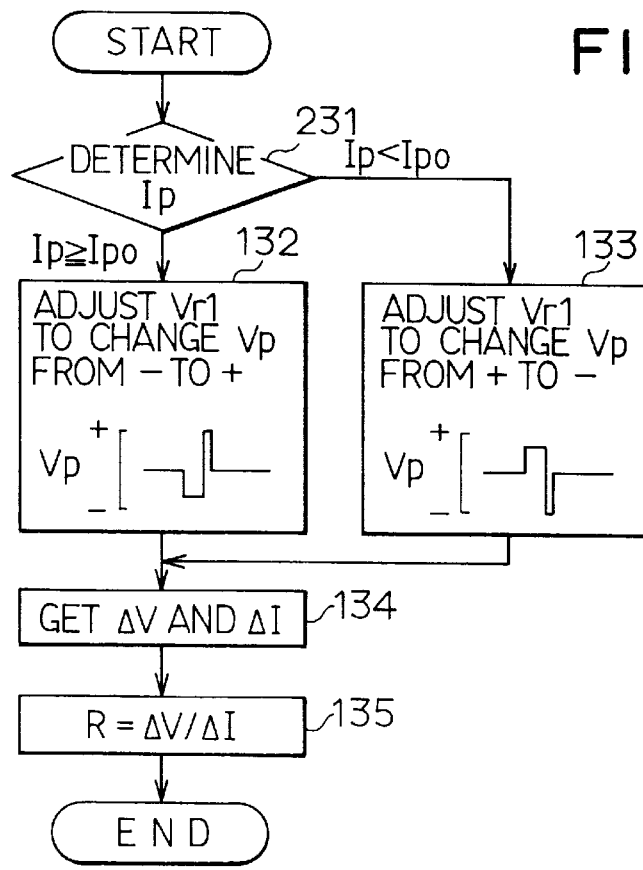
FIG. 28 is a flow chart of the element resistance detection subroutine according to the fourth embodiment.

FIG. 28 is a flow chart corresponding to the element resistance detection subroutine of FIG. 16 of the second embodiment. Although the operation of the subroutine shown in FIG. 28 is basically the same as the subroutine of FIG. 16, it must be noted steps 132 and 133 change the command voltage which is the first bias command voltage Vr1. In this case, the LPF 22a removes the high frequency components from the voltage that will be actually applied to the A/F ratio sensor 30. The time constant of the LPF 22a is substantially the same as that of the first embodiment but is smaller than the time constant of the LPF 22b.

Figure 29:
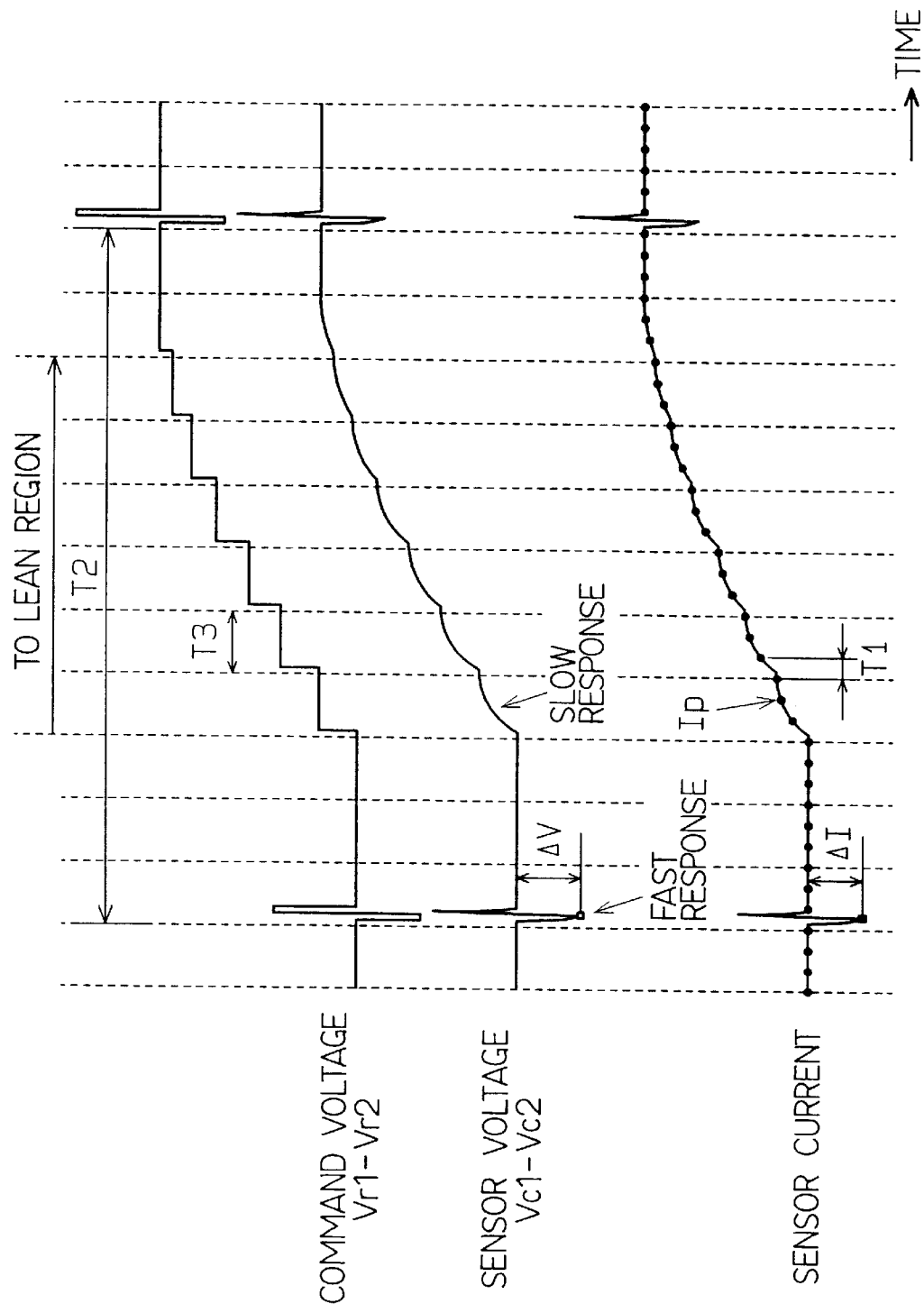
FIG. 29 is a graph that concretely shows operation of the fourth embodiment.

The above operation will be described with reference to a graph shown in FIG. 29. The top waveform shown in FIG. 29 indicates a difference between the two voltages (Vr1–Vr2) generated by the microprocessor 20, the middle waveform indicates a voltage actually applied to the A/F ratio sensor 30, and the bottom waveform indicates the sensor current. The points marked ● on the sensor current waveform indicate limit current Ip detected in step 111 of FIG. 27. The points marked □ on both the sensor voltage waveform and the sensor current waveform indicate ΔV and ΔI that are detected in step 134 of FIG. 28. As has been described before, the limit current Ip is detected at predetermined time T1 intervals while the element resistance R (=ΔV/ΔI) is detected at predetermined time T2 intervals. Furthermore, the sensor voltage command value (second bias command voltage Vr2) for detecting the A/F ratio is changed at predetermined time T3 intervals.

Furthermore, because the A/F ratio of the exhaust gas is moving towards the lean side in the Figure, the sensor current (limit current Ip) increases and, accordingly, the command voltage (Vr1–Vr2) also increases.

In this case, the time constant of the LPF used for removing high frequency components from the command voltage has been changed depending on whether the A/F ratio or the element resistance is to be detected. Therefore, response characteristics of the sensor voltage to the command voltage is different for both cases. Thus, the limit current Ip, ΔV and ΔI can be detected accurately.

The air-fuel ratio control device generates the second bias command signal Vr2 to be applied to the terminal 42 of the A/F ratio sensor 30 for detecting the A/F ratio and then generates the first bias command signal Vr1 to be applied to the terminal 41 for detecting element resistance. However, the air-fuel control device is not limited to this type of arrangement. That is, other constructions may be adopted as long as the air-fuel control device provides a voltage change that has a larger time constant when detecting the A/F ratio than the time constant when detecting the element resistance.

In the same way as the previously described embodiments, the fourth embodiment of the present invention enables accurate detection of the element resistance R. Of course, the present embodiment achieves the objects of the present invention. In addition, it also provides the following advantages.

(a) According to the present embodiment, the time constant for changing the voltage to be applied to the A/F ratio sensor 30 is adjusted depending on whether the element resistance or the A/F ratio is to be detected. Here, compared to the time constant when detecting the element resistance, the time constant of the voltage change is set to a larger value when detecting the A/F ratio. Accordingly, even if the A/F ratio is detected at a period shorter than the period for switching the applied voltage Vp used for detecting the A/F ratio (e.g., T1<T3 as shown in FIG. 29), errors in limit current Ip of the A/F ratio sensor 30 can be eliminated and, thus, deterioration in the accuracy of detecting the A/F ratio can be prevented.

(b) Furthermore, two low-pass filters LPF 22a and LPF 22b, each of which has a unique time constant, are connected to a pair of terminals 41 and 42 that are connected to the solid electrolytic layer 34 of the A/F ratio sensor 30. The two low-pass filters LPF 22a and 22b are selectively used to detect the element resistance and the A/F ratio. In this case, in comparison with a case where a switch is provided and is actuated and deactuated to change the time constant, there will be no detection error due to the resistance of the switch or noise caused by the switching operation. Accordingly, decline in the detection precision can be prevented.

A fifth embodiment of the present invention will be described with reference to FIGS. 30A through 40.

Figure 30A:
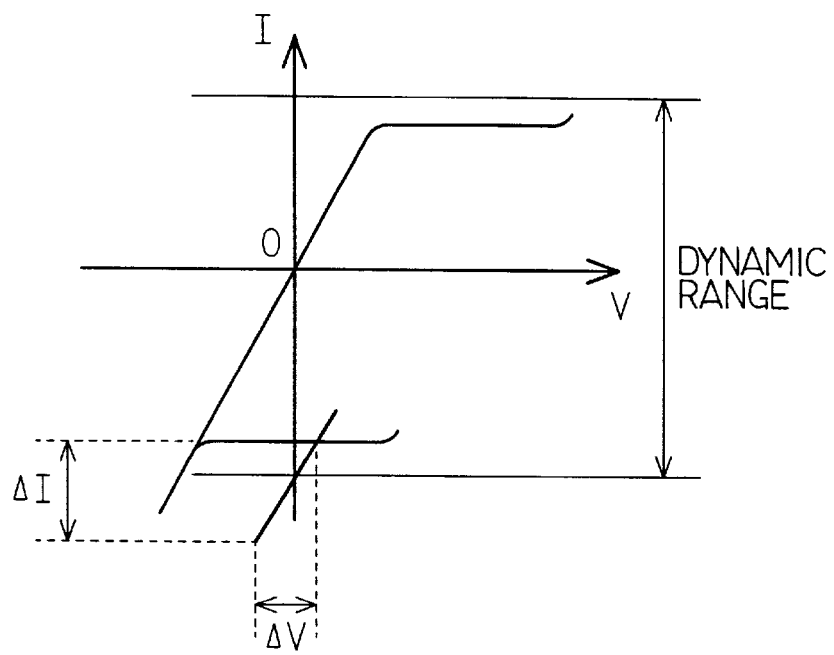
FIGS. 30A–30C are graphs showing voltage-current characteristics of the air-fuel ratio sensor that are out of the dynamic range of the current detection circuit.
Figure 30B:
Figure 30C:
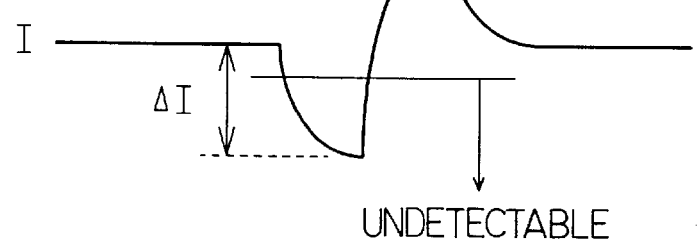

First, the principle behind the operation of the present embodiment will be described briefly with reference to FIGS. 30A–31C. While the detection method according to the previously described embodiments detects current change amount ΔI induced by changing the applied voltage Vp, the current change amount ΔI cannot be detected in the vicinity of a maximum value or minimum value of the dynamic range. Accordingly, this leads to erroneous detection of the element resistance R. If the A/F ratio is in the vicinity of a minimum value of the dynamic range as shown in FIG. 30A, if ΔV is generated so as to cross over the minimum value of the dynamic range, ΔI becomes out of range as shown in FIG. 30C and, thus, the element resistance R cannot be detected (this problem can be solved to some extent by adjusting the direction of the voltage change in accordance with the A/F ratio or sensor current and this embodiment provides an alternative solution for solving such problem).

To solve the above-described problem, according to the present embodiment, as a method for detecting ΔI in the vicinity of the minimum or maximum values of the dynamic range, voltage supply to the A/F ratio sensor 30 is temporarily terminated and then element resistance R is detected based on the sensor electromotive voltage and the current change generated at the instantaneous termination of the voltage application. In this way, the electric resistance R can be detected accurately over the entire range by combining this detection method with the method of detecting element resistance based on voltage change.

Figure 31A:
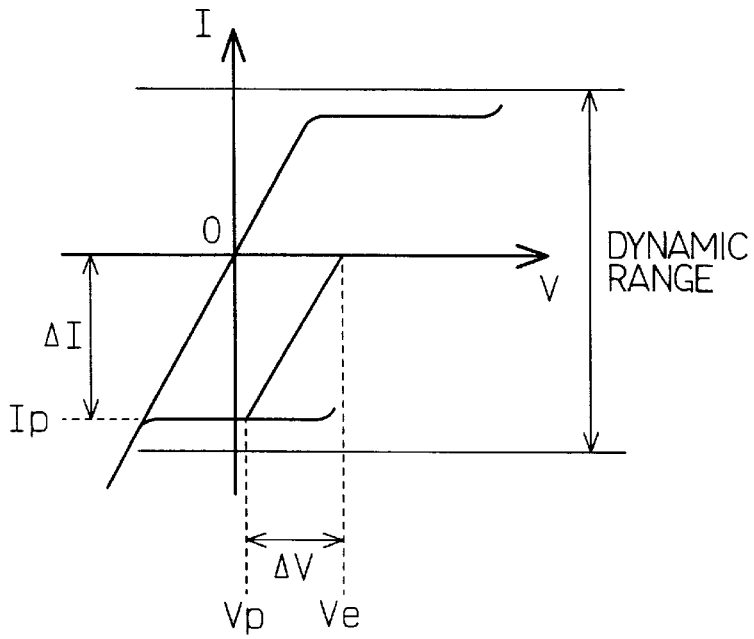
FIGS. 31A–31C are graphs showing voltage-current characteristics of the air-fuel ratio sensor when the air-fuel ratio sensor is shut down.
Figure 31B:
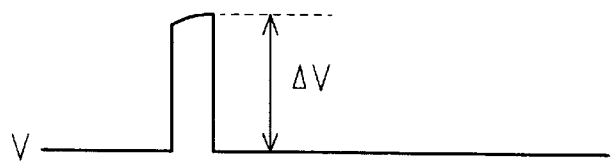
Figure 31C:
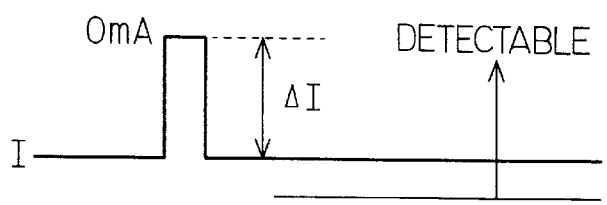

A method of detecting the element resistance R using the voltage of the A/F ratio sensor 30 will be described below. FIGS. 31A–31C are graphs demonstrating the principle behind the operation of this detection method. In detecting the A/F ratio, the voltage Vp is applied to the A/F ratio sensor 30 and the sensor current (limit current) at the time voltage Vp applied is set as Ip. Then, in detecting the element resistance, a part of the circuit through which sensor current Ip flows (i.e., the voltage supply circuit of the A/F ratio sensor 30) is shut down for an instant. Then, the sensor current Ip suddenly becomes 0 and the A/F ratio sensor 30 produces a voltage Ve in accordance with a difference in partial pressure of oxygen between both the internal and external sides of its solid electrolytic layer 34. Based on a ratio of the voltage change amount Δv (=Ve−Vp) with current change amount ΔI, element resistance Re ("Re" is used here to distinguish this resistance from element resistance R detected based on the voltage change) can be detected. Element resistance Re detected in this manner is substantially equal to the element resistance R detected based on voltage change (that is, Re≈R).

The reason for this coincidence of the element resistance Re detected based on the shutdown of the circuit with the element resistance R detected based on the voltage change is explained with reference to FIG. 5 which shows an equivalent circuit of the A/F ratio sensor 30. Because this circuit is in its regular state during the detection of the A/F ratio, current flows through Rg, Ri, and Rf. If the circuit is shut down temporarily under this condition, that is, if current flow is stopped temporarily, Rg loses its potential difference instantaneously because it is a direct current resistor. As for Ri, based on its previous description made with reference to FIGS. 6 and 7, electric charge collected in Ci instantaneously passes through Ri due to its small time constant so that a potential difference across Ri disappears immediately. Therefore, a ratio between the voltage change induced by the shutdown of the circuit and induced current change becomes a sum of Rg and Ri, and thus, element resistance Re detected by the shutdown of the circuit becomes the same value as the element resistance R detected in accordance with the voltage change.

Figure 32:
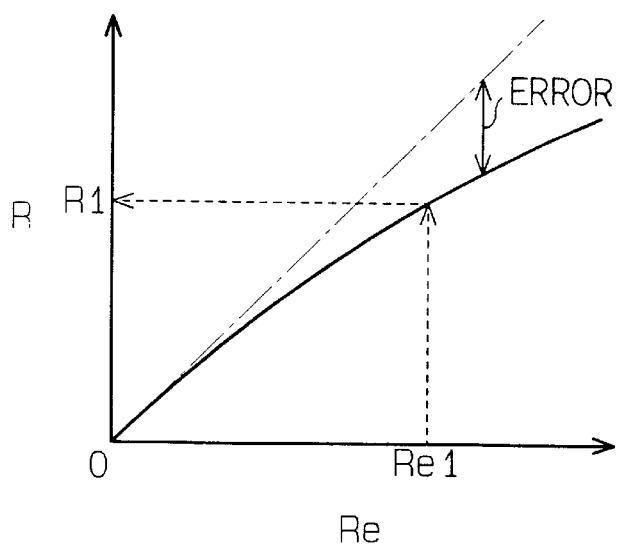
FIG. 32 is a graph showing a relation between an element resistance R detected based on voltage change and characteristics of an element resistance Re detected based on the shutdown of the air-fuel ratio sensor.

However, the actual A/F ratio sensor 30 is not exactly the same as the circuit as shown in FIG. 5. Thus, as shown in FIG. 32, the element resistance R detected based on voltage change does not completely coincide with the element resistance Re detected based on the temporary shutdown of the A/F ratio sensor 30 and thus, some errors may occur. As a result, there might be a discontinuous part in the detected values of the element resistance when switching between these two detection methods. Consequently, in conducting heater control, for example, to keep element resistance constant, the element temperature may not stabilize in the aforementioned discontinuous part.

In this way, according to the present embodiment, to eliminate such discontinuity in the detected element resistances, both of these element resistance detection methods based on voltage change and the temporary shutdown of the circuit are employed within a range that has a predetermined width. Then, a compensation coefficient ka is calculated based on a difference between the element resistances detected using both detection methods. The element resistance Re computed based on the temporary shutdown of the circuit is corrected in accordance with this compensation coefficient.

Figure 33A:
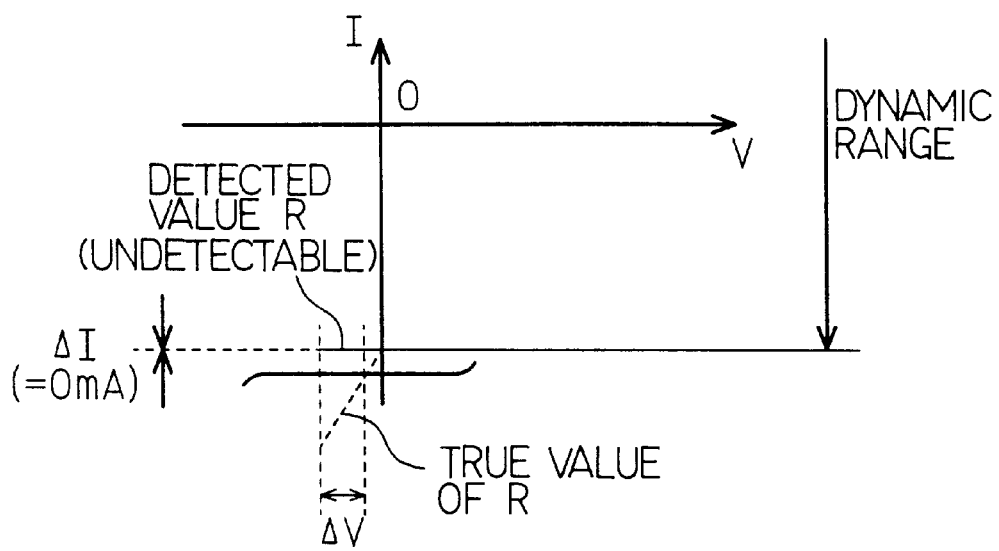
FIGS. 33A and 33B are graphs for comparing the element resistance detection method based on the voltage change with the element resistance detection method based on the shutdown of the air-fuel ratio sensor.
Figure 33B:
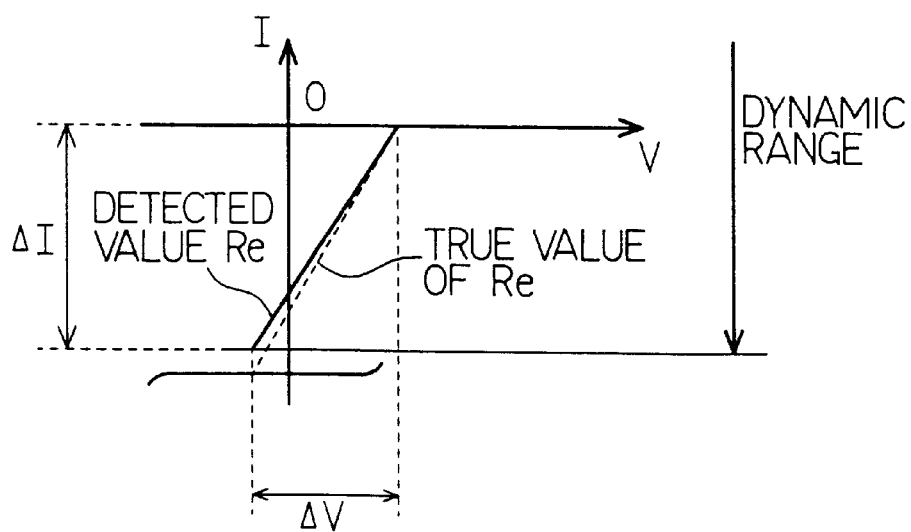

On the other hand, if the limit current Ip is out of the dynamic range, none of the aforementioned detection can be used methods to detect the precise value of the element resistance. However, even in this case, the detection method based on the temporary shutdown of the circuit can be used to detect element resistance although it might produce some errors. Namely, FIGS. 33A and 33B show voltage versus current characteristics of the A/F ratio sensor 30 when the limit current Ip is out of the dynamic range. FIG. 33A shows the element resistance R detected based on the voltage change, while FIG. 33B shows the element resistance Re detected based on the momentary shutdown of the circuit. True values of element resistance R and Re are indicated by broken lines in the respective figures.

Referring to FIGS. 33A and 33B, the element resistance detection method of FIG. 33A cannot detect the current change amount ΔI (ΔI=0). Thus, even if the element resistance changes, such change cannot be detected. On the contrary, the element resistance detection method of FIG. 33B can always calculate an appropriate value of ΔI because the detected current always becomes 0 mA and so, changes in the element resistance can always be detected. For example, even if heater control of the A/F ratio sensor 30 is being conducted to keep the element resistance constant, the use of the element resistance detection method based on the momentary shutdown of the circuit prevents occurrence of a worst-case situation where heater control cannot be performed even if the limit current Ip is out of the dynamic range.

Figure 34:
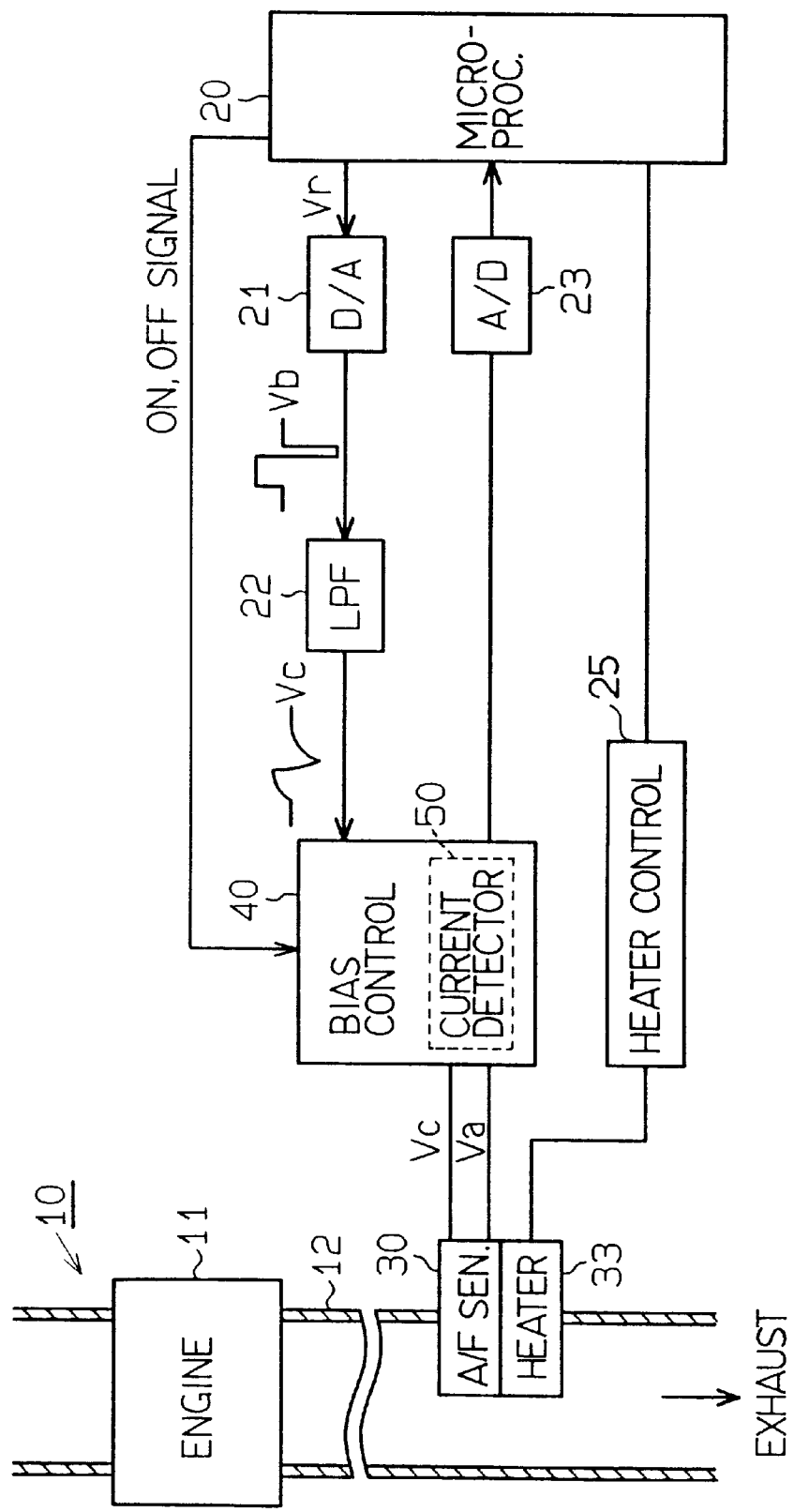
FIG. 34 is a schematic diagram showing the construction of the air-fuel ratio detection device according to a fifth embodiment of the present invention.

A concrete construction of the present embodiment based on the above-described operating principle will be described hereinafter. FIG. 34 shows the entire construction of the air-fuel ratio detection device according to the present embodiment. One difference in construction of the air-fuel detection device of the present embodiment with the construction of the first embodiment shown in FIG. 1 is that the microprocessor 20 provides signals to the bias circuit 40 for actuating and deactuating the switch for temporarily shutting down the sensor circuit.

Figure 35:
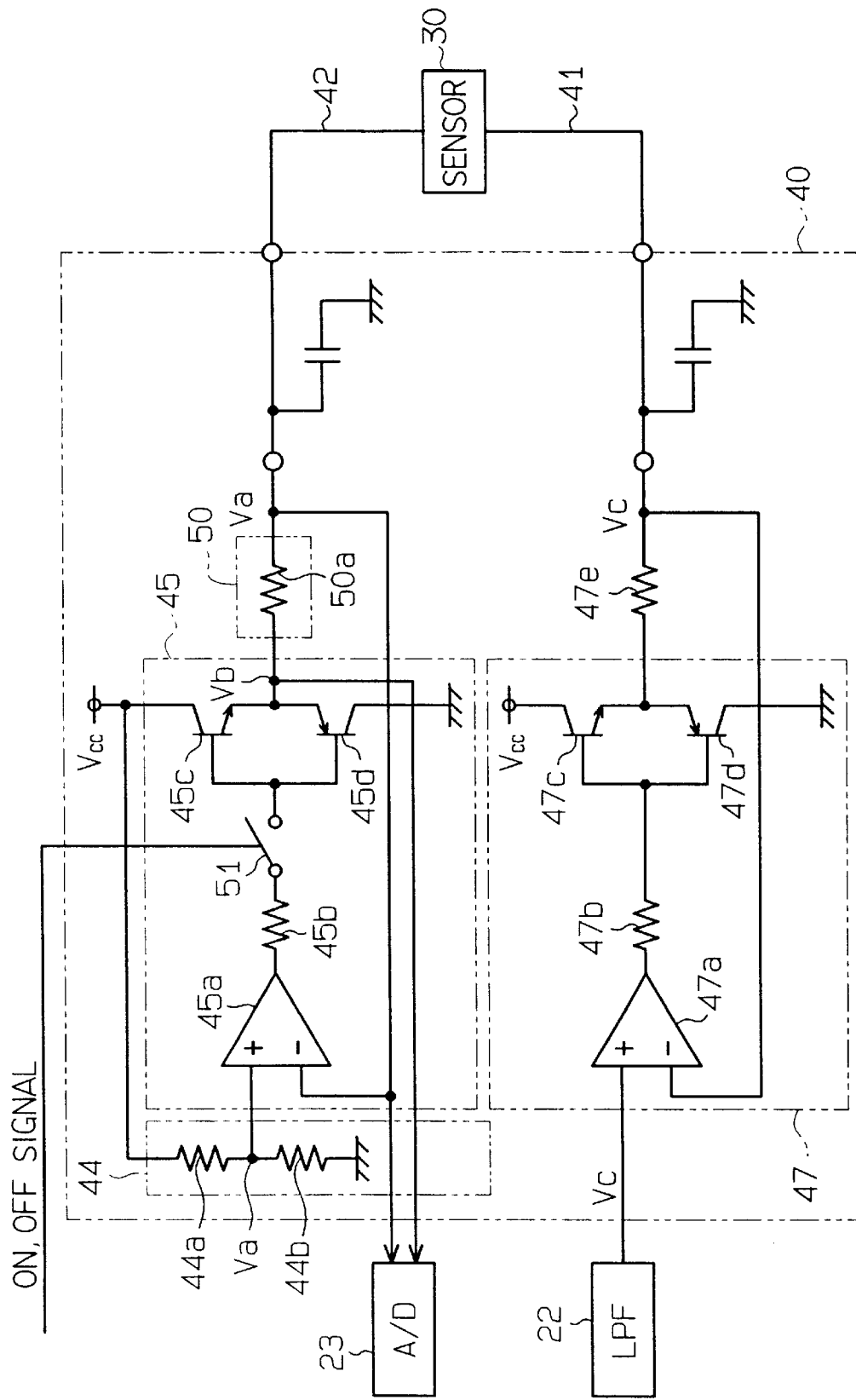
FIG. 35 is a circuit diagram showing the construction of the bias control circuit according to the fifth embodiment.

FIG. 35 shows a construction of the bias control circuit 40. One difference in the construction of the bias control circuit 40 of the present embodiment with the bias control circuit of the first embodiment shown in FIG. 8 is that an analog switch 51 is provided between the resistor 45b and the base of the transistors 45c and 45d of the first voltage supply circuit 45. This analog switch 51 is operated in accordance with ON/OFF signals received from the microprocessor 20. If the switch 51 is deactuated, both the transistors 45c, 45d are deactuated. Accordingly, the emitter terminals of both the transistors 45c and 45d will have high impedance and thus, the circuit connected to the sensor terminal 42 is shut down instantaneously.

Figure 36:
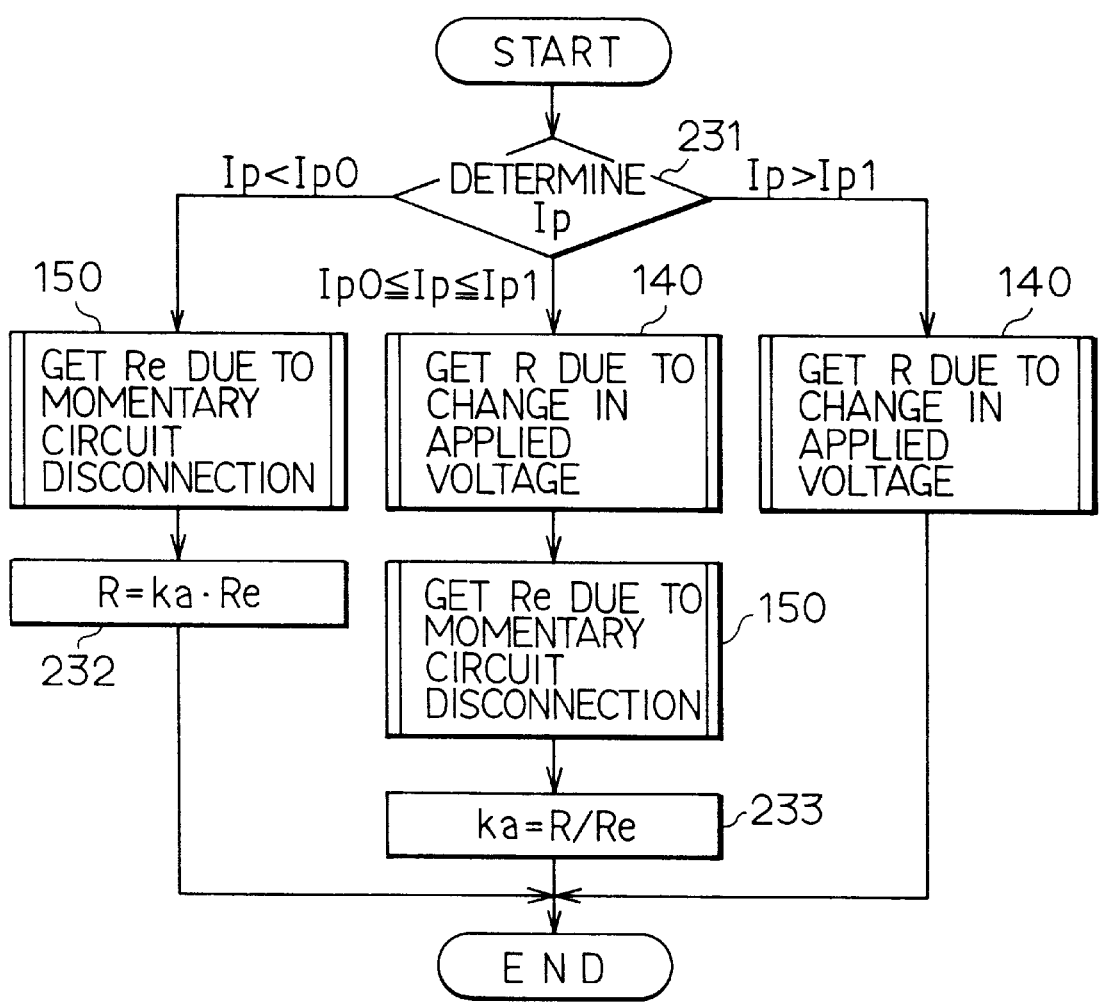
FIG. 36 is a flow chart of the element resistance detection subroutine according to the fifth embodiment.
Figure 37:
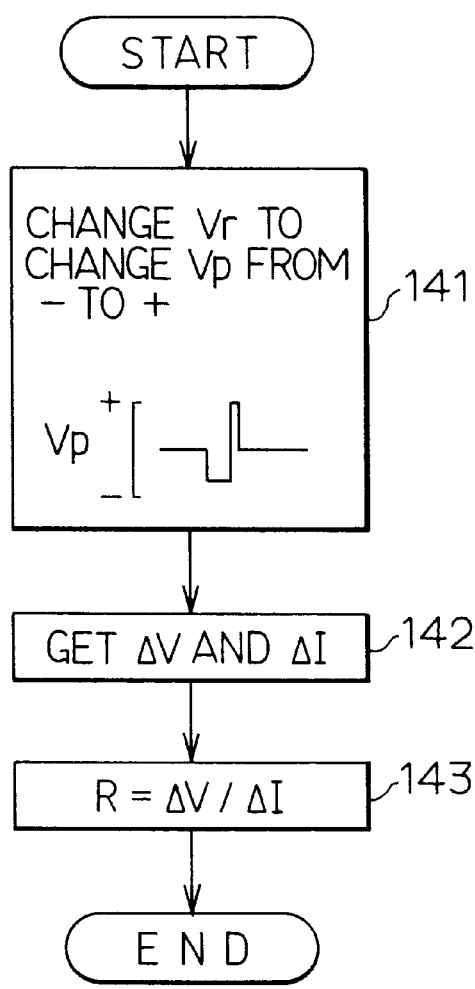
FIG. 37 is a flow chart showing a detection routine of the element resistance based on voltage change according to the fifth embodiment.
Figure 38:
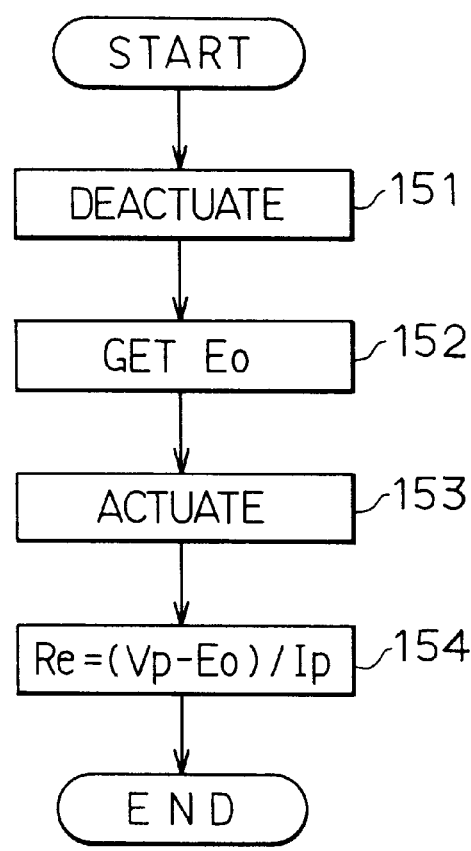
FIG. 38 is a flow chart showing a detection routine of the element resistance based on the shutdown of the air-fuel ratio sensor according to the fifth embodiment.

Hereinafter, the operation of the microprocessor 20 according to the present embodiment will be described with reference to flow charts of FIGS. 36, 37 and 38. FIG. 36 shows a subroutine of step 130 of the main routine shown in FIG. 9, and FIGS. 37 and 38 show subroutines of steps 140 and 150 of FIG. 36.

If the routine of FIG. 36 is activated, the microprocessor 20 determines in step 231 which element resistance detection method should be used based on the previously detected limit current Ip. The microprocessor 20 can choose from among three alternatives: namely, employing only the element resistance detection method based on the voltage change, employing only the element resistance detection method based on the momentary shutdown of the circuit, and employing both the aforementioned element resistance detection methods.

Figure 39:
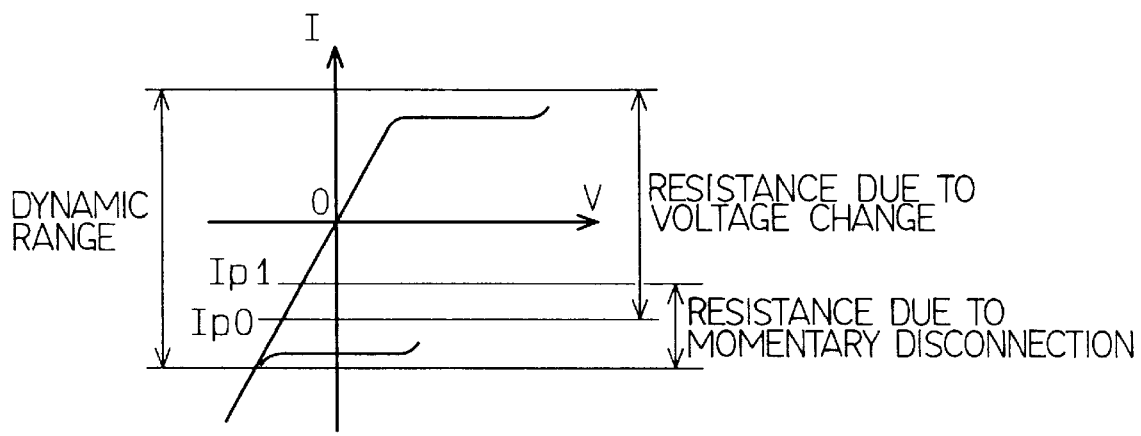
FIG. 39 is a voltage-current characteristic diagram showing the current ranges in which the element resistance detection method based on the voltage change is used and the element resistance detection method based on the temporary shutdown of the air-fuel ratio sensor is used.

That is, according to the present embodiment, as shown in the voltage-current characteristic diagram of FIG. 39, two predetermined values Ip0 and Ip1 with Ip0<Ip1 are set in the vicinity of the minimum value of the dynamic range. Ip0 and Ip1 define a current reference range. If Ip>Ip0, the element resistance is detected based on the voltage change, while if Ip<Ip1, the element resistance is detected based on the shutdown of the circuit. Moreover, if the Ip has a value such that Ip0≦Ip≦Ip1 (i.e. Ip is within the current reference range), the element resistance is detected based on both the voltage change and the temporary shutdown of the circuit.

Therefore, if step 231 of FIG. 36 determines that Ip>Ip1, the microprocessor 20 proceeds to step 140 which detects the element resistance R based on a change in the applied voltage. That is, in step 140, the same operations as in steps 132, 134, and 135 of the routine of the first embodiment shown in FIG. 10 are performed in steps 141 to 143 of FIG. 37 to detect the element resistance R (R=$\Delta V/\Delta I$).

If step 231 determines that Ip<Ip0, the microprocessor 20 proceeds to step 150 which detects the element resistance Re based on method introduced here, that is, the detection of the element resistance Re based on the momentary shutdown of the circuit. FIG. 38 shows a detection routine for element resistance Re based on the shutdown of the circuit. That is, referring to FIG. 38, in step 151, the microprocessor 20 deactuates the switch 51 shown in FIG. 35 to deactuate the first voltage supply circuit 45. Subsequently, the microprocessor 20 detects a voltage Eo (difference between Va and Vc in FIG. 35) in the A/F ratio sensor 30 generated due to the shutdown of the circuit in step 152.

Thereafter, the microprocessor 20 actuates the switch 51 in step 153 and then calculates element resistance Re from the electromotive voltage Eo detected previously, the limit current Ip detected before and the applied voltage Vp prior to temporary shutdown of voltage in step 154 (Re=(Vp-Eo)/Ip).

Then, the microprocessor 20 proceeds to step 232 of FIG. 36 which compensates the element resistance Re obtained in step 150 using a compensation coefficient ka to compute the element resistance R (R=ka·Re). This compensation coefficient ka is used for eliminating the discontinuity between the element resistance R detected based on the voltage change and the element resistance Re detected based on the instantaneous shutdown of the circuit and is calculated when the limit current Ip is in the range from Ip0 to Ip1.

The process to be executed in the case where the limit current Ip is in the range from Ip0 to Ip1 will be described hereinafter. That is, if step 231 determines that Ip0≦Ip≦Ip1, the microprocessor 20 executes step 140 (the process of FIG. 37) to detect the element resistance R based on the change in the applied voltage and subsequently executes step 140 (the process of FIG. 38) to detect the element resistance Re based on the shutdown of the circuit. The microprocessor 20 determines the compensation coefficient ka in accordance with a ratio between the element resistance values R and Re (ka=R /Re). This compensation coefficient ka is used in the aforementioned step 232.

The predetermined values Ip0 and Ip1 of the routine of FIG. 36 may be arbitrarily set to have values between a minimum value of the dynamic range and 0 mA. It must be noted that the detection precision of the element resistance detection method based on the voltage change deteriorates in the vicinity of the minimum value of the dynamic range. On the other hand, because the detection precision of the element resistance detection method deteriorates in the vicinity of 0 mA, a margin of no less than 1 to 2 mA is preferably provided between the 0 mA and Ip1.

According to the fifth embodiment of the present invention, it is possible to detect the element resistance R with a high degree of precision as in the respective embodiments described above. This embodiment enables not only the fulfillment of the objects of the present invention to be achieved but also offers the following additional advantages.

(a) According to the present embodiment, the element resistance detection method based on the voltage change and the element resistance detection method based on the temporary shutdown of the circuit are selectively used in accordance with the limit current Ip of the A/F ratio sensor 30. To put it more concretely, in the vicinity of the minimum value of the dynamic range in which the detection result of the element resistance detection method based on the voltage change is likely to be erroneous, the element resistance detection method based on the shutdown of the circuit is utilized. On the contrary, in the vicinity of 0 mA in which errors by the element resistance detection method based on the shutdown of the circuit are likely, the element resistance detection method based on the voltage change is utilized. Accordingly, the element resistance can be detected precisely for any current detection range.

(b) Furthermore, the predetermined values for switching the above two element resistance detection methods are set in the vicinity of a minimum value (or a maximum value) of the dynamic range. Thus, the element resistance detection method based on the voltage change can be applied for a wider current detection area.

(c) By providing the predetermined values for determining the limit current Ip of the A/F ratio sensor 30 with a predetermined interval (Ip0–Ip1) between them, both element resistance detection methods are executed if the limit current Ip of the above sensor 30 is within the predetermined interval of the predetermined values. The compensation coefficient ka is obtained from a ratio between results of both the detection methods and the element resistance Re detected by temporary shutdown of the circuit is corrected using such compensation coefficient.

Therefore, even if there are differences between the characteristics of the element resistance R detected by the element resistance detection method based on the voltage change and the characteristics of the element resistance Re detected by the element resistance detection method based on the shutdown of the circuit, disparities between the results of both detection methods can be eliminated to remove the discontinuity. As a result, the stable control of the element temperature can be performed even if the heater control based element resistance R is being conducted. The above-described embodiment is effective for correcting errors in cases of disparity between different sensors being utilized and deterioration in the qualities of the sensors.

Meanwhile, the present embodiment can be implemented in the following manner.

In the routine shown in FIG. 36, steps 140 and 150 are executed when the limit current Ip is in the range from Ip0 to Ip1 and the compensation coefficient ka is calculated from the R and Re obtained therefrom. However, it is also possible to estimate the R-Re characteristic of the A/F ratio sensor 30 and then obtain the compensation coefficient ka based on such a characteristic in accordance with a predetermined equation or a map. It is also possible to correct either element resistance based on the characteristics of both the resistances. More concretely, if it is known beforehand that R and Re have a relation like the one shown in FIG. 32, R1, which is an element resistance based on a change in the applied voltage, can be obtained from Re1, which is an element resistance based on the shutdown of the circuit.

While the element resistance R is computed in the present embodiment based on the current change $\Delta I$ by switching the applied voltage Vp from the negative side to the positive side and then computing the current change $\Delta I$ due to change in the applied voltage Vp, it is of course possible to detect the element resistance R by changing the applied voltage Vp from the positive side to the negative side. In this case, the determination of Ip based on Ip0 and Ip1 in step 231 can be performed such that Ipo and Ip1 are set to values that are symmetrical with respect to the horizontal V axis to the values they have in FIG. 39.

Figure 40:
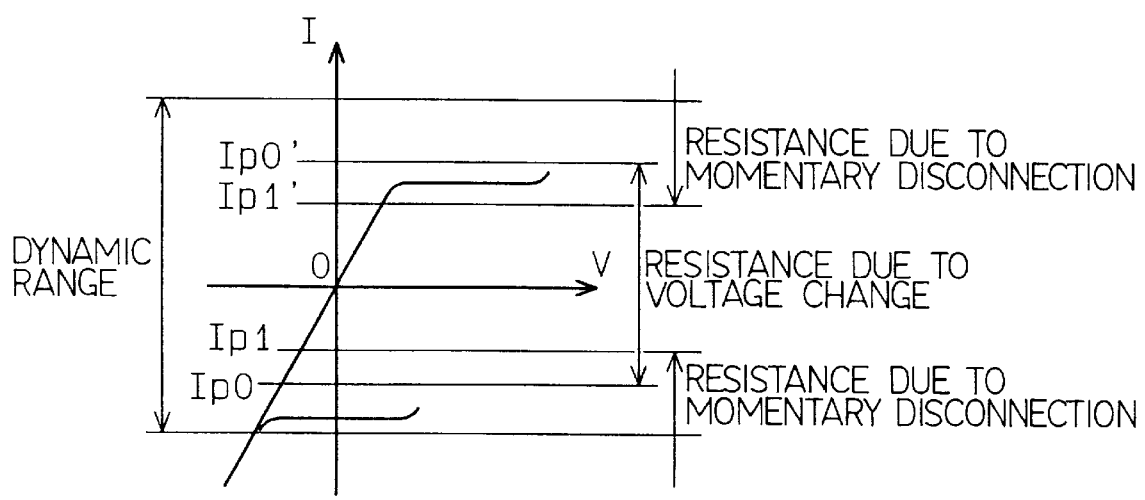
FIG. 40 is a voltage-current characteristic diagram showing the current ranges in which the element resistance detection method based on the voltage change is used and the element resistance detection method based on the temporary shutdown of the air-fuel ratio sensor is used.

If the limit current Ip exceeds the dynamic range, detection precision of the element resistance detection method based on the voltage change is worse than that of the element resistance detection method based on the shutdown of the circuit. Furthermore, if the limit current Ip deviates largely to the lean side, detection of element resistance cannot be performed. This problem can be solved by providing predetermined values Ip0 and Ip1, which define a current reference range, and Ip0' and Ip1', which define another current reference range, on both the negative side and positive side as shown in FIG. 40. In this case, as shown in FIG. 40, if the limit current Ip is near 0 mA, the element resistance detection method based on voltage change is utilized. Meanwhile, if the limit current Ip is near a maximum value or a minimum value of the dynamic range, the element resistance detection method based on the shutdown of the circuit is utilized.

If a difference between the element resistance R detected based on the voltage change and the element resistance Re detected based on the shutdown of the circuit is so small that corrections are not necessary or if the difference between R and Re is to be disregarded to simplify processing, Ip0 may be set to be equal to Ip1 so that the aforementioned detection methods are not performed at the same time. In this case, there will be no need for the compensation coefficient ka used in the flow chart shown in FIG. 36.

Next, a sixth embodiment of the present invention will be described with reference to FIGS. 41 through 45B. Although in the above respective embodiments, the air-fuel ratio detection device is constructed to have a cup-shaped A/F ratio sensor 30 such that the A/F ratio is detected from limit current that flows when voltage is applied to the same sensor 30, in the present embodiment, the air-fuel ratio detection device is constructed using an integrated type A/F ratio sensor 60 instead of the aforementioned A/F ratio sensor 30. The construction and features of the integrated type A/F ratio sensor 60 will be described hereinafter with reference to the accompanying drawings.

Figure 41:
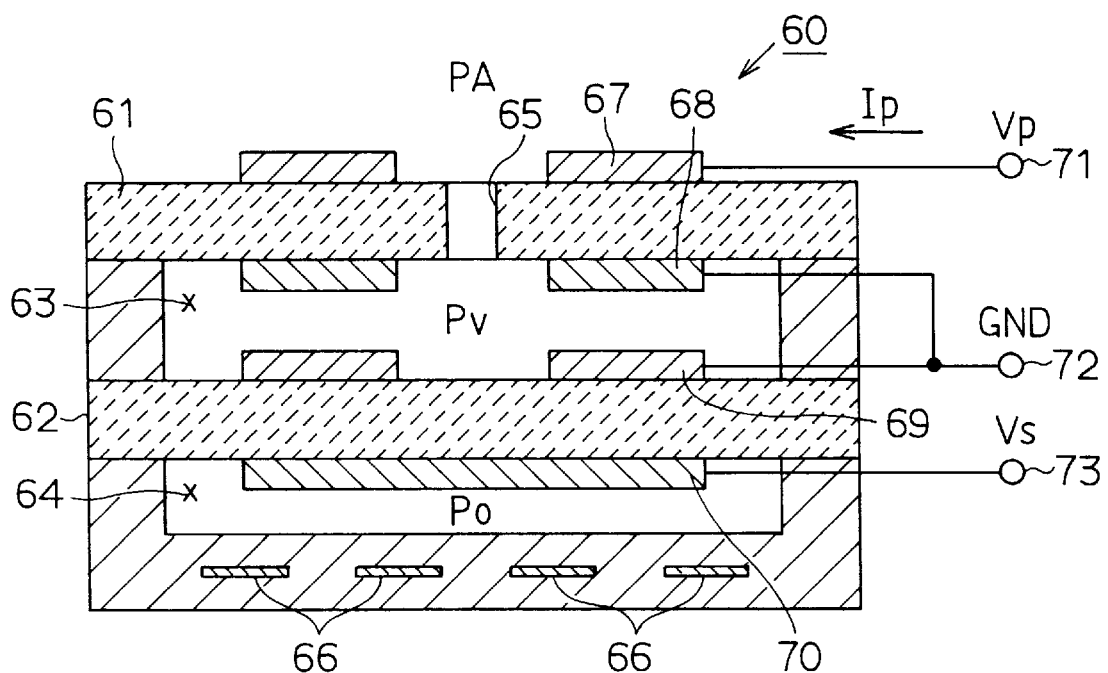
FIG. 41 is a cross-sectional view showing a detailed construction of an integrated type air-fuel ratio sensor according to a sixth embodiment of the present invention.

FIG. 41 is a cross-sectional view showing the construction of the integrated type A/F ratio sensor 60. The integrated type A/F ratio sensor 60 includes two solid electrolytic layers 61, 62 composed of zirconia, which are generally referred to as pumping cell (solid electrolytic layer 61) and sensing cell (solid electrolytic layer 62), respectively. A diffusion gap 63 provided below the solid electrolytic layer 61 acts as an oxygen concentration measuring chamber. On the other hand, an air duct 64 provided below the solid electrolytic layer 62 acts as an atmospheric pressure chamber. Pin holes 65 are formed in the solid electrolytic layer 61 to allow exhaust gas to enter the diffusion gap 63. Heaters 66 are provided for heating the sensor 60.

Platinum electrodes 67 and 68 are fixed on top and bottom surfaces of the solid electrolytic layer 61 (i.e., a pumping cell) and, furthermore, platinum electrodes 69 and 70 are fixed on the top and bottom surfaces of the solid electrolytic layer 62 (i.e., a sensing cell). A terminal 71 is connected to the electrode 67, a terminal 72 is connected to electrodes 68 and 69, and a terminal 73 is connected to the electrode 70.

Figure 42:
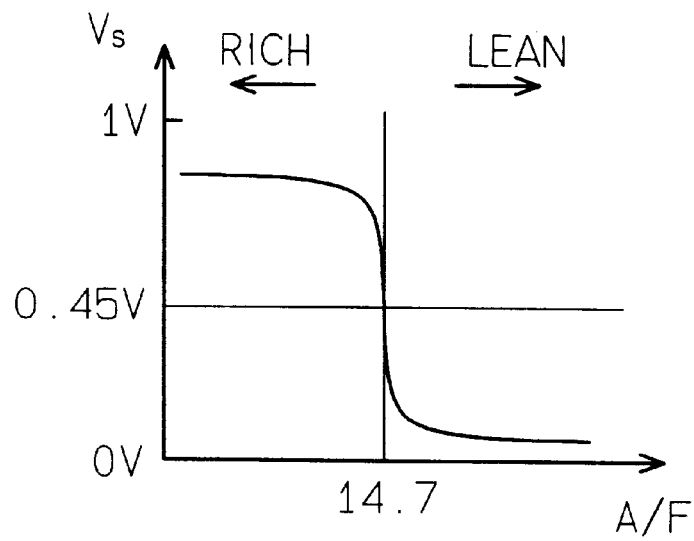
FIG. 42 is a graph showing a relation between a sensor electromotive voltage of the integrated type air-fuel ratio sensor and the air-fuel ratio according to the sixth embodiment.

The operating principle of this integrated type A/F ratio sensor 60 will be explained hereinafter. FIG. 42 is a graph showing the characteristic of a sensor electromotive voltage Vs generated between the terminals 72 and 73. The sensor electromotive voltage Vs is determined based on an oxygen concentration Pv within the diffusion gap 63 and an oxygen concentration Po (equal to an oxygen concentration of the atmosphere) within the air duct 64 as indicated by Equation (2).

$$Vs=(RT*\ln[Po/Pv])/4F \qquad (2)$$

In Equation (2), R is a gas constant, T is an absolute temperature and F is Faraday's constant.

Oxygen concentration Pv within the diffusion gap 63 is usually equal to oxygen concentration PA of the exhaust gas. Therefore, if the A/F ratio becomes rich and the oxygen concentration PA of exhaust gas decreases, the oxygen concentration Pv within the diffusion gap 63 also decreases and thus, the sensor electromotive voltage Vs increases. On the contrary, if the A/F ratio becomes lean, oxygen concentration Pv within the diffusion gap 63 increases and the sensor electromotive voltage Vs decreases. This sensor electromotive voltage Vs is detected by the terminal 73.

Furthermore, by applying the voltage Vp to the terminal 71 to make a pumping current Ip flow therethrough, oxygen ions will pass through the solid electrolytic layer 61. In this way, oxygen concentration Pv within the diffusion gap 63 can be freely controlled. In accordance with the above described principle, if the sensor electromotive voltage Vs is detected and the applied voltage Vp to the terminal 71 is controlled to make Vs constant, oxygen concentration of exhaust gas or the A/F can be controlled in accordance with the pumping current Ip.

Figure 43:
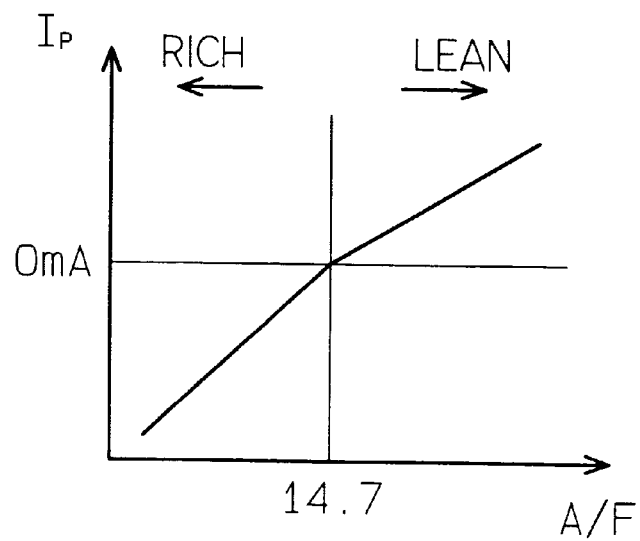
FIG. 43 is a graph showing a relation between a pumping current in the integrated type air-fuel ratio sensor and the air-fuel ratio.

In other words, to control the sensor electromotive voltage Vs to be constant, oxygen concentration Pv within the diffusion gap 63 must be always controlled to be at a constant oxygen concentration Pvo. For this purpose, an amount of oxygen equivalent to a difference between oxygen concentration PA of exhaust gas and oxygen concentration Pvo must be supplied. In this case, the amount of supplied oxygen corresponding to the difference between the PA and the Pvo is determined based on the magnitude of the pumping current Ip. Thus, oxygen concentration (A/F) in exhaust gas can be detected in accordance with the pumping current Ip. As shown in FIG. 42, if the sensor electromotive voltage Vs is controlled to be at a predetermined value (Vs=0.45 V) when the A/F ratio is equal to 14.7 (i.e., the stoichiometric A/F value which varies slightly depending on the type of engine), the characteristic between the pumping current Ip and the A/F ratio will be as shown in FIG. 43 wherein Ip=0 when the A/F ratio is 14.7. The characteristic diagram of FIG. 43 shows that if the A/F ratio is lean, a positive pumping current Ip flows. On the other hand, if the A/F ratio is rich, negative pumping current Ip flows.

Figure 44:
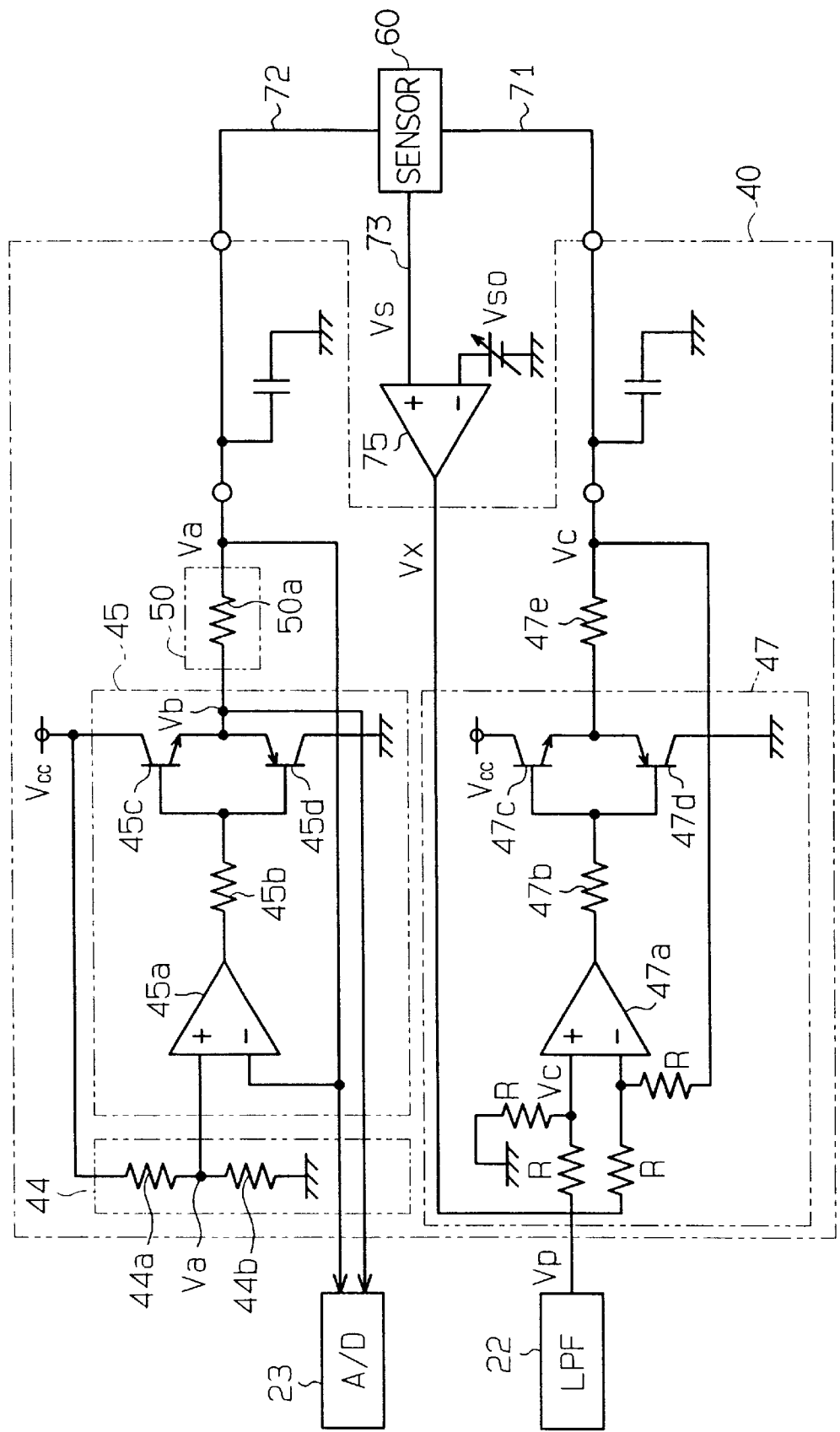
FIG. 44 is a diagram showing a construction of the bias control circuit according to the sixth embodiment.

FIG. 44 is an electrical circuit diagram showing a construction of the bias control circuit 40 according to the present embodiment. Hereinafter, only the differences of the present embodiment with those embodiments using the cup type sensor will be described.

The integrated type A/F ratio sensor 60 has one other terminal 73 for detecting electromotive voltage in addition to the terminals 71, 72 (equivalent to the terminals 41, 42 of FIG. 8), which are for applying voltage to the sensor element. In this case, the electromotive voltage Vs is detected from the terminal 73 and an operational amplifier 75 compares the sensor electromotive voltage Vs with a reference voltage So and generates an amplified result of the comparison. Furthermore, the amplified signal is provided to the second voltage supply circuit 47 to obtain a difference between this amplified signal and a signal provided by the LPF 22. That is, in comparison with the first embodiment in which the cup-shaped sensor is used, the second voltage supply circuit 47 functions as differential amplifier circuit rather than as a voltage follower circuit.

In this circuit, the reference voltage VSo in the operational amplifier 75 is adjusted as follows. That is, in the present embodiment, the reference voltage VSo is adjusted so that Ip is 0 when the A/F ratio is 14.7. In other words, when the A/F ratio is 14.7, a voltage at the terminal 71 must be the same as the voltage at the terminal 72. Assuming the output of the LPF 22 and the voltage to be used for detecting the A/F ratio is Vp, the reference voltage VSo is adjusted such that an output Vx of the operational amplifier 75 is equal to Vp−Va.

In the construction of this circuit, if exhaust gas becomes rich, the sensor electromotive voltage Vs from the terminal 73 increases and thus, the output of the operational amplifier 75 increases. At the same time, the output Vc of the second voltage supply circuit 47 decreases and thus, the voltage applied to the terminal 71 decreases. Consequently, the pumping current Ip flows in a direction opposite to that indicated in FIG. 41 (that is, a pumping current in the negative direction flows). Thus, oxygen is drawn into the diffusion gap 63. On the contrary, if exhaust gas becomes lean, a pumping current Ip in the positive direction flows and oxygen is pumped out from the diffusion gap 63.

Figures 45A, 45B:
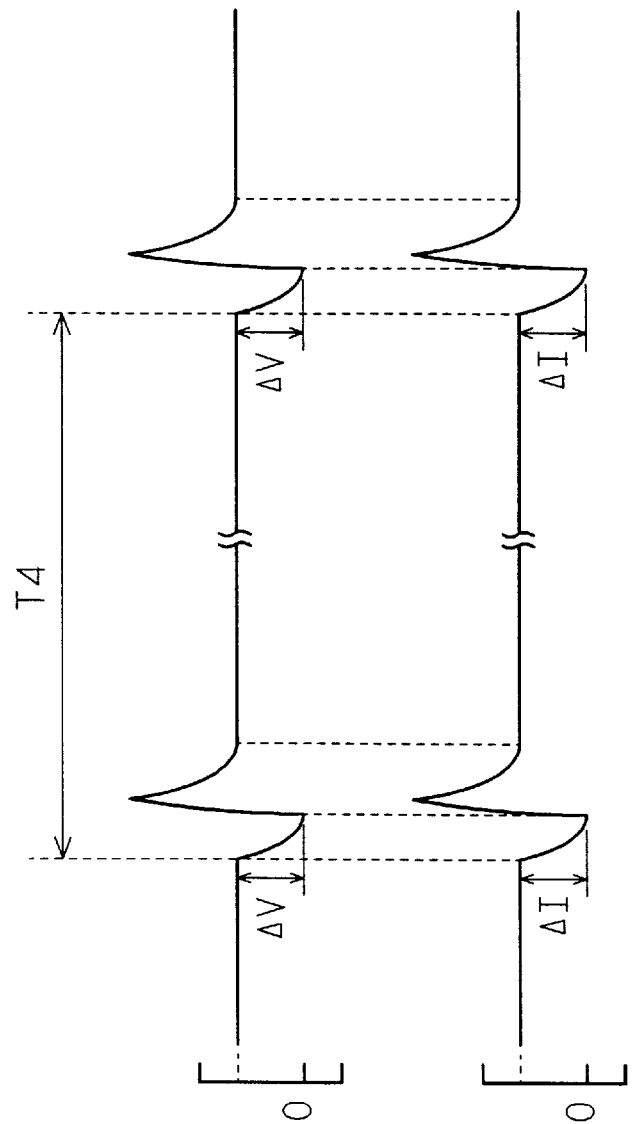
FIGS. 45A and 45B show waveforms of a voltage change and the corresponding current change according to the sixth embodiment.

In the air-fuel ratio detection device according to the present embodiment having the above described construction, the element resistance of the integrated type A/F ratio sensor 60 is detected using the same procedure as that of the first embodiment. An outline of such a procedure will be described with reference to a timing chart shown in FIGS. 45A and 45B. FIG. 45A shows a voltage (that is, the output voltage of the LPF 22) to be applied to the A/F ratio sensor 60 while FIG. 45B shows the sensor current (that is, the pumping current Ip) that flows due to the application of such voltage.

That is, upon detecting element resistance, the applied voltage is applied to the integrated type A/F ratio sensor 60 as a signal having a predetermined time constant by passing through the LPF 22. At this time, the applied voltage is changed to both the positive side and the negative side with respect to a voltage for detecting the A/F ratio. Then, because the A/F ratio is lean, the element resistance R is detected from a negative voltage change ΔV and a negative current change (R=ΔV/ΔI). The reason for using the value measured in the negative side is the same as that of the first embodiment, that is, such setting enables the dynamic range of the A/F ratio sensor 60 to be set to set to a minimum. A detection process of the element resistance R is executed every predetermined cycle T4 (T4 may be a fixed value or a value that varies depending on the operating condition of the engine). Although not graphically represented, when the A/F ratio is rich, the element resistance R is detected from the positive voltage change ΔV and a positive current change ΔI.

According to the sixth embodiment, the same effects as the foregoing embodiments described before can be attained and thus, the element resistance can be detected with a high degree of precision thereby realizing the objects of the present invention.

Further, a seventh embodiment of the present invention will be described with reference to FIGS. 46A–46C to FIG. 52. This seventh embodiment is a modification of the first embodiment shown in FIG. 1 to FIG. 12 and uses the same A/F ratio sensor 30 (FIG. 2) and the electric control circuit (FIGS. 1 and ()). This embodiment is, however, different from the first embodiment in that the time period from time t1 to time t2 (FIGS. 4A and 4B) is determined in the following manner so that the peak current ΔI may be detected accurately after the voltage applied to the A/F ratio sensor 30 changes at the predetermined time constant.

Figure 46A:
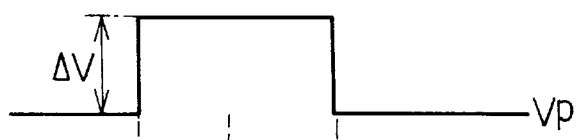
FIGS. 46A–46C show waveforms of the output voltage of the D/A converter, the output voltage of the low pass filter and the sensor current produced in a seventh embodiment of the present invention.
Figure 46B:
Figure 46C:
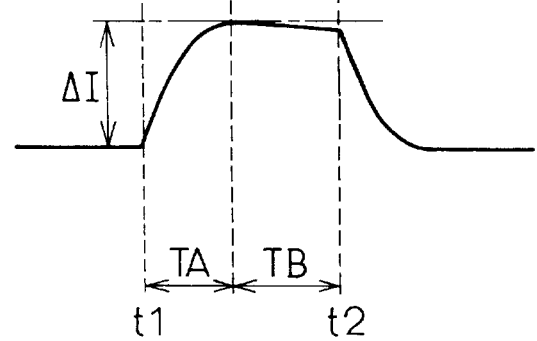

In the present embodiment, as shown in FIG. 46A–46C, the microprocessor 20 is programmed to cause the D/A converter 21 to produce the output voltage Vb which changes from Vp (voltage for the A/F detection) to Vp+ΔV (voltage for the element resistance detection) at time t1 and returns to Vp at time t2. This voltage Vb is changed to the output voltage Vc by the LPF 22. Specifically, the voltage Vc changes or rises at the predetermined time constant during a time period TA and maintains its constant magnitude after the predetermined time constant, i.e., during the following time period TB. As a result, the sensor current Ip also rises at the same time constant during the time period TA and only very slightly falls in the time period TB. As the sensor current Ip is substantially unchanged during the time period TB, there will occur very little difference in the detection of the peak current (change in sensor current Ip) ΔI whatever time the current ΔI may be detected.

Figure 47A:
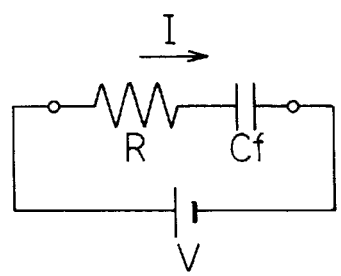
FIGS. 47A and 47B are simplified equivalent electric circuits of the air-fuel ratio sensor.

It is to be noted that the sensor current Ip changes only very slightly during the time period TB due to the following reasons. As the voltage Vc actually applied to the A/F ratio sensor 30 has a rising time constant of some kHz to some tens of kHz, a current in FIG. 5 flows mostly through a path Rg-Ri-Cf. Therefore, the electric equivalent circuit of the sensor shown in FIG. 5 is simplified as shown in FIG. 47A, resulting in an HPF (high pass filter) shown in FIG. 47B. This electric equivalent circuit (HPF) has a frequency-resistance characteristics shown in FIG. 48 which is similar to the characteristics shown around the point A in FIG. 7. In this figure, the point B corresponds to the cut-off frequency of the HPF shown in FIGS. 47A and 47B.

Figure 47B:
Figure 48:
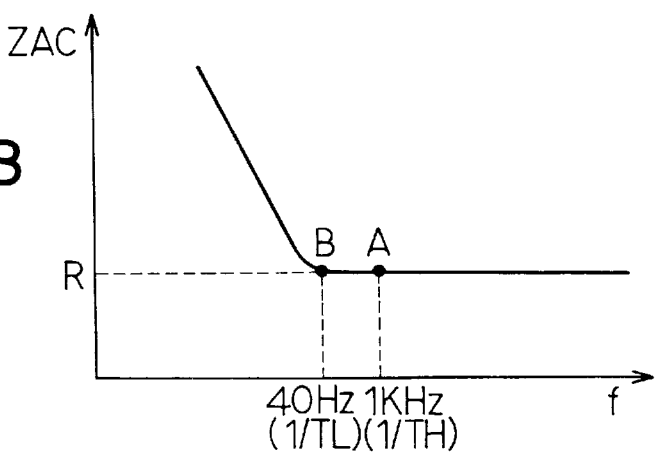
FIG. 48 is a graph showing a relation between the frequency of input voltage to the air-fuel ratio sensor and the impedance characteristics of the air-fuel ratio sensor.
Figure 49A:
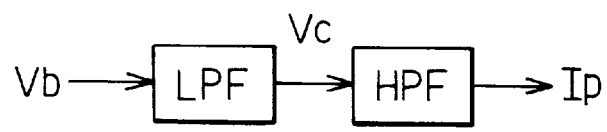
FIGS. 49A–49C show a block diagram, and waveforms of the voltage and the current of the air-fuel ratio sensor, respectively.
Figure 49B:
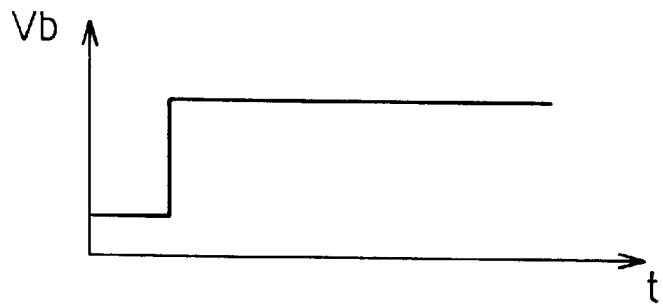
Figure 49C:
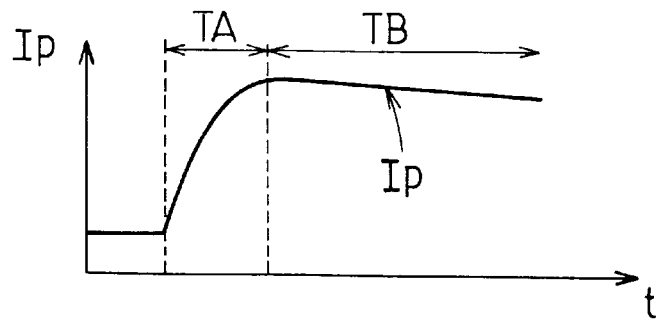

It will be understood from the above discussion that the circuit configuration from the voltage Vb of D/A converter 21 to the current Ip of A/F ratio sensor 30 may be expressed as shown in FIG. 49A, in which LPF and HPF correspond to the LPF 22 in FIG. 1 and the HPF in FIGS. 47A and 47B, respectively. According to this block diagram, the voltage Vb for the A/F ratio sensor 30 and the sensor current Ip of the A/F ratio sensor 30 changes as shown in FIGS. 49B and 49C. Thus, the sensor current Ip is expressed by the following equation with TL and TH being the time constant of the LPF (equivalent to point A in FIG. 48) and the time constant of the HPF (equivalent to point B in FIG. 48).

$$Ip=(\Delta V/R) \times [TH/(TL-TH)] \times (e^{-t/TL} - e^{-t/TH})$$

In the present embodiment, it is necessary to set the point A at the higher frequency side than the point A so that the stable frequency-resistance range. For this reason, the time constants TL and TH are determined to satisfy TL<TH. Thus, from the above equation, the falling change of ΔI during the time period TB becomes much slower than the rising change of the same during the time period TA as shown in FIG. 46C and FIG. 49C.

As explained above, in the time period TB in which the output voltage Vb is maintained at the constant magnitude as shown in FIG. 46B, the sensor current Ip also changes only very slightly during the time period of about 2.5 ms which is within the range one-digit lower than the time constant of the HPF (equivalent circuit of the sensor, etc.) as shown in FIG. 46C. Thus, during the time period TB in FIG. 46C, substantially the same peak current ΔI will be detected at whatever time point it may be detected.

Figure 50:
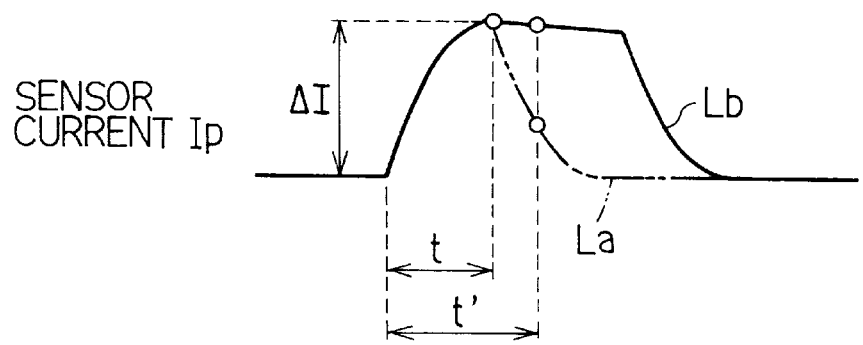
FIG. 50 show a waveform of the current of the air-fuel ratio sensor.

Although the peak current ΔI is detected erroneously by changes in the detection time point from time t to t' in the case that the sensor current Ip changes in the sine waveform La shown by a two-dotted chain line in FIG. 50, the peak current ΔI can be detected accurately even at the time point t' because the sensor current Ip changes in the waveform Lb as shown by a solid line in FIG. 50. Thus, the total time period TA+TB is set to a period longer than the time period required for detecting the peak current ΔI, i.e., longer than some tens of µs.

Figure 51:
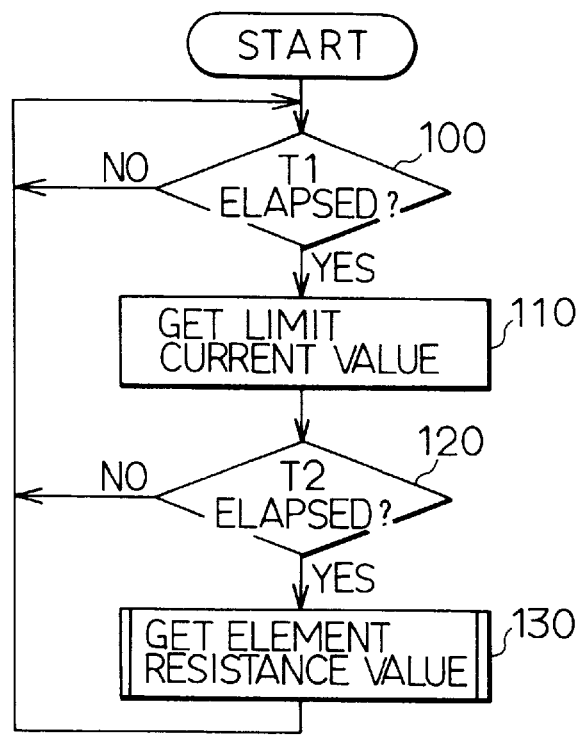
FIG. 51 is a flow chart showing a main routine executed by the microprocessor of the air-fuel ratio detection device of the seventh embodiment.
Figure 52:
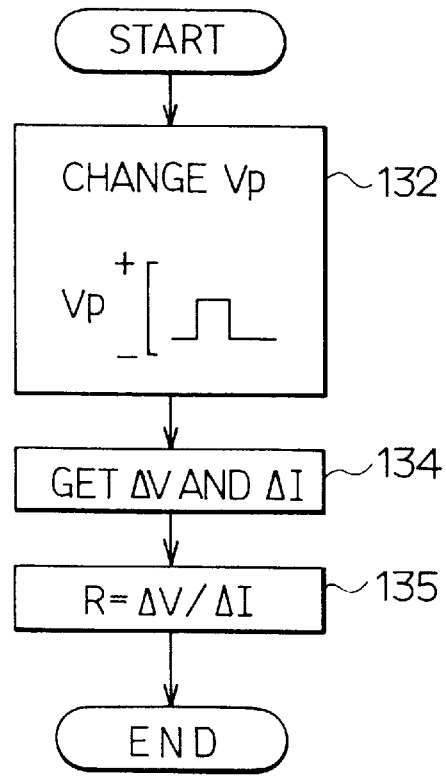
FIG. 52 is a flow chart showing an element resistance detection subroutine executed by the microprocessor according to the seventh embodiment.
Figure 53A:
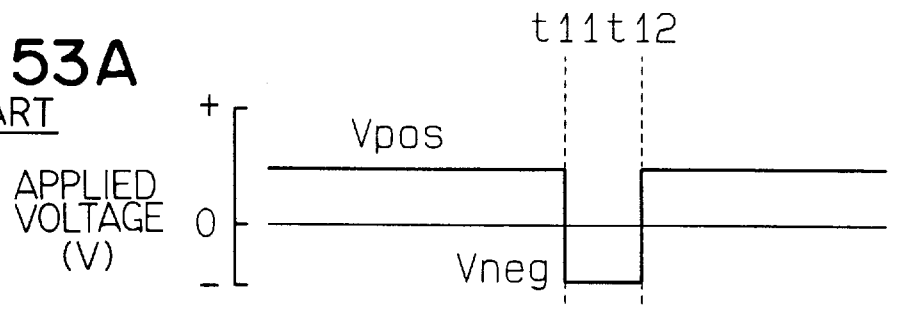
FIGS. 53A and 53B show waveforms of a voltage change and a current change due to such voltage change according to a conventional element resistance detection procedure.
Figure 53B:
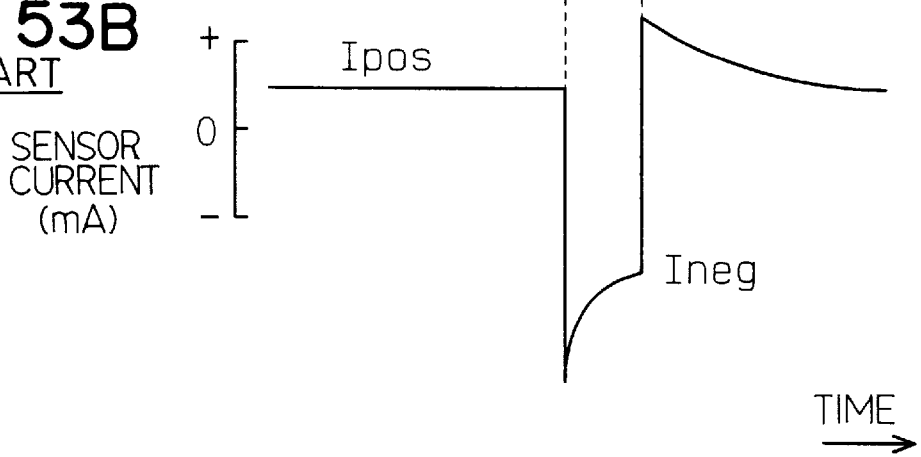

In order to perform the above control, the microprocessor 20 (FIG. 1) may be programmed to execute the main routine shown in FIG. 51 and element resistance detecting subroutine shown in FIG. 52. The main routine (FIG. 51) may be executed in the same manner as the main routine (FIG. 9) is executed in the first embodiment, while the subroutine (FIG. 52) which corresponds to step 130 in FIG. 51 is executed a bit differently from the subroutine of FIG. 10.

That is, the microprocessor 20 changes at step 132 the bias command signal Vr to a more positive side so that the voltage Vp for detecting the A/F ratio rises. At this time, the time period TA+TB from the time t1 to time t2 (FIG. 46A) of the voltage Vr is set longer than the time period required for the peak current ΔIp to attain its peak. The time period TA+TB may be less than 2.5 ms. However, the sensor current Ip is required to converge to the limit current value within the time period T1 (2 to 4 ms) for the next A/F ratio detection. Therefore, the time period TA+TB for detecting the element resistance is set shorter than that for detecting the A/F ratio. Preferably, the time period TA+TB is set to some tens of µs to 100 µs. After step 132, steps 134 and 135 are executed to detect the element resistance in the same manner as in the first embodiment.

In the above seventh embodiment, the voltage applied to the A/F ratio sensor 30 is changed at the predetermined time constant and maintained for a time period which is longer than a time period required for the sensor current Ip attains a maximum magnitude (peak). Thus, the sensor current Ip changes only very slightly during the time period TB enabling accurate detection of the current change caused by the applied voltage change.

Further, the time period for maintaining the voltage for the element resistance detection is set to be less than the digit of an inverse (1/f) of the cut-off frequency (f) specific to the sensor. That is, the time period is set to about 2.5 ms which is one digit smaller than the inverse of the cut-off frequency, about 40 Hz, of the sensor. As a result, the element resistance can be detected accurately without prolonging the time period for the element resistance detection.

The seventh embodiment may be modified so that the voltage applied to the A/F sensor 30 at the predetermined time constant for the element resistance detection is maintained unchanged, that is, at a magnitude existing at that moment once the sensor current Ip rises to its maximum magnitude (peak current). In this instance, step 132 in FIG. 52 may be modified to adjust the time period for the element resistance detection. In this modification also, the time period for maintaining the voltage unchanged is preferably set to be one-digit less than the inverse (1/f) of the cut-off frequency (f) specific to the sensor.

Although the present invention has been fully described in connection with preferred embodiments thereof with reference to the accompanying drawings, it is to be noted that various changes and modifications will become apparent to those skilled in the art.

For example, in the element resistance detection process of FIG. 10, although an order of setting the applied voltage to become negative and positive voltages is set depending on whether the A/F ratio at a given time is rich or lean according to the first embodiment, this order may be fixed regardless of the A/F ratio. In such a case, although the applied voltage is always changed from the positive side to the negative side or from the negative side to the positive side, preferably the negative ΔV and negative ΔI is measured when the A/F ratio is lean and the positive ΔV and positive ΔI is measured when the A/F ratio is rich. This is the same for the integrated type A/F ratio sensor 60 according to the sixth embodiment.

Moreover, the second to fifth embodiments may be implemented using the integrated type sensor described in the sixth embodiment. In such case, the same operations and effects as described above can be realized.

In the above described fifth embodiment, a first predetermined value for selectively using one of the element resistance detection method based on the voltage change and the element resistance detection method based on shutdown of the circuit is placed in the vicinity of the maximum value or the minimum value of the dynamic range while a second predetermined value is placed towards the central portion of the dynamic range. The second predetermined value may be used to selectively adjust the element resistance detection method based on the voltage change. That is, with the second predetermined value as the borderline, when the detected current is greater than the second predetermined value, the element resistance is detected based on the current change at only one of the positive and negative sides towards the inner side of the dynamic range and when the detected current is lesser than the second predetermined value, the element resistance is detected based on the total current change towards both the positive and negative sides that result from the application of voltage. In this case, detection accuracy of the element resistance becomes greater nearer the center of the dynamic range. Meanwhile, to eliminate discontinuity between the detected values of the element resistance which is caused by the selective use of the respective detection methods, a detection result at the center portion of the dynamic range may be used to compensate the respective detected values for both methods.

Meanwhile, when using the integrated type sensor described in the sixth embodiment, as described in the variations (FIGS. 13A–15D) of the first embodiment, it is also possible to change the waveform of applied voltage or the positions for measuring positions for the ΔV and ΔI.

Although in the above embodiments, the present invention is applied to the A/F ratio sensor for detecting oxygen concentration (A/F) in exhaust gas from a vehicle engine, the scope of application of the present invention is not limited only to the A/F ratio sensor for vehicles. The present invention can also be used for other applications. For example, it is possible to implement it for an oxygen concentration sensor for detecting a concentration of oxygen in, for example, combustible gas (methane gas, ethane gas and the like).

In the above embodiments, by providing digital signals generated by the microprocessor 20 with a predetermined time constant, the signals are converted to sine wave-like signals that are used for detecting element resistance. However, the microprocessor 20 may also generate sine wave signals and such signals may be used for detecting the element resistance.

Such changes and modifications are to be understood as being within the scope of the present invention as defined by the appended claims.

What is claimed is:

1. A method for detecting element resistance of an oxygen sensor which is used for determining oxygen concentration of a gas sample, said method comprising the steps of:

setting a time constant corresponding to a frequency at which impedance characteristics of said oxygen sensor are stable;

applying a changing voltage having said time constant to said oxygen sensor;

determining an electrical current change in electric current flowing in said oxygen sensor due to said changing voltage; and determining element resistance of said oxygen sensor based on said changing voltage and said current change.

2. A method for detecting element resistance according to claim 1, wherein said step of applying said changing voltage includes a step of applying a changing voltage that has a single voltage waveform having said time constant.

3. A method for detecting element resistance according to claim 1, wherein said step of setting said time constant includes the steps of:

determining a frequency range at which said impedance characteristics of said oxygen sensor are stable; and setting said time constant to correspond to a predetermined frequency within said frequency range.

4. A method for detecting element resistance according to claim 1, wherein said step of setting said time constant includes a step of setting said time constant to approximately 159 µs.

5. A method for detecting element resistance according to claim 1, wherein said step of applying said changing voltage includes a step of applying a changing voltage that has one of a positive slope and a negative slope.

6. A method for detecting element resistance according to claim 1, wherein:

said step of applying said changing voltage includes a step of applying a changing voltage that has a negative slope portion and a positive slope portion;

said step of determining said current change includes a step of determining said current change due to one of said negative slope portion and said positive slope portion; and said step of determining said element resistance includes a step of determining said element resistance based on said negative slope portion of said changing voltage and said current change when said step of determining said current change determines said current change based on said negative slope portion and a step of determining said element resistance based on said positive slope portion of said changing voltage and said current change when said step of determining said current change determines said current change based on said positive slope portion.

7. A method for detecting element resistance according to claim 1, further comprising the step of:

setting a current level within a detectable current range of said oxygen sensor;

wherein said step of applying said changing voltage includes a step of applying a changing voltage that has a negative slope portion when said electric current of said oxygen sensor is no less than said current level and a step of applying a changing voltage that has a positive slope portion when said electric current of said oxygen sensor is less than said current level, and said step of determining said current change includes a step of determining said current change due to said negative slope portion when said electric current of said oxygen sensor is no less than said current level and a step of determining said current change due to said positive slope portion when said electric current of said oxygen sensor is less than said current level.

8. A method for detecting element resistance according to claim 7, wherein said step of setting said current level includes a step of setting said current level to be at approximately a center of said detectable current range of said oxygen sensor.

9. A method for detecting element resistance according to claim 1, wherein:

said step of applying said changing voltage includes a step of applying a voltage to make said electric current flowing in said oxygen sensor negative when said oxygen sensor detects a lean air-fuel ratio and a step of applying a voltage to make said electric current flowing in said oxygen sensor positive when said oxygen sensor detects a rich air-fuel ratio.

10. A method for detecting element resistance according to claim 1, wherein:

said step of applying said changing voltage includes a step of applying a changing voltage that has a negative slope portion and a positive slope portion; and said step of determining said electrical current change includes a step of determining said current change due to both of said negative slope portion and said positive slope portion of said changing voltage.

11. A method for detecting element resistance according to claim 1, further comprising the step of setting said changing voltage to have a positive slope portion and a negative slope portion so that an amount of electric charge that moves within said oxygen sensor with said application of said positive slope portion is equal to an amount of electric charge that moves within said oxygen sensor with said application of said negative slope portion.

12. A method for detecting element resistance according to claim 1, said method additionally comprising the step of adjusting a magnitude of a next changing voltage in accordance with said element resistance determined by said step of determining said element resistance.

13. A method for detecting element resistance according to claim 1, wherein said step of setting said time constant is for setting said time constant to different values when said oxygen sensor is detecting said element resistance and when said oxygen sensor is detecting air-fuel ratio.

14. A method for detecting element resistance according to claim 13, wherein said step of setting said time constant includes the steps of:

preparing two different time constant values; and choosing which of said time constant values is to be set as said time constant depending on whether said oxygen sensor is detecting one of said element resistance and said air-fuel ratio.

15. A method for detecting element resistance according to claim 14, wherein said step of choosing said time constant includes a step of choosing a larger value among said time constant values as said time constant when said oxygen sensor is detecting said air-fuel ratio and a step of choosing a smaller value among said time constant values as said time constant when said oxygen sensor is detecting said element resistance.

16. A method for detecting element resistance of an oxygen sensor which is used for determining oxygen concentration of a gas sample, said method comprising the step of:

selectively executing at least one of:

a first detection method which includes the steps of setting a time constant corresponding to a frequency at which impedance characteristics of an oxygen sensor are stable, applying a changing voltage having said time constant to said oxygen sensor, determining a current change in electric current flowing in said oxygen sensor due to said changing voltage, and determining element resistance of said oxygen sensor based on said changing voltage and said current change; and a second detection method which includes the steps of deactuating said oxygen sensor, detecting a voltage change in voltage of said oxygen sensor after deactuating said oxygen sensor, detecting a current change in said electric current of said oxygen sensor due to said voltage change, and determining said element resistance based on said voltage change and said current change.

17. A method for detecting element resistance according to claim 16, further comprising the steps of:

setting at least one reference current level within a current detectable range of said oxygen sensor;

detecting an output current of said oxygen sensor; and setting an optimal current level corresponding to a stoichiometric air-fuel ratio, wherein said selectively executing step includes a step of selecting said first detection method when said output current is nearer to said optimal current level than said reference current level and a step of selecting said second detection method unless said output current is nearer to said optimal current level than said reference current level.

18. A method for detecting element resistance according to claim 17, wherein said step of setting said reference current level includes a step of setting said reference current level to be proximate to one of a minimum value of said current detectable range and a maximum value of said current detectable range.

19. A method for detecting element resistance according to claim 17, further comprising the step of setting a first reference value greater than and proximate to a minimum value of said current detectable range and a second reference value less than and proximate to said maximum value in said current detecting range;

wherein said selection step includes a step of selecting said first detection method when said output current is greater than said first reference value and lesser than said second reference value and a step of selecting said second detection method when said output current is no greater than said first reference value or no less than said second reference value.

20. A method for detecting element resistance according to claim 17, said method additionally comprising the step of setting at least one of a first reference range greater than and proximate to a minimum value of said current detectable range and a second reference range less than and proximate to said maximum value of said current detectable range;

wherein said selection step includes a step of selecting both of said first detection method and said second detection method when said output current is within one of said first reference range and said second reference range.

21. A method for detecting element resistance according to claim 20, further comprising the steps of:

determining a compensation coefficient based on said element resistance determined by said first detection method and said element resistance determined by said second detection method when said selection step selecting both said first detection method and said second detection method; and adjusting one of said element resistance determined by said first detection method and said element resistance determined by said second detection method based on said compensation coefficient.

22. A method for determining element resistance according to claim 16, said method additionally comprising the steps of:

determining said impedance characteristics of said oxygen sensor using said first detection method;

determining said impedance characteristics of said oxygen sensor using said second detection method;

determining a correction coefficient based on said impedance characteristics determined using said first detection method and said second detection method; and adjusting one of said element resistance determined by said first detection method and said element resistance determined by said second detection method.

23. A method for detecting element resistance of an oxygen sensor which produces a current corresponding to oxygen concentration of a gas sample in response to a voltage applied thereto, said method comprising the steps of:

switching, at a predetermined time constant, a magnitude of said voltage applied to said sensor for oxygen concentration detection to a magnitude for element resistance detection;

maintaining said magnitude of said voltage for said element resistance detection for more than a time period in which said current attains a peak magnitude; and determining an element resistance of said sensor based on a change in said magnitudes of said voltage and a change in magnitudes of said current.

24. A method for detecting element resistance according to claim 23, wherein said time period is more than one-digit less than an inverse of a cut-off frequency specific to said sensor.

25. A method for detecting element resistance of an oxygen sensor which produces a current corresponding to oxygen concentration of a gas sample in response to a voltage applied thereto, said method comprising the steps of:

switching, at a predetermined time constant, a magnitude of said voltage applied to said sensor for oxygen concentration detection to a magnitude for element resistance detection;

maintaining a magnitude of said voltage existing when said current attains a maximum magnitude for a time period after a maximum current magnitude attainment; and determining an element resistance of said sensor based on a change in said magnitudes of said voltage and a change in magnitudes of said current.

26. A method for detecting element resistance according to claim 25, wherein said time period is more than one-digit less than an inverse of a cut-off frequency specific to said sensor.

* * * * *